US011793833B2

(12) United States Patent
Levitsky

(10) Patent No.: US 11,793,833 B2
(45) Date of Patent: Oct. 24, 2023

(54) ENGINEERED B CELLS AND RELATED COMPOSITIONS AND METHODS

(71) Applicant: Juno Therapeutics, Inc., Seattle, WA (US)

(72) Inventor: Hyam I. Levitsky, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 1036 days.

(21) Appl. No.: 16/465,109

(22) PCT Filed: Nov. 30, 2017

(86) PCT No.: PCT/US2017/064075
§ 371 (c)(1),
(2) Date: May 29, 2019

(87) PCT Pub. No.: WO2018/102612
PCT Pub. Date: Jun. 7, 2018

(65) Prior Publication Data
US 2019/0321403 A1   Oct. 24, 2019

Related U.S. Application Data

(60) Provisional application No. 62/429,709, filed on Dec. 2, 2016.

(51) Int. Cl.
| | |
|---|---|
| *A61K 35/17* | (2015.01) |
| *A61J 1/10* | (2006.01) |
| *C07K 16/28* | (2006.01) |
| *C12N 15/62* | (2006.01) |
| *C12N 15/85* | (2006.01) |
| *A61K 45/06* | (2006.01) |

(52) U.S. Cl.
CPC .............. *A61K 35/17* (2013.01); *A61J 1/10* (2013.01); *C07K 16/28* (2013.01); *C12N 15/62* (2013.01); *C12N 15/85* (2013.01); *A61K 45/06* (2013.01); *C12N 2015/8518* (2013.01)

(58) Field of Classification Search
CPC .................................................... A61K 35/17
See application file for complete search history.

(56) References Cited

U.S. PATENT DOCUMENTS

| | | | |
|---|---|---|---|
| 4,235,871 | A | 11/1980 | Papahadjopoulos et al. |
| 4,452,773 | A | 6/1984 | Molday |
| 4,501,728 | A | 2/1985 | Geho et al. |
| 4,690,915 | A | 9/1987 | Rosenberg |
| 4,795,698 | A | 1/1989 | Owen et al. |
| 4,837,028 | A | 6/1989 | Allen |
| 4,897,355 | A | 1/1990 | Eppstein et al. |
| 4,946,787 | A | 8/1990 | Eppsstein et al. |
| 5,019,369 | A | 5/1991 | Presant et al. |
| 5,049,386 | A | 9/1991 | Epstein et al. |
| 5,087,616 | A | 2/1992 | Myers et al. |
| 5,200,084 | A | 4/1993 | Liberti et al. |
| 5,204,244 | A | 4/1993 | Fell et al. |
| 5,219,740 | A | 6/1993 | Miller et al. |
| 5,356,802 | A | 10/1994 | Chandrasegaran et al. |
| 5,436,150 | A | 7/1995 | Chandrasegaran |
| 5,487,994 | A | 1/1996 | Chandrasegaran |
| 5,731,168 | A | 3/1998 | Carter et al. |
| 6,040,177 | A | 3/2000 | Riddell et al. |
| 6,060,273 | A | 5/2000 | Dirks et al. |
| 6,140,081 | A | 10/2000 | Barbas et al. |
| 6,207,453 | B1 | 3/2001 | Maass et al. |
| 6,453,242 | B1 | 9/2002 | Eisenberg et al. |
| 6,503,717 | B2 | 1/2003 | Case et al. |
| 6,534,261 | B1 | 3/2003 | Cox et al. |
| 6,599,692 | B1 | 7/2003 | Case et al. |
| 6,689,558 | B2 | 2/2004 | Case |
| 6,794,136 | B1 | 9/2004 | Eisenberg et al. |
| 7,030,215 | B2 | 4/2006 | Rebar et al. |
| 7,067,317 | B2 | 6/2006 | Rebar et al. |
| 7,070,934 | B2 | 7/2006 | Cox et al. |
| 7,253,273 | B2 | 8/2007 | Collingwood |
| 7,262,054 | B2 | 8/2007 | Jamieson et al. |

(Continued)

FOREIGN PATENT DOCUMENTS

| | | |
|---|---|---|
| EP | 452342 | 10/1991 |
| WO | WO 1991/016024 | 10/1991 |

(Continued)

OTHER PUBLICATIONS

Tonika Lam (PhD dissertation. UC Irvine. "Using a naturally occurring viral protein and a small molecule compound to inhibit B cell immunoglobulin class-switch DNA recombination" 2014). (Year: 2014).*
Monroe et al. (ITAM-mediated tonic signalling through pre-BCR and BCR complexes. Nat Rev Immunol 6, 283-294 (2006)). (Year: 2006).*
Delogu et al., "Gene repression by Pax5 in B cells is essential for blood cell homeostasis and is reversed in plasma cells," Immunity (2006) 24(3):269-281.
Magari et al. "Enhancement of antibody production from a chicken B cell line DT40 by Yeducing Pax5 expression." Journal of Bioscience and Bioengineering, Feb. 2009, 107(2): 206-209.
Roessler et al. "Distinct Promoters Mediate the Regulation of Ebf1 Gene Expression by Interleukin-7 and Pax5", Molecular and Cellular Biology. (2006) 27(2): 579-594.

(Continued)

*Primary Examiner* — Christopher M Babic
*Assistant Examiner* — Kimberly A Aron
(74) *Attorney, Agent, or Firm* — Morrison & Foerster LLP

(57) ABSTRACT

Provided herein are engineered B cells, such as for adoptive cell therapy. In some aspects, also provided are methods and compositions for engineering and producing the cells, compositions containing the cells, and methods for their administration to subjects. In some embodiments, the cells are engineered to produce and/or secrete an exogenous protein, such as a therapeutic protein, including antibodies and antigen-binding fragments thereof. In some aspects, features of the cells and methods provide for increased or improved activity, efficacy and/or persistence of the cells.

41 Claims, No Drawings

Specification includes a Sequence Listing.

(56) References Cited

U.S. PATENT DOCUMENTS

| | | | |
|---|---|---|---|
| 7,361,635 | B2 | 4/2008 | Miller et al. |
| 7,446,190 | B2 | 11/2008 | Sadelain et al. |
| 8,133,727 | B2 | 3/2012 | Luo et al. |
| 8,802,374 | B2 | 8/2014 | Jensen et al. |
| 8,822,647 | B2 | 9/2014 | Jensen |
| 9,005,974 | B2 | 4/2015 | Spits |
| 9,206,247 | B2 | 12/2015 | Beaumont et al. |
| 2003/0170238 | A1 | 9/2003 | Gruenberg et al. |
| 2004/0029271 | A1 | 2/2004 | Busslinger et al. |
| 2005/0064474 | A1 | 3/2005 | Urnov et al. |
| 2005/0267061 | A1 | 12/2005 | Martin |
| 2006/0188987 | A1 | 8/2006 | Guschin et al. |
| 2007/0116690 | A1 | 5/2007 | Yang et al. |
| 2007/0218528 | A1 | 9/2007 | Miller |
| 2011/0003380 | A1 | 6/2011 | Miltenyi et al. |
| 2011/0301073 | A1 | 12/2011 | Gregory et al. |
| 2013/0164277 | A1 | 6/2013 | Hyde et al. |
| 2013/0315884 | A1 | 11/2013 | Galetto et al. |
| 2013/0316366 | A1 | 11/2013 | Yu et al. |
| 2014/0120622 | A1 | 5/2014 | Gregory et al. |
| 2014/0271635 | A1 | 9/2014 | Brogdon et al. |
| 2016/0289637 | A1 | 10/2016 | Goldberg et al. |
| 2016/0355783 | A1* | 12/2016 | Hyde .................. C07K 16/109 |

FOREIGN PATENT DOCUMENTS

| | | | |
|---|---|---|---|
| WO | WO 1991/017424 | 11/1991 | |
| WO | WO 1992/008796 | 5/1992 | |
| WO | WO 1994/028143 | 12/1994 | |
| WO | WO 1994/029438 | 12/1994 | |
| WO | WO 1995/033824 | 12/1995 | |
| WO | WO 1997/012052 | 4/1997 | |
| WO | WO 1998/050431 | 11/1998 | |
| WO | WO 1998/053058 | 11/1998 | |
| WO | WO 1998/053059 | 11/1998 | |
| WO | WO 1998/053060 | 11/1998 | |
| WO | WO 2001/011067 | 2/2001 | |
| WO | WO 2002/016536 | 2/2002 | |
| WO | WO 2002/018609 | 3/2002 | |
| WO | WO 2003/016496 | 2/2003 | |
| WO | WO 2005/063816 | 7/2005 | |
| WO | WO 2007/067046 | 6/2007 | |
| WO | WO 2009/072003 | 6/2009 | |
| WO | WO 2010/033140 | 3/2010 | |
| WO | WO 2010/034103 | 4/2010 | |
| WO | WO 2011/147622 | 12/2011 | |
| WO | WO 2012/072814 | 6/2012 | |
| WO | WO 2013/014537 | 1/2013 | |
| WO | WO 2013/144566 | 10/2013 | |
| WO | WO 2014/026110 | 2/2014 | |
| WO | WO 2014/031687 | 2/2014 | |
| WO | WO 2014/055668 | 4/2014 | |
| WO | WO 2014/146074 | 9/2014 | |
| WO | WO 2015/148879 | 10/2015 | |
| WO | WO2016/100932 | * 6/2016 | ............... C12N 5/00 |
| WO | WO 2016/100932 | 6/2016 | |
| WO | WO 2018/175390 | 9/2018 | |

OTHER PUBLICATIONS

Schebesta et al. "Control of Pre-BCR signaling by Pax-5 dependent activation of the BLNK gene." Immunity. (2002) 17(4):473-485.

Aida et al. "Cloning-free CRISPR/Cas system facilitates functional cassette knock-in in mice," Genome Biol. (2015) 16: 87.

Alonso-Camino et al., "CARbodies: Human Antibodies Against Cell Surface Tumor Antigens Selected From Repertoires Displayed on T Cell Chimeric Antigen Receptors," Mol Ther Nucleic Acids (2013) 2(5):e93.

Anderson, W.F. Human Gene Therapy, Science (1992) 256:808-813.

Auer et al. "Highly efficient CRISPR/Cas9-mediated knock-in in zebrafish by homology-independent DNA repair," Genome research (2014) 24(1):142-153.

Balazs et al., "Antibody-based protection against HIV infection by vectored immunoprophylaxis." Nature (2012) 481:81-84.

Balazs et al., "Vectored immunoprophylaxis protects humanized mice from mucosal HIV transmission." Nature Medicine (2014) 20:296-300.

Beerli et al., "Engineering polydactyl zinc-finger transcription factors," Nat Biotechnol. (2002) 20(2):135-141.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Cavalieri et al., "Human T lymphocytes transduced by lentiviral vectors in the absence of TCR activation maintain an intact immune competence," Blood (2003) 102(2): 497-505.

Chicaybam et al., "An efficient low cost method for gene transfer to T lymphocytes," PLoS One (2013) 8(3): e60298.

Cho et al., "Human mammalian cell sorting using a highly integrated micro-fabricated fluorescence-activated cell sorter (microFACS)," Lab Chip (2010) 10: 1567-1573.

Choo et al., "Advances in zinc finger engineering," Curr Opin Struct Biol. (2000) 10(4): 411-416.

Cooper et al., "T-cell clones can be rendered specific for CD19: toward the selective augmentation of the graft-versus-B-lineage leukemia effect," Blood. (2003) 101: 1637-1644.

Critchlow et al., "DNA end-joining: from yeast to man," Trends Biochem Sci. (1998) 23(10): 394-398.

Davila et al., "CD19 CAR-targeted T cells induce long-term remission and B Cell Aplasia in an immunocompetent mouse model of B cell acute lymphoblastic leukemia," PLoS One (2013) 8(4): e61338.

De Felipe, "Skipping the co-expression problem: the new 2A "CHYSEL" technology," Genet Vaccines Ther (2004) Sep. 13;2(1):13.

De Felipe, "Targeting of proteins derived from self-processing polyproteins containing multiple signal sequences," Traffic (2004) 5(8): 616-626.

Deisenhofer et al., "Crystallographic refinement and atomic models of a human Fc fragment and its complex with fragment B of protein A from Staphylococcus aureus at 2.9- and 2.8-A resolution," Biochemistry. (1981) 20(9): 2361-2370.

Dillon, "Regulating gene expression in gene therapy," Trends Biotechnol. (1993) 11(5): 167-173.

Doores et al. "Two Classes of Broadly Neutralizing Antibodies within a Single Lineage Directed to the High-Mannose Patch of HIV Envelope," J. Virol, (2015) 89(2): 1105-1118.

Ernst, P. "Combinatorial regulation of transcription II: the immunoglobulin μ heavy chain gene," Immunity (1995) 2(5): 427-438.

Falkowska et al. "Broadly Neutralizing HIV Antibodies Definea Glycan-Dependent Epitope on the Prefusion Conformation of gp41 on Cleaved Envelope Trimers," Immunity (2014) 40(5): 657-668.

Fusil et al., "A lentiviral vector allowing physiologically regulated membrane-anchored and secreted antibody expression depending on B-cell maturation status," Molecular Therapy (2015) 23(11): 1734-1747.

Gaj et al.. "ZFN, TALEN, and CRISPR/Cas-Based Methods For Genome Engineering," Trends Biotechnol. (2013) 31(7): 397-405.

Godin et al., "Microfluidics and photonics for Bio-System-on-a-Chip: a review of advancements in technology towards a microfluidic flow cytometry chip," J Biophoton. (2008) 1(5):355-376.

Grosschedl et al. "Cell-type specificity of iminunoglobulin gene expression is regulated by at least three DNA sequence elements," Cell (1985) 41(3): 885-897.

Haryadi et al., "Optimization of Heavy Chain and Light Chain Signal Peptides for High Level Expression of Therapeutic Antibodies in CHO Cells," PLoS one,(2015) 10(2): e0116878.

(56) References Cited

OTHER PUBLICATIONS

Hermans et al., "The VITAL assay: a versatile fluoro metric technique for assessing CTL- and NKT-mediated cytotoxicity against multiple targets in vitro and in vivo," J. Immunological Methods (2004) 285(1): 25-40.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res. (2013) 19(12): 3153-3164.
Isalan et al., "A rapid, generally applicable method to engineer zinc fingers illustrated by targeting the HIV-1 promoter," Nat Biotechnol. (2001) 19(7): 656-660.
Johnston, et al., "Biolistic transformation: microbes to mice," Nature (1990) 346: 776-777.
Ju et al. "Evidence for Physical Interaction between the Immunoglobulin Heavy Chain Variable Region and the 3' Regulatory Region," Journal of Biological Chemistry (2007) 282(48): 35169-35178.
Kim et al., "Chimeric restriction endonuclease," Proc Natl Acad Sci U S A. (1994) 91(3): 883-887.
Kim et al., "Insertion and deletion mutants of FokI restriction endonuclease," J Biol Chem. (1994) 269(50): 31978-31982.
Kim et al., "A library of TAL effector nucleases spanning the human genome," Nat Biotechnol. (2013) 31(3): 251-258.
Kimura et al. "Efficient generation of knock-in transgenic zebrafish carrying reporter/driver genes by CRISPR/Cas9-mediated genome engineering," Sci Rep. (2014) 4: 6545.
Kindt, T.J. et al. "Antigens And Antibodies," Chapter 4 In Kuby Immunology 6th Ed., W.H. Freeman And Co., (2007). p. 91.
Klebanoff et al., "Sorting through subsets: which T-cell populations mediate highly effective adoptive immunotherapy?," J Immunother. (2012) 35(9): 651-660.
Kochenderfer et al., "Construction and preclinical evaluation of an anti-CD19 chimeric antigen receptor," J. Immunotherapy (2009) 32(7): 689-702.
Koff W.C. "Defeating the virus, Recent discoveries are spurring a renaissance in HIV vaccine research and development," The Scientist, (2015) pp. 1-8.
Koste et al., "T-cell receptor transfer into human T cells with ecotropic retroviral vectors," Gene Therapy (2014) 21: 533-538.
Kremer et al., "Adenovirus and adeno-associated virus mediated gene transfer," Br Med Bull. (1995) 51(1):31-44.
Krumm et al., "Mechanisms of escape from the PGT128 famiy of anti-HIVV broadly meutralizing antibodies." Retrovirology (2016) 13:8 pp. 1-15.
Kwong et al., "Rational design of vacines to elicit broadly neutralizing antibodies to HIV-1." Cold Spring Harb Perspect Med (2011) 1:a007278 pp. 1-16.
Laumen et al. "The BOB.1/OBF.1 co-activator is essential for octamer-dependent transcription in B cells," European journal of immunology (2000) 30(2): 458-469.
Lee et al., "Activated B cells modified by electroporation of multiple mRNAs encoding immune stimulatory molecules are comparable to mature dendritic cells in inducing in vitro antigen-specific T-cell responses," Immunology (2008) 125(2): 229-240.
Li et al., "Functional domains in Fok I restriction endonuclease," Proc Natl Acad Sci U S A. (1992) 89(10): 4275-4279.
Li et al.,"Alteration of the cleavage distance of Fok I restriction endonuclease by insertion mutagenesis," Proc Natl Acad Sci U S A. (1993) 90(7):2764-2768.
Li et al., "Mechanism of neutralization by the broadly neutralizing HIV-1 monoclonal antibody VRC01." J. Virol. (2011) 85(17): 8954-8967.
Liu et al., "Inclusion of Strep-tag II in design of antigen receptors for T-cell immunotherapy," Nat Biotechnol (2016) 34(4):430-434.
Lloyd et al., "Beyond the antigen receptor: editing the genome of T-cells for cancer adoptive cellular therapies," Front Immunol (2013) 4(221):1-7.

Lu et al., "Enhanced clearance of HIV-1-infected cells by broadly neutralizing antibodies against HIV-1 in vivo," Science, (2016) 352(6288): 1001-1004.
Luo et al. "Engineering human hematopoietic stem/progenitor cells to produce a broadly neutralizing anti-HIV antibody after in vitro maturation to human B lymphocytes," Blood (2009) 113(7): 1422-1431.
Lupton et al., "Dominant positive and negative selection using a hygromycin phosphotransferase-thymidine kinase fusion gene," Mol. and Cell Biol. (1991) 11(6): 3374-3378.
Manuri et al., "piggyBac transposon/transposase system to generate CD19-specific T cells for the treatment of B-lineage malignancies," Hum Gene Ther (2010) 21(4): 427-437.
Merchant, A. M. et al. "An Efficient Route To Human Bispecific IgG," Nature Biotechnology (1998) 16: 677-681.
Miller et al., "Improved retroviral vectors for gene transfer and expression," BioTechniques (1989) 7: 980-990.
Miller, "Protein-protein recognition and the association of immunoglobulin constant domains," J Mol Biol. (1990) 216(4): 965-973.
Miller et al., "Retrovirus packaging cells," Human Gene Therapy (1990) 1: 5-14.
Miller, "Human gene therapy comes of age," Nature. (1992) 357(6378): 455-460.
Mitani et al., "Delivering therapeutic genes—matching approach and application," Trends Biotechnol. (1993) 11(5): 162-166.
Nabel et al., "Direct gene transfer for immunotherapy and immunization," Trends Biotechnol. (1993) 11(5): 211-215.
Nikolajaczyk et al. "Mechanisms of μ enhancer regulation in B lymphocytes," Cold Spring Harbor symposia on quantitative biology (1999) 64: 99-107.
Novellino et al. "A listing of human tumor antigens recognized by T cells: Mar. 2004 update," Cancer Immunol Immunother (2005) 54:187-207.
Nutt et al., "The generation of antibody-secreting plasma cells," Nature Reviews Immunology (2015) 15: 160-171.
Pabo et al., "Design and selection of novel Cys2His2 zinc finger proteins," Annu Rev Biochem. (2001) 70: 313-340.
Park et al., "Treating cancer with genetically engineered T cells," Trends Biotechnol. (2011) 29(11): 550-557.
Park et al. "CRISPR/Cas9 Allows Efficient and Complete Knock-In of a Destabilization Domain-Tagged Essential Protein in a Human Cell Line, Allowing Rapid Knockdown of Protein Function," PloS one (2014) 9(4): e95101.
Parmiani et al., "Unique human tumor antigens: immunobiology and use in clinical trials," J Immunol (2007) 178(4): 1975-1979.
Perez-Pinera et al. "RNA-guided gene activation by CRISPR-Cas9-based transcription factors," Nature methods, (2013) 10(10): 973-976.
Portolano et al., "Lack of promiscuity in autoantigen-specific H and L chain combinations as revealed by human H and L chain "roulette"," J. Immunol. (1993) 150(3): 880-887.
Potratz et al., "Receptor tyrosine kinase gene expression profiles of Ewing sarcomas reveal ROR1 as a potential therapeutic target in metastatic diseas," Mol Oncol (2016) 10(5): 677-692.
Pritchard et al., "Glycan clustering stabilizes the mannose patch of HIV-1 and preserves vulnerability to broadly neutralizing antibodies," Nat Commun. (2015) 6: Article No. 7479; 11 pages.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3: 319-338.
Ridgway et al., "'Knobs-into-holes' engineering of antibody CH3 domains for heavy chain heterodimerization," Protein Eng. (1996) 9(7): 617-621.
Rockefeller University "Antibody therapy opens door to potential new treatment for HIV," Science Daily (2016) pp. 1-3.
Rosenberg, et al., "Cell transfer immunotherapy for metastatic solid cancer—what clinicians need to know," Nat Rev Clin Oncol. (2011) 8(10): 577-85).
Sander et al. (Apr. 2014). "CRISPR-Cas Systems for Genome Editing, Regulation and Targeting," Nature Biotechnology 32(4): 347-355, 24 pages.

(56) References Cited

OTHER PUBLICATIONS

Scarpa et al., "Characterization of recombinant helper retroviruses from Moloneybased vectors in ecotropic and amphotropic packaging cell lines," Virology (1991) 180: 849-852.
Segal et al., "Custom DNA-binding proteins come of age: polydactyl zinc-finger proteins," Curr Opin Biotechnol. (2001) 12(6): 632-637.
Sensi et al., "Unique Tumor Antigens: Evidence for Immune Control of Genome Integrity and Immunogenic Targets for T Cell-Mediated Patient-Specific Immunotherapy," Clin Cancer Res (2006) 12(17): 5023-32.
Sharma et al., "Efficient sleeping beauty DNA transposition from DNA minicircles," Molec Ther Nucl Acids (2013) 2 :e74.
Shin et al., "Co-expression of CD40L with CD70 and antitumor efficacy," Oncotarget, Oncotarget. (2016) 7(29): 46173-46186.
Sok et al. "The Effects of Somatic Hypermutation on Neutralization and Binding in the PGT121 Family of Broadly Neutralizing HIV Antibodies," PLoS Pathog, (2013) 9(11), e1003754.
Sok et al. "Promiscuous glycan site recognition by antibodies to the high-mannose patch of gp120 broadens neutralization of HIV," Science translational medicine, (2014) 6(236), 236ra63-236ra63.
Szoka et al., "Comparative properties and methods of preparation of lipid vesicles (liposomes)," Ann. Rev. Biophys. Bioeng. (1980) 9: 467-508.
Terakura et al., "Generation of CD19-chimeric antigen receptor modified CD8+ T cells derived from virus-specific central memory T cells," Blood (2012) 1: 72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1): 84-89.
Van Brunt, "Molecular Farming: Transgenic Animals as Bioreactors," Nat Biotechnol. (1988) 6(10): 1149-1154.
Van Tendeloo et al., "High-level transgene expression in primary human T lymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Vigne et al., "Third-generation adenovectors for gene therapy," Restor Neurol Neurosci. (1995) 8(1): 35-36.
Wadhwa et al., "Receptor mediated glycotargeting," J. Drug Targeting (1995) 3(2):111-127.
Wang et al., "Phenotypic and functional attributes of lentivirus-modified CD19-specific human CD8+ central memory T cells manufactured at clinical scale," J Immunother (2012) 35(9): 689-701.
Yu et al., "Progress towards gene therapy for HIV infection," Gene Ther. (1994) 1(1): 13-26.
Yu et al., "Use of mutated self-cleaving 2A peptides as a molecular rheostat to direct simultaneous formation of membrane and secreted anti-HIV immunoglobulins," PLOS One, Nov. 2012, vol. 7, Issue 11, e50438.
Pridans et al., "Identification of Pax5 target genes in early B cell differentiation1," J Immunol (2008) 180:1719-1728.

* cited by examiner

SEQUENCE LISTING

<160> NUMBER OF SEQ ID NOS: 208

<210> SEQ ID NO 1
<211> LENGTH: 18
<212> TYPE: PRT
<213> ORGANISM: Artificial Sequence
<220> FEATURE:
<223> OTHER INFORMATION: T2A

<400> SEQUENCE: 1

Glu Gly Arg Gly Ser Leu Leu Thr Cys Gly Asp Val Glu Glu Asn Pro
1               5                   10                  15

Gly Pro

<210> SEQ ID NO 2
<211> LENGTH: 19
<212> TYPE: PRT
<213> ORGANISM: Artificial Sequence
<220> FEATURE:
<223> OTHER INFORMATION: P2A

<400> SEQUENCE: 2

Ala Thr Asn Phe Ser Leu Leu Lys Gln Ala Gly Asp Val Glu Glu Asn
1               5                   10                  15

Pro Gly Pro

<210> SEQ ID NO 3
<211> LENGTH: 20
<212> TYPE: PRT
<213> ORGANISM: Artificial Sequence
<220> FEATURE:
<223> OTHER INFORMATION: E2A

<400> SEQUENCE: 3

Gln Cys Thr Asn Tyr Ala Leu Leu Lys Leu Ala Gly Asp Val Glu Ser
1               5                   10                  15

Asn Pro Gly Pro
                20

<210> SEQ ID NO 4
<211> LENGTH: 22
<212> TYPE: PRT
<213> ORGANISM: Artificial Sequence
<220> FEATURE:
<223> OTHER INFORMATION: F2A

<400> SEQUENCE: 4

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 5
<211> LENGTH: 335
<212> TYPE: PRT
<213> ORGANISM: Artificial Sequence
<220> FEATURE:
<223> OTHER INFORMATION: truncated EGFR (tEGFR)

<400> SEQUENCE: 5

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His

```
                   275                 280                 285
Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 6
<211> LENGTH: 12
<212> TYPE: PRT
<213> ORGANISM: Homo sapiens
<220> FEATURE:
<223> OTHER INFORMATION: spacer (IgG4hinge)

<400> SEQUENCE: 6

Glu Ser Lys Tyr Gly Pro Pro Cys Pro Pro Cys Pro
1               5                   10

<210> SEQ ID NO 7
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 7

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gly Asn Val Phe Ser
                85                  90                  95

Cys Ser Val Met His Glu Ala Leu His Asn His Tyr Thr Gln Lys Ser
                100                 105                 110

Leu Ser Leu Ser Leu Gly Lys
        115

<210> SEQ ID NO 8
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 8

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 9
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 9

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
                20                  25                  30

Thr Thr Arg Asn Thr Gly Arg Gly Gly Glu Glu Lys Lys Lys Glu Lys
            35                  40                  45

Glu Lys Glu Glu Gln Glu Glu Arg Glu Thr Lys Thr Pro Glu Cys Pro
50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
            245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
            275                 280

<210> SEQ ID NO 10
<211> LENGTH: 20
<212> TYPE: DNA
<213> ORGANISM: Artificial Sequence
<220> FEATURE:
<223> OTHER INFORMATION: PAX5 gRNA target 1

<400> SEQUENCE: 10
gctgatggag tacgacgagc                                              20

<210> SEQ ID NO 11
<211> LENGTH: 20
<212> TYPE: DNA
<213> ORGANISM: Artificial Sequence
<220> FEATURE:
<223> OTHER INFORMATION: PAX5 gRNA target 2

<400> SEQUENCE: 11
tgtgaatgga cggccactcc                                              20

<210> SEQ ID NO 12
<211> LENGTH: 20
<212> TYPE: DNA
<213> ORGANISM: Artificial Sequence
<220> FEATURE:
<223> OTHER INFORMATION: PAX5 gRNA target 3

<400> SEQUENCE: 12
ggctcgtcgt actccatcag                                              20

<210> SEQ ID NO 13
<211> LENGTH: 20
<212> TYPE: DNA
<213> ORGANISM: Artificial Sequence
<220> FEATURE:
<223> OTHER INFORMATION: PAX5 gRNA target 4

<400> SEQUENCE: 13
ttggatcctc caattacccc                                              20

<210> SEQ ID NO 14
<211> LENGTH: 20
<212> TYPE: DNA
<213> ORGANISM: Artificial Sequence
<220> FEATURE:
<223> OTHER INFORMATION: PAX5 gRNA target 5

<400> SEQUENCE: 14
ggtcctaggt attatgagac                                              20

<210> SEQ ID NO 15
<211> LENGTH: 20
<212> TYPE: DNA
<213> ORGANISM: Artificial Sequence
<220> FEATURE:
<223> OTHER INFORMATION: PAX5 gRNA target 6

<400> SEQUENCE: 15
tgtagtccgc cagaggatag                                              20

<210> SEQ ID NO 16
<211> LENGTH: 20
<212> TYPE: DNA
<213> ORGANISM: Artificial Sequence
<220> FEATURE:
<223> OTHER INFORMATION: BACH2 gRNA target 1

<400> SEQUENCE: 16
cagtattaac cctgcgccct                                              20

<210> SEQ ID NO 17
<211> LENGTH: 20
<212> TYPE: DNA
<213> ORGANISM: Artificial Sequence
<220> FEATURE:
<223> OTHER INFORMATION: BACH2 gRNA target 2

<400> SEQUENCE: 17
cggcccagcg ctgccgcaaa                                              20

<210> SEQ ID NO 18
<211> LENGTH: 20
<212> TYPE: DNA
<213> ORGANISM: Artificial Sequence
<220> FEATURE:
<223> OTHER INFORMATION: BACH2 gRNA target 3

<400> SEQUENCE: 18
gtctgcttcc gagaacgatc                                              20

<210> SEQ ID NO 19
<211> LENGTH: 20
<212> TYPE: DNA
<213> ORGANISM: Artificial Sequence
<220> FEATURE:
<223> OTHER INFORMATION: BACH2 gRNA target 4

<400> SEQUENCE: 19
gttcctgcgc atgcacaacc                                              20

<210> SEQ ID NO 20
<211> LENGTH: 20
<212> TYPE: DNA
<213> ORGANISM: Artificial Sequence
<220> FEATURE:
<223> OTHER INFORMATION: BACH2 gRNA target 5

<400> SEQUENCE: 20
agtttattca tgatgtccga                                              20

<210> SEQ ID NO 21
<211> LENGTH: 20
<212> TYPE: DNA
<213> ORGANISM: Artificial Sequence
<220> FEATURE:
<223> OTHER INFORMATION: BACH2 gRNA target 6

```
<400> SEQUENCE: 21
ctgtgacgtg actttgatcg                                              20

<210> SEQ ID NO 22
<211> LENGTH: 20
<212> TYPE: DNA
<213> ORGANISM: Artificial Sequence
<220> FEATURE:
<223> OTHER INFORMATION: BCL6 gRNA target 1

<400> SEQUENCE: 22
ctacaagtgt gaccgctgcc                                              20

<210> SEQ ID NO 23
<211> LENGTH: 20
<212> TYPE: DNA
<213> ORGANISM: Artificial Sequence
<220> FEATURE:
<223> OTHER INFORMATION: BCL6 gRNA target 2

<400> SEQUENCE: 23
cagggccata ccggtatgga                                              20

<210> SEQ ID NO 24
<211> LENGTH: 20
<212> TYPE: DNA
<213> ORGANISM: Artificial Sequence
<220> FEATURE:
<223> OTHER INFORMATION: BCL6 gRNA target 3

<400> SEQUENCE: 24
gagccgcagg acgtgcactt                                              20

<210> SEQ ID NO 25
<211> LENGTH: 20
<212> TYPE: DNA
<213> ORGANISM: Artificial Sequence
<220> FEATURE:
<223> OTHER INFORMATION: BCL6 gRNA target 4

<400> SEQUENCE: 25
taaccagacc cttccggttc                                              20

<210> SEQ ID NO 26
<211> LENGTH: 20
<212> TYPE: DNA
<213> ORGANISM: Artificial Sequence
<220> FEATURE:
<223> OTHER INFORMATION: BCL6 gRNA target 5

<400> SEQUENCE: 26
tgttaacgat gttattgagc                                              20

<210> SEQ ID NO 27
<211> LENGTH: 20
<212> TYPE: DNA
<213> ORGANISM: Artificial Sequence
<220> FEATURE:
<223> OTHER INFORMATION: BCL6 gRNA target 6

<400> SEQUENCE: 27
agcatgttgt ggacacttgc                                              20

<210> SEQ ID NO 28
```

```
<211> LENGTH: 20
<212> TYPE: DNA
<213> ORGANISM: Artificial Sequence
<220> FEATURE:
<223> OTHER INFORMATION: OBF1 gRNA target 1

<400> SEQUENCE: 28
ttcacacgga cgccctggta                                              20

<210> SEQ ID NO 29
<211> LENGTH: 20
<212> TYPE: DNA
<213> ORGANISM: Artificial Sequence
<220> FEATURE:
<223> OTHER INFORMATION: OBF1 gRNA target 2

<400> SEQUENCE: 29
actctcaccg ccgtaggtgc                                              20

<210> SEQ ID NO 30
<211> LENGTH: 20
<212> TYPE: DNA
<213> ORGANISM: Artificial Sequence
<220> FEATURE:
<223> OTHER INFORMATION: OBF1 gRNA target 3

<400> SEQUENCE: 30
ctccaaaagc agcttgtcga                                              20

<210> SEQ ID NO 31
<211> LENGTH: 20
<212> TYPE: DNA
<213> ORGANISM: Artificial Sequence
<220> FEATURE:
<223> OTHER INFORMATION: OBF1 gRNA target 4

<400> SEQUENCE: 31
aagctccgcc acgcccgcag                                              20

<210> SEQ ID NO 32
<211> LENGTH: 20
<212> TYPE: DNA
<213> ORGANISM: Artificial Sequence
<220> FEATURE:
<223> OTHER INFORMATION: OBF1 gRNA target 5

<400> SEQUENCE: 32
agaggcatag gtcaacactg                                              20

<210> SEQ ID NO 33
<211> LENGTH: 20
<212> TYPE: DNA
<213> ORGANISM: Artificial Sequence
<220> FEATURE:
<223> OTHER INFORMATION: OBF1 gRNA target 6

<400> SEQUENCE: 33
agcttcatgg ggcacatact                                              20

<210> SEQ ID NO 34
<211> LENGTH: 20
<212> TYPE: DNA
<213> ORGANISM: Artificial Sequence
<220> FEATURE:
<223> OTHER INFORMATION: OCT2 gRNA target 1

<400> SEQUENCE: 34
```
gactccccat cagagcacac                                                20

<210> SEQ ID NO 35
<211> LENGTH: 20
<212> TYPE: DNA
<213> ORGANISM: Artificial Sequence
<220> FEATURE:
<223> OTHER INFORMATION: OCT2 gRNA target 2

<400> SEQUENCE: 35
tgctcagttc ctgctaccgc                                                20

<210> SEQ ID NO 36
<211> LENGTH: 20
<212> TYPE: DNA
<213> ORGANISM: Artificial Sequence
<220> FEATURE:
<223> OTHER INFORMATION: OCT2 gRNA target 3

<400> SEQUENCE: 36
ccagttgggg acacggagaa                                                20

<210> SEQ ID NO 37
<211> LENGTH: 20
<212> TYPE: DNA
<213> ORGANISM: Artificial Sequence
<220> FEATURE:
<223> OTHER INFORMATION: OCT2 gRNA target 4

<400> SEQUENCE: 37
tgcggtagca ggaactgagc                                                20

<210> SEQ ID NO 38
<211> LENGTH: 20
<212> TYPE: DNA
<213> ORGANISM: Artificial Sequence
<220> FEATURE:
<223> OTHER INFORMATION: OCT2 gRNA target 5

<400> SEQUENCE: 38
caggtgctta cctttgtact                                                20

<210> SEQ ID NO 39
<211> LENGTH: 20
<212> TYPE: DNA
<213> ORGANISM: Artificial Sequence
<220> FEATURE:
<223> OTHER INFORMATION: OCT2 gRNA target 6

<400> SEQUENCE: 39
ggagtccaga ccttgcttct                                                20

<210> SEQ ID NO 40
<211> LENGTH: 20
<212> TYPE: DNA
<213> ORGANISM: Artificial Sequence
<220> FEATURE:
<223> OTHER INFORMATION: PU.1 gRNA target 1

<400> SEQUENCE: 40
aatactcgtg cgtttggcgt                                                20

<210> SEQ ID NO 41
<211> LENGTH: 20
<212> TYPE: DNA

```
<213> ORGANISM: Artificial Sequence
<220> FEATURE:
<223> OTHER INFORMATION: PU.1 gRNA target 2

<400> SEQUENCE: 41
gctccgcagc ggcgacatga                                                    20

<210> SEQ ID NO 42
<211> LENGTH: 20
<212> TYPE: DNA
<213> ORGANISM: Artificial Sequence
<220> FEATURE:
<223> OTHER INFORMATION: PU.1 gRNA target 3

<400> SEQUENCE: 42
gtgtctgacg gcgaggcgga                                                    20

<210> SEQ ID NO 43
<211> LENGTH: 20
<212> TYPE: DNA
<213> ORGANISM: Artificial Sequence
<220> FEATURE:
<223> OTHER INFORMATION: PU.1 gRNA target 4

<400> SEQUENCE: 43
tctcgaactc gctgtgcacg                                                    20

<210> SEQ ID NO 44
<211> LENGTH: 20
<212> TYPE: DNA
<213> ORGANISM: Artificial Sequence
<220> FEATURE:
<223> OTHER INFORMATION: PU.1 gRNA target 5

<400> SEQUENCE: 44
ccagcacttc gccgctgaac                                                    20

<210> SEQ ID NO 45
<211> LENGTH: 20
<212> TYPE: DNA
<213> ORGANISM: Artificial Sequence
<220> FEATURE:
<223> OTHER INFORMATION: PU.1 gRNA target 6

<400> SEQUENCE: 45
gatccgtgtc atagggcacc                                                    20

<210> SEQ ID NO 46
<211> LENGTH: 20
<212> TYPE: DNA
<213> ORGANISM: Artificial Sequence
<220> FEATURE:
<223> OTHER INFORMATION: SPIB gRNA target 1

<400> SEQUENCE: 46
cggcaccacc atgctcgccc                                                    20

<210> SEQ ID NO 47
<211> LENGTH: 20
<212> TYPE: DNA
<213> ORGANISM: Artificial Sequence
<220> FEATURE:
<223> OTHER INFORMATION: SPIB gRNA target 2

<400> SEQUENCE: 47
cgggccacac ttcagctgtc                                                    20
```

```
<210> SEQ ID NO 48
<211> LENGTH: 20
<212> TYPE: DNA
<213> ORGANISM: Artificial Sequence
<220> FEATURE:
<223> OTHER INFORMATION: SPIB gRNA target 3

<400> SEQUENCE: 48
agatggcgtc ttctatgacc                                               20

<210> SEQ ID NO 49
<211> LENGTH: 20
<212> TYPE: DNA
<213> ORGANISM: Artificial Sequence
<220> FEATURE:
<223> OTHER INFORMATION: SPIB gRNA target 4

<400> SEQUENCE: 49
ctcaccagac agctgaagtg                                               20

<210> SEQ ID NO 50
<211> LENGTH: 20
<212> TYPE: DNA
<213> ORGANISM: Artificial Sequence
<220> FEATURE:
<223> OTHER INFORMATION: SPIB gRNA target 5

<400> SEQUENCE: 50
tcacttactg tgcagcctcc                                               20

<210> SEQ ID NO 51
<211> LENGTH: 20
<212> TYPE: DNA
<213> ORGANISM: Artificial Sequence
<220> FEATURE:
<223> OTHER INFORMATION: SPIB gRNA target 6

<400> SEQUENCE: 51
ccaggagccc cctctgaatc                                               20

<210> SEQ ID NO 52
<211> LENGTH: 20
<212> TYPE: DNA
<213> ORGANISM: Artificial Sequence
<220> FEATURE:
<223> OTHER INFORMATION: ETS1 gRNA target 1

<400> SEQUENCE: 52
gagagtcggc ttgagatcga                                               20

<210> SEQ ID NO 53
<211> LENGTH: 20
<212> TYPE: DNA
<213> ORGANISM: Artificial Sequence
<220> FEATURE:
<223> OTHER INFORMATION: ETS1 gRNA target 2

<400> SEQUENCE: 53
tggaaaccac agttcattcg                                               20

<210> SEQ ID NO 54
<211> LENGTH: 20
<212> TYPE: DNA
<213> ORGANISM: Artificial Sequence
<220> FEATURE:
```

```
<223> OTHER INFORMATION: ETS1 gRNA target 3

<400> SEQUENCE: 54
gaagatcctc gaatgaactg                                              20

<210> SEQ ID NO 55
<211> LENGTH: 20
<212> TYPE: DNA
<213> ORGANISM: Artificial Sequence
<220> FEATURE:
<223> OTHER INFORMATION: ETS1 gRNA target 4

<400> SEQUENCE: 55
gactctcacc atcatcaaga                                              20

<210> SEQ ID NO 56
<211> LENGTH: 20
<212> TYPE: DNA
<213> ORGANISM: Artificial Sequence
<220> FEATURE:
<223> OTHER INFORMATION: ETS1 gRNA target 5

<400> SEQUENCE: 56
cactaaagaa cagcaacgac                                              20

<210> SEQ ID NO 57
<211> LENGTH: 20
<212> TYPE: DNA
<213> ORGANISM: Artificial Sequence
<220> FEATURE:
<223> OTHER INFORMATION: ETS1 gRNA target 6

<400> SEQUENCE: 57
acgaggcgct gagtaaggga                                              20

<210> SEQ ID NO 58
<211> LENGTH: 20
<212> TYPE: DNA
<213> ORGANISM: Artificial Sequence
<220> FEATURE:
<223> OTHER INFORMATION: IRF8 gRNA target 1

<400> SEQUENCE: 58
acctgaatgg tgcgcgtcgt                                              20

<210> SEQ ID NO 59
<211> LENGTH: 20
<212> TYPE: DNA
<213> ORGANISM: Artificial Sequence
<220> FEATURE:
<223> OTHER INFORMATION: IRF8 gRNA target 2

<400> SEQUENCE: 59
acctacgacg cgcaccattc                                              20

<210> SEQ ID NO 60
<211> LENGTH: 20
<212> TYPE: DNA
<213> ORGANISM: Artificial Sequence
<220> FEATURE:
<223> OTHER INFORMATION: IRF8 gRNA target 3

<400> SEQUENCE: 60
gtggtcggcg gcttcgacag                                              20
```

```
<210> SEQ ID NO 61
<211> LENGTH: 20
<212> TYPE: DNA
<213> ORGANISM: Artificial Sequence
<220> FEATURE:
<223> OTHER INFORMATION: IRF8 gRNA target 4

<400> SEQUENCE: 61
gcgtaacctc gtcttccaag                                           20

<210> SEQ ID NO 62
<211> LENGTH: 20
<212> TYPE: DNA
<213> ORGANISM: Artificial Sequence
<220> FEATURE:
<223> OTHER INFORMATION: IRF8 gRNA target 5

<400> SEQUENCE: 62
cggaaatgtc cagttgggac                                           20

<210> SEQ ID NO 63
<211> LENGTH: 20
<212> TYPE: DNA
<213> ORGANISM: Artificial Sequence
<220> FEATURE:
<223> OTHER INFORMATION: IRF8 gRNA target 6

<400> SEQUENCE: 63
attgacagta gcatgtatcc                                           20

<210> SEQ ID NO 64
<211> LENGTH: 20
<212> TYPE: DNA
<213> ORGANISM: Artificial Sequence
<220> FEATURE:
<223> OTHER INFORMATION: IRF4 SAM gRNA 1

<400> SEQUENCE: 64
actttgcaag ccgagagccg                                           20

<210> SEQ ID NO 65
<211> LENGTH: 20
<212> TYPE: DNA
<213> ORGANISM: Artificial Sequence
<220> FEATURE:
<223> OTHER INFORMATION: IRF4 SAM gRNA 2

<400> SEQUENCE: 65
cgggaacccc accccggccg                                           20

<210> SEQ ID NO 66
<211> LENGTH: 20
<212> TYPE: DNA
<213> ORGANISM: Artificial Sequence
<220> FEATURE:
<223> OTHER INFORMATION: IRF4 SAM gRNA 3

<400> SEQUENCE: 66
gcagccccca gccttcacgc                                           20

<210> SEQ ID NO 67
<211> LENGTH: 20
<212> TYPE: DNA
<213> ORGANISM: Artificial Sequence
<220> FEATURE:
<223> OTHER INFORMATION: BLIMP1 SAM gRNA 1
```

```
<400> SEQUENCE: 67
atcttcttac ttccctttga                                               20

<210> SEQ ID NO 68
<211> LENGTH: 20
<212> TYPE: DNA
<213> ORGANISM: Artificial Sequence
<220> FEATURE:
<223> OTHER INFORMATION: BLIMP1 SAM gRNA 2

<400> SEQUENCE: 68
atgcgaagag aggaagctct                                               20

<210> SEQ ID NO 69
<211> LENGTH: 20
<212> TYPE: DNA
<213> ORGANISM: Artificial Sequence
<220> FEATURE:
<223> OTHER INFORMATION: BLIMP1 SAM gRNA 3

<400> SEQUENCE: 69
cggctgtgct agcaatctgg                                               20

<210> SEQ ID NO 70
<211> LENGTH: 20
<212> TYPE: DNA
<213> ORGANISM: Artificial Sequence
<220> FEATURE:
<223> OTHER INFORMATION: BLIMP1 SAM gRNA 4

<400> SEQUENCE: 70
acaagtgtta ctttaggact                                               20

<210> SEQ ID NO 71
<211> LENGTH: 20
<212> TYPE: DNA
<213> ORGANISM: Artificial Sequence
<220> FEATURE:
<223> OTHER INFORMATION: BLIMP1 SAM gRNA 5

<400> SEQUENCE: 71
cttggaacct tgcctttttg                                               20

<210> SEQ ID NO 72
<211> LENGTH: 20
<212> TYPE: DNA
<213> ORGANISM: Artificial Sequence
<220> FEATURE:
<223> OTHER INFORMATION: BLIMP1 SAM gRNA 6

<400> SEQUENCE: 72
ggaaacactg ggtggggcaa                                               20

<210> SEQ ID NO 73
<211> LENGTH: 20
<212> TYPE: DNA
<213> ORGANISM: Artificial Sequence
<220> FEATURE:
<223> OTHER INFORMATION: XBP1 SAM gRNA 1

<400> SEQUENCE: 73
aggaccgtgg ctatggagtc                                               20

<210> SEQ ID NO 74
<211> LENGTH: 20
```

```
<212> TYPE: DNA
<213> ORGANISM: Artificial Sequence
<220> FEATURE:
<223> OTHER INFORMATION: XBP1 SAM gRNA 2

<400> SEQUENCE: 74
gaccccaagt acctttggcc                                           20

<210> SEQ ID NO 75
<211> LENGTH: 20
<212> TYPE: DNA
<213> ORGANISM: Artificial Sequence
<220> FEATURE:
<223> OTHER INFORMATION: XBP1 SAM gRNA 3

<400> SEQUENCE: 75
ggcgtggcag cggcaatccc                                           20

<210> SEQ ID NO 76
<211> LENGTH: 19
<212> TYPE: PRT
<213> ORGANISM: Artificial Sequence
<220> FEATURE:
<223> OTHER INFORMATION: Ig HC signal peptide 1

<400> SEQUENCE: 76

Met Glu Phe Gly Leu Arg Trp Val Phe Leu Val Ala Ile Leu Lys Asp
1               5                   10                  15

Val Gln Cys

<210> SEQ ID NO 77
<211> LENGTH: 19
<212> TYPE: PRT
<213> ORGANISM: Artificial Sequence
<220> FEATURE:
<223> OTHER INFORMATION: Ig HC signal peptide 2

<400> SEQUENCE: 77

Met Glu Phe Gly Leu Ser Trp Val Phe Leu Val Ala Ile Leu Lys Gly
1               5                   10                  15

Val Gln Cys

<210> SEQ ID NO 78
<211> LENGTH: 19
<212> TYPE: PRT
<213> ORGANISM: Artificial Sequence
<220> FEATURE:
<223> OTHER INFORMATION: Ig HC signal peptide 3

<400> SEQUENCE: 78

Met Glu Leu Gly Leu Ser Trp Val Phe Leu Val Ala Ile Leu Lys Gly
1               5                   10                  15

Val Gln Cys

<210> SEQ ID NO 79
<211> LENGTH: 19
<212> TYPE: PRT
<213> ORGANISM: Artificial Sequence
<220> FEATURE:
<223> OTHER INFORMATION: Ig HC signal peptide 4

<400> SEQUENCE: 79

Met Glu Leu Gly Leu Arg Trp Val Phe Leu Val Ala Phe Leu Glu Gly
1               5                   10                  15
```

Val Gln Cys

```
<210> SEQ ID NO 80
<211> LENGTH: 19
<212> TYPE: PRT
<213> ORGANISM: Artificial Sequence
<220> FEATURE:
<223> OTHER INFORMATION: Ig HC signal peptide 5

<400> SEQUENCE: 80
```

Met Glu Leu Gly Leu Arg Trp Val Phe Leu Val Thr Phe Phe Trp Gly
1               5                   10                  15

Val Gln Cys

```
<210> SEQ ID NO 81
<211> LENGTH: 19
<212> TYPE: PRT
<213> ORGANISM: Artificial Sequence
<220> FEATURE:
<223> OTHER INFORMATION: Ig HC signal peptide 6

<400> SEQUENCE: 81
```

Met Glu Leu Gly Leu Arg Trp Val Leu Leu Val Ala Ile Leu Glu Gly
1               5                   10                  15

Val His Cys

```
<210> SEQ ID NO 82
<211> LENGTH: 19
<212> TYPE: PRT
<213> ORGANISM: Artificial Sequence
<220> FEATURE:
<223> OTHER INFORMATION: Ig HC signal peptide 7

<400> SEQUENCE: 82
```

Met Glu Leu Gly Leu Arg Trp Val Phe Leu Val Ala Leu Leu Glu Gly
1               5                   10                  15

Val His Cys

```
<210> SEQ ID NO 83
<211> LENGTH: 19
<212> TYPE: PRT
<213> ORGANISM: Artificial Sequence
<220> FEATURE:
<223> OTHER INFORMATION: Ig HC signal peptide 8

<400> SEQUENCE: 83
```

Met Glu Leu Gly Leu Arg Trp Val Phe Leu Ile Ala Thr Leu Ala Gly
1               5                   10                  15

Ala Arg Cys

```
<210> SEQ ID NO 84
<211> LENGTH: 19
<212> TYPE: PRT
<213> ORGANISM: Artificial Sequence
<220> FEATURE:
<223> OTHER INFORMATION: Ig HC signal peptide 9

<400> SEQUENCE: 84
```

Met Glu Leu Gly Leu Arg Trp Val Phe Leu Val Ala Ile Leu Glu Gly
1               5                   10                  15

Val Gln Cys

```
<210> SEQ ID NO 85
```

<211> LENGTH: 19
<212> TYPE: PRT
<213> ORGANISM: Artificial Sequence
<220> FEATURE:
<223> OTHER INFORMATION: Ig HC signal peptide 10

<400> SEQUENCE: 85

Met Glu Leu Gly Leu Tyr Trp Val Phe Leu Val Ala Ile Leu Glu Gly
1               5                   10                  15

Val Gln Cys

<210> SEQ ID NO 86
<211> LENGTH: 19
<212> TYPE: PRT
<213> ORGANISM: Artificial Sequence
<220> FEATURE:
<223> OTHER INFORMATION: Ig HC signal peptide 11

<400> SEQUENCE: 86

Met Asp Leu Gly Leu Tyr Trp Val Phe Leu Val Ala Ile Leu Glu Gly
1               5                   10                  15

Val Glu Cys

<210> SEQ ID NO 87
<211> LENGTH: 19
<212> TYPE: PRT
<213> ORGANISM: Artificial Sequence
<220> FEATURE:
<223> OTHER INFORMATION: Ig HC signal peptide 12

<400> SEQUENCE: 87

Met Glu Leu Gly Leu Cys Trp Val Phe Leu Val Ala Ile Leu Glu Gly
1               5                   10                  15

Val Pro Cys

<210> SEQ ID NO 88
<211> LENGTH: 19
<212> TYPE: PRT
<213> ORGANISM: Artificial Sequence
<220> FEATURE:
<223> OTHER INFORMATION: Ig HC signal peptide 13

<400> SEQUENCE: 88

Met Glu Leu Gly Leu Cys Trp Val Phe Leu Val Ala Ile Leu Glu Gly
1               5                   10                  15

Val Gln Cys

<210> SEQ ID NO 89
<211> LENGTH: 19
<212> TYPE: PRT
<213> ORGANISM: Artificial Sequence
<220> FEATURE:
<223> OTHER INFORMATION: Ig HC signal peptide 14

<400> SEQUENCE: 89

Met Glu Leu Gly Leu Asn Trp Val Leu Leu Val Ala Ile Leu Glu Gly
1               5                   10                  15

Val Gln Cys

<210> SEQ ID NO 90
<211> LENGTH: 19
<212> TYPE: PRT
<213> ORGANISM: Artificial Sequence
<220> FEATURE:

<223> OTHER INFORMATION: Ig HC signal peptide 15

<400> SEQUENCE: 90

Met Glu Leu Gly Leu Ser Trp Val Phe Leu Val Ala Ile Leu Glu Gly
1               5                   10                  15

Val His Cys

<210> SEQ ID NO 91
<211> LENGTH: 19
<212> TYPE: PRT
<213> ORGANISM: Artificial Sequence
<220> FEATURE:
<223> OTHER INFORMATION: Ig HC signal peptide 16

<400> SEQUENCE: 91

Met Glu Leu Gly Leu Ser Trp Val Phe Leu Val Ala Ile Leu Glu Gly
1               5                   10                  15

Val Gln Cys

<210> SEQ ID NO 92
<211> LENGTH: 19
<212> TYPE: PRT
<213> ORGANISM: Artificial Sequence
<220> FEATURE:
<223> OTHER INFORMATION: Ig HC signal peptide 17

<400> SEQUENCE: 92

Met Glu Leu Gly Leu Ser Trp Val Phe Leu Val Val Ile Leu Glu Gly
1               5                   10                  15

Val Gln Cys

<210> SEQ ID NO 93
<211> LENGTH: 19
<212> TYPE: PRT
<213> ORGANISM: Artificial Sequence
<220> FEATURE:
<223> OTHER INFORMATION: Ig HC signal peptide 18

<400> SEQUENCE: 93

Met Glu Ser Gly Leu Thr Trp Leu Phe Leu Val Ala Ile Leu Lys Gly
1               5                   10                  15

Val His Cys

<210> SEQ ID NO 94
<211> LENGTH: 19
<212> TYPE: PRT
<213> ORGANISM: Artificial Sequence
<220> FEATURE:
<223> OTHER INFORMATION: Ig HC signal peptide 19

<400> SEQUENCE: 94

Met Lys His Leu Trp Phe Phe Leu Leu Leu Val Ala Ala Pro Arg Trp
1               5                   10                  15

Val Leu Ser

<210> SEQ ID NO 95
<211> LENGTH: 19
<212> TYPE: PRT
<213> ORGANISM: Artificial Sequence
<220> FEATURE:
<223> OTHER INFORMATION: Ig HC signal peptide 20

<400> SEQUENCE: 95

```
Met Lys His Leu Trp Phe Phe Leu Leu Leu Val Ala Pro Pro Arg Trp
1               5                   10                  15

Val Leu Ser
```

<210> SEQ ID NO 96
<211> LENGTH: 19
<212> TYPE: PRT
<213> ORGANISM: Artificial Sequence
<220> FEATURE:
<223> OTHER INFORMATION: Ig HC signal peptide 21

<400> SEQUENCE: 96

```
Met Lys His Leu Trp Phe Phe Leu Leu Leu Val Ala Thr Pro Arg Trp
1               5                   10                  15

Val Leu Ser
```

<210> SEQ ID NO 97
<211> LENGTH: 19
<212> TYPE: PRT
<213> ORGANISM: Artificial Sequence
<220> FEATURE:
<223> OTHER INFORMATION: Ig HC signal peptide 22

<400> SEQUENCE: 97

```
Met Arg His Leu Trp Phe Phe Leu Leu Leu Val Ala Ala Pro Arg Trp
1               5                   10                  15

Val Leu Ser
```

<210> SEQ ID NO 98
<211> LENGTH: 19
<212> TYPE: PRT
<213> ORGANISM: Artificial Sequence
<220> FEATURE:
<223> OTHER INFORMATION: Ig HC signal peptide 23

<400> SEQUENCE: 98

```
Met Lys His Leu Trp Phe Phe Phe Leu Leu Val Ala Ala Pro Arg Ser
1               5                   10                  15

Val Leu Ser
```

<210> SEQ ID NO 99
<211> LENGTH: 20
<212> TYPE: PRT
<213> ORGANISM: Artificial Sequence
<220> FEATURE:
<223> OTHER INFORMATION: Ig HC signal peptide 24

<400> SEQUENCE: 99

```
Met Ser Val Ser Phe Leu Ile Phe Leu Pro Val Leu Gly Leu Pro Trp
1               5                   10                  15

Gly Val Leu Ser
            20
```

<210> SEQ ID NO 100
<211> LENGTH: 19
<212> TYPE: PRT
<213> ORGANISM: Artificial Sequence
<220> FEATURE:
<223> OTHER INFORMATION: Ig HC signal peptide 25

<400> SEQUENCE: 100

```
Met Gly His Pro Trp Phe Phe Leu Leu Leu Val Thr Ala Pro Arg Trp
1               5                   10                  15
```

Val Leu Ser

<210> SEQ ID NO 101
<211> LENGTH: 19
<212> TYPE: PRT
<213> ORGANISM: Artificial Sequence
<220> FEATURE:
<223> OTHER INFORMATION: Ig HC signal peptide 26

<400> SEQUENCE: 101

Met Asp Trp Thr Trp Arg Ile Leu Phe Leu Val Ala Ala Ala Thr Gly
1               5                   10                  15

Ala His Ser

<210> SEQ ID NO 102
<211> LENGTH: 19
<212> TYPE: PRT
<213> ORGANISM: Artificial Sequence
<220> FEATURE:
<223> OTHER INFORMATION: Ig HC signal peptide 27

<400> SEQUENCE: 102

Met Asp Trp Thr Trp Arg Ile Leu Phe Leu Val Ala Ala Ala Thr Asp
1               5                   10                  15

Ala Tyr Ser

<210> SEQ ID NO 103
<211> LENGTH: 19
<212> TYPE: PRT
<213> ORGANISM: Artificial Sequence
<220> FEATURE:
<223> OTHER INFORMATION: Ig HC signal peptide 28

<400> SEQUENCE: 103

Met Asp Trp Thr Trp Arg Ile Leu Phe Leu Val Ala Ala Ala Thr Ser
1               5                   10                  15

Ala His Ser

<210> SEQ ID NO 104
<211> LENGTH: 19
<212> TYPE: PRT
<213> ORGANISM: Artificial Sequence
<220> FEATURE:
<223> OTHER INFORMATION: Ig HC signal peptide 29

<400> SEQUENCE: 104

Met Asp Trp Thr Trp Arg Ile Leu Phe Leu Val Ala Ala Ala Thr Glu
1               5                   10                  15

Ala His Ser

<210> SEQ ID NO 105
<211> LENGTH: 19
<212> TYPE: PRT
<213> ORGANISM: Artificial Sequence
<220> FEATURE:
<223> OTHER INFORMATION: Ig HC signal peptide 30

<400> SEQUENCE: 105

Met Asp Trp Thr Trp Arg Ile Leu Phe Leu Val Thr Ala Ala Thr Gly
1               5                   10                  15

Ala His Ser

<210> SEQ ID NO 106

```
<211> LENGTH: 19
<212> TYPE: PRT
<213> ORGANISM: Artificial Sequence
<220> FEATURE:
<223> OTHER INFORMATION: Ig HC signal peptide 31

<400> SEQUENCE: 106

Met Asp Trp Thr Trp Arg Leu Leu Phe Leu Val Ala Ala Val Thr Ser
1               5                   10                  15

Ala His Ser

<210> SEQ ID NO 107
<211> LENGTH: 19
<212> TYPE: PRT
<213> ORGANISM: Artificial Sequence
<220> FEATURE:
<223> OTHER INFORMATION: Ig HC signal peptide 32

<400> SEQUENCE: 107

Met Asp Trp Thr Trp Ser Ile Leu Phe Leu Val Ala Ala Ala Thr Gly
1               5                   10                  15

Ala His Ser

<210> SEQ ID NO 108
<211> LENGTH: 19
<212> TYPE: PRT
<213> ORGANISM: Artificial Sequence
<220> FEATURE:
<223> OTHER INFORMATION: Ig HC signal peptide 33

<400> SEQUENCE: 108

Met Asp Trp Thr Trp Ser Ile Leu Phe Leu Val Thr Ala Ala Thr Gly
1               5                   10                  15

Ala His Ser

<210> SEQ ID NO 109
<211> LENGTH: 19
<212> TYPE: PRT
<213> ORGANISM: Artificial Sequence
<220> FEATURE:
<223> OTHER INFORMATION: Ig HC signal peptide 34

<400> SEQUENCE: 109

Met Asp Trp Thr Trp Ser Ile Leu Phe Leu Val Ala Gly Ala Ser Gly
1               5                   10                  15

Ala His Ser

<210> SEQ ID NO 110
<211> LENGTH: 19
<212> TYPE: PRT
<213> ORGANISM: Artificial Sequence
<220> FEATURE:
<223> OTHER INFORMATION: Ig HC signal peptide 35

<400> SEQUENCE: 110

Met Asp Trp Thr Trp Ser Ile Leu Phe Leu Val Ala Ala Ala Thr Gly
1               5                   10                  15

Ala Arg Pro

<210> SEQ ID NO 111
<211> LENGTH: 19
<212> TYPE: PRT
<213> ORGANISM: Artificial Sequence
<220> FEATURE:
```

<223> OTHER INFORMATION: Ig HC signal peptide 36

<400> SEQUENCE: 111

Met Gly Trp Thr Trp Ser Ile Leu Phe Leu Val Ala Ala Thr Thr Gly
1               5                   10                  15

Ala Pro Ser

<210> SEQ ID NO 112
<211> LENGTH: 19
<212> TYPE: PRT
<213> ORGANISM: Artificial Sequence
<220> FEATURE:
<223> OTHER INFORMATION: Ig HC signal peptide 37

<400> SEQUENCE: 112

Met Asp Trp Thr Trp Ser Ile Leu Phe Leu Val Ala Ala Ala Thr Gly
1               5                   10                  15

Ala Gln Ser

<210> SEQ ID NO 113
<211> LENGTH: 19
<212> TYPE: PRT
<213> ORGANISM: Artificial Sequence
<220> FEATURE:
<223> OTHER INFORMATION: Ig HC signal peptide 38

<400> SEQUENCE: 113

Met Asp Trp Ala Trp Arg Ile Leu Phe Leu Val Ala Ala Ala Thr Gly
1               5                   10                  15

Val His Ser

<210> SEQ ID NO 114
<211> LENGTH: 19
<212> TYPE: PRT
<213> ORGANISM: Artificial Sequence
<220> FEATURE:
<223> OTHER INFORMATION: Ig HC signal peptide 39

<400> SEQUENCE: 114

Met Asp Cys Thr Trp Arg Ile Leu Leu Leu Val Ala Val Ala Thr Gly
1               5                   10                  15

Thr His Ala

<210> SEQ ID NO 115
<211> LENGTH: 19
<212> TYPE: PRT
<213> ORGANISM: Artificial Sequence
<220> FEATURE:
<223> OTHER INFORMATION: Ig HC signal peptide 40

<400> SEQUENCE: 115

Met Asp Cys Thr Trp Arg Ile Leu Leu Leu Val Ala Ala Ala Thr Gly
1               5                   10                  15

Thr His Ala

<210> SEQ ID NO 116
<211> LENGTH: 19
<212> TYPE: PRT
<213> ORGANISM: Artificial Sequence
<220> FEATURE:
<223> OTHER INFORMATION: Ig HC signal peptide 41

<400> SEQUENCE: 116

```
Met Asp Trp Thr Trp Arg Ile Leu Phe Leu Ala Ala Ala Thr Gly
1               5                   10                  15

Val Gln Ser

<210> SEQ ID NO 117
<211> LENGTH: 19
<212> TYPE: PRT
<213> ORGANISM: Artificial Sequence
<220> FEATURE:
<223> OTHER INFORMATION: Ig HC signal peptide 42

<400> SEQUENCE: 117

Met Asp Trp Thr Trp Thr Ile Leu Phe Leu Val Ala Gly Ala Thr Gly
1               5                   10                  15

Val Lys Ser

<210> SEQ ID NO 118
<211> LENGTH: 19
<212> TYPE: PRT
<213> ORGANISM: Artificial Sequence
<220> FEATURE:
<223> OTHER INFORMATION: Ig HC signal peptide 43

<400> SEQUENCE: 118

Met Asp Trp Thr Trp Ser Ile Leu Phe Leu Val Ala Ala Ala Thr Gly
1               5                   10                  15

Val His Ser

<210> SEQ ID NO 119
<211> LENGTH: 19
<212> TYPE: PRT
<213> ORGANISM: Artificial Sequence
<220> FEATURE:
<223> OTHER INFORMATION: Ig HC signal peptide 44

<400> SEQUENCE: 119

Met Asp Trp Thr Trp Arg Phe Leu Phe Val Val Ala Ala Val Thr Gly
1               5                   10                  15

Val Gln Ser

<210> SEQ ID NO 120
<211> LENGTH: 18
<212> TYPE: PRT
<213> ORGANISM: Artificial Sequence
<220> FEATURE:
<223> OTHER INFORMATION: Ig HC signal peptide 45

<400> SEQUENCE: 120

Met Asp Trp Thr Trp Ile Leu Phe Leu Val Ala Ala Ala Thr Arg Val
1               5                   10                  15

His Ser

<210> SEQ ID NO 121
<211> LENGTH: 19
<212> TYPE: PRT
<213> ORGANISM: Artificial Sequence
<220> FEATURE:
<223> OTHER INFORMATION: Ig HC signal peptide 46

<400> SEQUENCE: 121

Met Asp Trp Thr Trp Arg Phe Leu Leu Val Val Ala Ala Ala Thr Gly
1               5                   10                  15

Val Pro Ser
```

<210> SEQ ID NO 122
<211> LENGTH: 19
<212> TYPE: PRT
<213> ORGANISM: Artificial Sequence
<220> FEATURE:
<223> OTHER INFORMATION: Ig HC signal peptide 47

<400> SEQUENCE: 122

Met Asp Trp Thr Trp Arg Phe Leu Ile Val Val Ala Ala Ala Thr Gly
1               5                   10                  15

Val Gln Ser

<210> SEQ ID NO 123
<211> LENGTH: 19
<212> TYPE: PRT
<213> ORGANISM: Artificial Sequence
<220> FEATURE:
<223> OTHER INFORMATION: Ig HC signal peptide 48

<400> SEQUENCE: 123

Met Asp Trp Thr Trp Arg Phe Leu Phe Val Val Ala Ala Ala Thr Ser
1               5                   10                  15

Val Gln Ser

<210> SEQ ID NO 124
<211> LENGTH: 19
<212> TYPE: PRT
<213> ORGANISM: Artificial Sequence
<220> FEATURE:
<223> OTHER INFORMATION: Ig HC signal peptide 49

<400> SEQUENCE: 124

Met Asp Trp Thr Trp Arg Phe Leu Phe Val Val Ala Ala Ala Thr Gly
1               5                   10                  15

Val Gln Ser

<210> SEQ ID NO 125
<211> LENGTH: 19
<212> TYPE: PRT
<213> ORGANISM: Artificial Sequence
<220> FEATURE:
<223> OTHER INFORMATION: Ig HC signal peptide 50

<400> SEQUENCE: 125

Met Asp Trp Thr Trp Arg Phe Leu Phe Val Val Ala Ala Gly Thr Gly
1               5                   10                  15

Val Gln Ser

<210> SEQ ID NO 126
<211> LENGTH: 19
<212> TYPE: PRT
<213> ORGANISM: Artificial Sequence
<220> FEATURE:
<223> OTHER INFORMATION: Ig HC signal peptide 51

<400> SEQUENCE: 126

Met Asp Trp Thr Trp Arg Phe Leu Phe Val Val Ala Ala Ser Thr Gly
1               5                   10                  15

Val Gln Ser

<210> SEQ ID NO 127
<211> LENGTH: 19

-continued

```
<212> TYPE: PRT
<213> ORGANISM: Artificial Sequence
<220> FEATURE:
<223> OTHER INFORMATION: Ig HC signal peptide 52

<400> SEQUENCE: 127

Met Asp Trp Thr Trp Arg Val Leu Phe Val Val Ala Ala Ser Thr Gly
1               5                   10                  15

Val Gln Ser

<210> SEQ ID NO 128
<211> LENGTH: 19
<212> TYPE: PRT
<213> ORGANISM: Artificial Sequence
<220> FEATURE:
<223> OTHER INFORMATION: Ig HC signal peptide 53

<400> SEQUENCE: 128

Met Asp Arg Thr Trp Arg Leu Leu Phe Val Val Ala Ala Ala Thr Gly
1               5                   10                  15

Val Gln Ser

<210> SEQ ID NO 129
<211> LENGTH: 19
<212> TYPE: PRT
<213> ORGANISM: Artificial Sequence
<220> FEATURE:
<223> OTHER INFORMATION: Ig HC signal peptide 54

<400> SEQUENCE: 129

Met Asp Trp Thr Trp Arg Phe Leu Phe Val Val Ala Ala Ala Ala Gly
1               5                   10                  15

Val Gln Ser

<210> SEQ ID NO 130
<211> LENGTH: 19
<212> TYPE: PRT
<213> ORGANISM: Artificial Sequence
<220> FEATURE:
<223> OTHER INFORMATION: Ig HC signal peptide 55

<400> SEQUENCE: 130

Met Gly Trp Thr Trp Arg Phe Leu Phe Val Val Ala Ala Ala Ala Gly
1               5                   10                  15

Val Gln Ser

<210> SEQ ID NO 131
<211> LENGTH: 19
<212> TYPE: PRT
<213> ORGANISM: Artificial Sequence
<220> FEATURE:
<223> OTHER INFORMATION: Ig HC signal peptide 56

<400> SEQUENCE: 131

Met Asp Trp Thr Trp Thr Phe Leu Phe Val Val Ala Ala Ala Thr Gly
1               5                   10                  15

Val Gln Ser

<210> SEQ ID NO 132
<211> LENGTH: 19
<212> TYPE: PRT
<213> ORGANISM: Artificial Sequence
<220> FEATURE:
<223> OTHER INFORMATION: Ig HC signal peptide 57
```

```
<400> SEQUENCE: 132

Met Asp Trp Thr Trp Arg Val Phe Cys Leu Leu Ala Val Ala Pro Gly
1               5                   10                  15

Val Gln Ser

<210> SEQ ID NO 133
<211> LENGTH: 19
<212> TYPE: PRT
<213> ORGANISM: Artificial Sequence
<220> FEATURE:
<223> OTHER INFORMATION: Ig HC signal peptide 58

<400> SEQUENCE: 133

Met Asp Trp Thr Trp Arg Val Phe Cys Leu Leu Ala Val Ala Pro Gly
1               5                   10                  15

Ala Asp Ser

<210> SEQ ID NO 134
<211> LENGTH: 19
<212> TYPE: PRT
<213> ORGANISM: Artificial Sequence
<220> FEATURE:
<223> OTHER INFORMATION: Ig HC signal peptide 59

<400> SEQUENCE: 134

Met Asp Trp Thr Trp Arg Val Phe Cys Leu Leu Ala Val Ala Pro Gly
1               5                   10                  15

Ala Asn Ser

<210> SEQ ID NO 135
<211> LENGTH: 19
<212> TYPE: PRT
<213> ORGANISM: Artificial Sequence
<220> FEATURE:
<223> OTHER INFORMATION: Ig HC signal peptide 60

<400> SEQUENCE: 135

Met Asp Trp Thr Trp Arg Val Phe Cys Leu Leu Ala Val Ala Pro Gly
1               5                   10                  15

Ala His Ser

<210> SEQ ID NO 136
<211> LENGTH: 19
<212> TYPE: PRT
<213> ORGANISM: Artificial Sequence
<220> FEATURE:
<223> OTHER INFORMATION: Ig HC signal peptide 61

<400> SEQUENCE: 136

Met Asp Trp Thr Trp Arg Val Phe Cys Leu Leu Ala Val Ile Ser Gly
1               5                   10                  15

Gly Gln Ser

<210> SEQ ID NO 137
<211> LENGTH: 19
<212> TYPE: PRT
<213> ORGANISM: Artificial Sequence
<220> FEATURE:
<223> OTHER INFORMATION: Ig HC signal peptide 62

<400> SEQUENCE: 137

Met Asp Trp Thr Trp Arg Phe Leu Phe Val Val Ala Val Ala Ile Gly
```

<210> SEQ ID NO 138
<211> LENGTH: 26
<212> TYPE: PRT
<213> ORGANISM: Artificial Sequence
<220> FEATURE:
<223> OTHER INFORMATION: Ig HC signal peptide 63

<400> SEQUENCE: 138

Met Asp Leu Met Cys Lys Lys Met Lys His Leu Trp Phe Phe Leu Leu
1               5                   10                  15

Leu Val Ala Ala Pro Arg Trp Val Leu Ser
            20                  25

<210> SEQ ID NO 139
<211> LENGTH: 26
<212> TYPE: PRT
<213> ORGANISM: Artificial Sequence
<220> FEATURE:
<223> OTHER INFORMATION: Ig HC signal peptide 64

<400> SEQUENCE: 139

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 140
<211> LENGTH: 26
<212> TYPE: PRT
<213> ORGANISM: Artificial Sequence
<220> FEATURE:
<223> OTHER INFORMATION: Ig HC signal peptide 65

<400> SEQUENCE: 140

Met Gly Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 141
<211> LENGTH: 26
<212> TYPE: PRT
<213> ORGANISM: Artificial Sequence
<220> FEATURE:
<223> OTHER INFORMATION: Ig HC signal peptide 66

<400> SEQUENCE: 141

Met Asp Leu Leu His Lys Asn Met Lys His Leu Trp Phe Phe Leu Leu
1               5                   10                  15

Leu Val Ala Ala Pro Arg Trp Gly Leu Ser
            20                  25

<210> SEQ ID NO 142
<211> LENGTH: 26
<212> TYPE: PRT
<213> ORGANISM: Artificial Sequence
<220> FEATURE:
<223> OTHER INFORMATION: Ig HC signal peptide 67

<400> SEQUENCE: 142

Met Asp Val Met Cys Lys Lys Met Lys His Leu Trp Phe Phe Leu Leu

```
                1               5                  10                  15
Leu Val Ala Ala Pro Arg Trp Val Leu Ala
            20                  25

<210> SEQ ID NO 143
<211> LENGTH: 26
<212> TYPE: PRT
<213> ORGANISM: Artificial Sequence
<220> FEATURE:
<223> OTHER INFORMATION: Ig HC signal peptide 68

<400> SEQUENCE: 143

Met Asp Leu Lys Cys Lys Lys Met Lys Arg Leu Trp Leu Phe Leu Leu
1               5                  10                  15

Leu Val Ala Ala Pro Arg Trp Val Leu Ser
            20                  25

<210> SEQ ID NO 144
<211> LENGTH: 26
<212> TYPE: PRT
<213> ORGANISM: Artificial Sequence
<220> FEATURE:
<223> OTHER INFORMATION: Ig HC signal peptide 69

<400> SEQUENCE: 144

Met Asp Leu Leu Cys Lys Asn Met Lys His Leu Trp Phe Phe Leu Leu
1               5                  10                  15

Leu Val Ala Ala Pro Arg Trp Val Leu Ser
            20                  25

<210> SEQ ID NO 145
<211> LENGTH: 26
<212> TYPE: PRT
<213> ORGANISM: Artificial Sequence
<220> FEATURE:
<223> OTHER INFORMATION: Ig HC signal peptide 70

<400> SEQUENCE: 145

Met Asp Leu Leu Cys Lys Lys Met Lys His Leu Trp Phe Phe Leu Leu
1               5                  10                  15

Leu Val Ala Ala Pro Arg Trp Val Leu Ser
            20                  25

<210> SEQ ID NO 146
<211> LENGTH: 26
<212> TYPE: PRT
<213> ORGANISM: Artificial Sequence
<220> FEATURE:
<223> OTHER INFORMATION: Ig HC signal peptide 71

<400> SEQUENCE: 146

Met Glu Leu Met Cys Lys Lys Met Lys His Leu Trp Phe Phe Leu Leu
1               5                  10                  15

Leu Val Ala Ala Pro Arg Trp Val Leu Ser
            20                  25

<210> SEQ ID NO 147
<211> LENGTH: 26
<212> TYPE: PRT
<213> ORGANISM: Artificial Sequence
<220> FEATURE:
<223> OTHER INFORMATION: Ig HC signal peptide 72

<400> SEQUENCE: 147
```

Met Asp Leu Met Cys Lys Lys Met Lys His Leu Trp Phe Phe Leu Leu
1               5                   10                  15

Leu Val Ala Ala Pro Gly Trp Val Leu Ser
            20                  25

<210> SEQ ID NO 148
<211> LENGTH: 23
<212> TYPE: PRT
<213> ORGANISM: Artificial Sequence
<220> FEATURE:
<223> OTHER INFORMATION: Ig HC signal peptide 73

<400> SEQUENCE: 148

Met Cys Lys Thr Met Lys Gln Leu Trp Phe Phe Leu Leu Leu Val Ala
1               5                   10                  15

Ala Pro Arg Trp Val Leu Ser
            20

<210> SEQ ID NO 149
<211> LENGTH: 27
<212> TYPE: PRT
<213> ORGANISM: Artificial Sequence
<220> FEATURE:
<223> OTHER INFORMATION: Ig HC signal peptide 74

<400> SEQUENCE: 149

Met Ala Lys Thr Asn Leu Phe Leu Phe Leu Ile Phe Ser Leu Leu Leu
1               5                   10                  15

Ser Leu Ser Ser Ala Ala Gln Pro Ala Met Ala
            20                  25

<210> SEQ ID NO 150
<211> LENGTH: 19
<212> TYPE: PRT
<213> ORGANISM: Artificial Sequence
<220> FEATURE:
<223> OTHER INFORMATION: Ig HC signal peptide 75

<400> SEQUENCE: 150

Met Asp Thr Leu Cys Ser Thr Leu Leu Leu Leu Thr Ile Pro Ser Trp
1               5                   10                  15

Val Leu Ser

<210> SEQ ID NO 151
<211> LENGTH: 19
<212> TYPE: PRT
<213> ORGANISM: Artificial Sequence
<220> FEATURE:
<223> OTHER INFORMATION: Ig HC signal peptide 76

<400> SEQUENCE: 151

Met Gly Ser Thr Ala Ile Leu Ala Leu Leu Leu Ala Val Leu Gln Gly
1               5                   10                  15

Val Cys Ala

<210> SEQ ID NO 152
<211> LENGTH: 19
<212> TYPE: PRT
<213> ORGANISM: Artificial Sequence
<220> FEATURE:
<223> OTHER INFORMATION: Ig HC signal peptide 77

<400> SEQUENCE: 152

Met Glu Leu Ser Leu Ser Trp Phe Phe Leu Leu Thr Ile Ile Gln Gly

```
1               5                   10                  15

Val Gln Cys

<210> SEQ ID NO 153
<211> LENGTH: 19
<212> TYPE: PRT
<213> ORGANISM: Artificial Sequence
<220> FEATURE:
<223> OTHER INFORMATION: Ig HC signal peptide 78

<400> SEQUENCE: 153

Met Glu Leu Gly Leu Ser Trp Ile Phe Leu Leu Ala Ile Leu Lys Gly
1               5                   10                  15

Val Gln Cys

<210> SEQ ID NO 154
<211> LENGTH: 19
<212> TYPE: PRT
<213> ORGANISM: Artificial Sequence
<220> FEATURE:
<223> OTHER INFORMATION: Ig HC signal peptide 79

<400> SEQUENCE: 154

Met Asp Leu Gly Leu Ser Trp Ile Phe Leu Leu Thr Ile Leu Lys Gly
1               5                   10                  15

Val Gln Cys

<210> SEQ ID NO 155
<211> LENGTH: 19
<212> TYPE: PRT
<213> ORGANISM: Artificial Sequence
<220> FEATURE:
<223> OTHER INFORMATION: Ig HC signal peptide 80

<400> SEQUENCE: 155

Met Glu Leu Gly Leu Thr Trp Ile Phe Leu Leu Ala Ile Leu Lys Gly
1               5                   10                  15

Val Gln Cys

<210> SEQ ID NO 156
<211> LENGTH: 19
<212> TYPE: PRT
<213> ORGANISM: Artificial Sequence
<220> FEATURE:
<223> OTHER INFORMATION: Ig HC signal peptide 81

<400> SEQUENCE: 156

Met Glu Leu Gly Leu Ser Trp Ile Phe Leu Val Ala Ile Leu Lys Gly
1               5                   10                  15

Val Gln Cys

<210> SEQ ID NO 157
<211> LENGTH: 19
<212> TYPE: PRT
<213> ORGANISM: Artificial Sequence
<220> FEATURE:
<223> OTHER INFORMATION: Ig HC signal peptide 82

<400> SEQUENCE: 157

Met Asp Leu Gly Leu Ser Trp Leu Phe Leu Val Ala Leu Leu Lys Gly
1               5                   10                  15

Val Gln Cys
```

<210> SEQ ID NO 158
<211> LENGTH: 19
<212> TYPE: PRT
<213> ORGANISM: Artificial Sequence
<220> FEATURE:
<223> OTHER INFORMATION: Ig HC signal peptide 83

<400> SEQUENCE: 158

Met Glu Phe Gly Leu Ser Cys Val Phe Leu Val Ala Ile Phe Lys Gly
1               5                   10                  15

Val His Cys

<210> SEQ ID NO 159
<211> LENGTH: 19
<212> TYPE: PRT
<213> ORGANISM: Artificial Sequence
<220> FEATURE:
<223> OTHER INFORMATION: Ig HC signal peptide 84

<400> SEQUENCE: 159

Met Glu Phe Gly Leu Ser Cys Leu Phe Leu Val Ala Ile Leu Lys Gly
1               5                   10                  15

Val Arg Cys

<210> SEQ ID NO 160
<211> LENGTH: 19
<212> TYPE: PRT
<213> ORGANISM: Artificial Sequence
<220> FEATURE:
<223> OTHER INFORMATION: Ig HC signal peptide 85

<400> SEQUENCE: 160

Met Glu Phe Gly Leu Ser Trp Ile Phe Leu Val Val Ile Ile Lys Gly
1               5                   10                  15

Val Gln Cys

<210> SEQ ID NO 161
<211> LENGTH: 19
<212> TYPE: PRT
<213> ORGANISM: Artificial Sequence
<220> FEATURE:
<223> OTHER INFORMATION: Ig HC signal peptide 86

<400> SEQUENCE: 161

Met Glu Phe Gly Leu Ser Trp Ile Phe Leu Val Val Ile Leu Lys Gly
1               5                   10                  15

Val Gln Cys

<210> SEQ ID NO 162
<211> LENGTH: 19
<212> TYPE: PRT
<213> ORGANISM: Artificial Sequence
<220> FEATURE:
<223> OTHER INFORMATION: Ig HC signal peptide 87

<400> SEQUENCE: 162

Met Glu Phe Gly Leu Ser Trp Ile Phe Leu Ala Thr Ile Leu Lys Gly
1               5                   10                  15

Val Gln Cys

<210> SEQ ID NO 163
<211> LENGTH: 19
<212> TYPE: PRT

```
<213> ORGANISM: Artificial Sequence
<220> FEATURE:
<223> OTHER INFORMATION: Ig HC signal peptide 88

<400> SEQUENCE: 163

Met Glu Phe Gly Leu Ser Trp Ile Phe Leu Ala Ala Ile Leu Lys Gly
1               5                   10                  15

Val Gln Cys

<210> SEQ ID NO 164
<211> LENGTH: 19
<212> TYPE: PRT
<213> ORGANISM: Artificial Sequence
<220> FEATURE:
<223> OTHER INFORMATION: Ig HC signal peptide 89

<400> SEQUENCE: 164

Met Glu Phe Gly Leu Ser Trp Ile Phe Leu Ala Ala Ile Leu Lys Gly
1               5                   10                  15

Val Gln Gly

<210> SEQ ID NO 165
<211> LENGTH: 19
<212> TYPE: PRT
<213> ORGANISM: Artificial Sequence
<220> FEATURE:
<223> OTHER INFORMATION: Ig HC signal peptide 90

<400> SEQUENCE: 165

Met Lys Phe Gly Leu Ser Trp Ile Phe Leu Pro Ala Ile Leu Lys Gly
1               5                   10                  15

Val Gln Cys

<210> SEQ ID NO 166
<211> LENGTH: 19
<212> TYPE: PRT
<213> ORGANISM: Artificial Sequence
<220> FEATURE:
<223> OTHER INFORMATION: Ig HC signal peptide 91

<400> SEQUENCE: 166

Met Glu Phe Gly Leu Ser Trp Leu Phe Leu Val Ala Ile Leu Lys Gly
1               5                   10                  15

Val Gln Cys

<210> SEQ ID NO 167
<211> LENGTH: 19
<212> TYPE: PRT
<213> ORGANISM: Artificial Sequence
<220> FEATURE:
<223> OTHER INFORMATION: Ig HC signal peptide 92

<400> SEQUENCE: 167

Met Glu Phe Gly Leu Ser Trp Leu Leu Leu Val Ala Ile Leu Lys Gly
1               5                   10                  15

Val Gln Cys

<210> SEQ ID NO 168
<211> LENGTH: 19
<212> TYPE: PRT
<213> ORGANISM: Artificial Sequence
<220> FEATURE:
<223> OTHER INFORMATION: Ig HC signal peptide 93
```

```
<400> SEQUENCE: 168

Met Glu Phe Gly Leu Ser Trp Leu Phe Leu Val Thr Ile Leu Lys Gly
1               5                   10                  15

Val Gln Cys

<210> SEQ ID NO 169
<211> LENGTH: 21
<212> TYPE: PRT
<213> ORGANISM: Artificial Sequence
<220> FEATURE:
<223> OTHER INFORMATION: Ig HC signal peptide 94

<400> SEQUENCE: 169

Met Glu Phe Gly Leu Ser Trp Val Phe Leu Val Ala Ile Ile Lys Gly
1               5                   10                  15

Val Gln Cys Gln Val
            20

<210> SEQ ID NO 170
<211> LENGTH: 19
<212> TYPE: PRT
<213> ORGANISM: Artificial Sequence
<220> FEATURE:
<223> OTHER INFORMATION: Ig HC signal peptide 95

<400> SEQUENCE: 170

Met Glu Phe Gly Leu Ser Trp Val Phe Leu Val Ala Ile Ile Lys Gly
1               5                   10                  15

Val Gln Cys

<210> SEQ ID NO 171
<211> LENGTH: 19
<212> TYPE: PRT
<213> ORGANISM: Artificial Sequence
<220> FEATURE:
<223> OTHER INFORMATION: Ig HC signal peptide 96

<400> SEQUENCE: 171

Met Glu Phe Gly Leu Ser Trp Val Phe Leu Val Ala Val Ile Lys Gly
1               5                   10                  15

Val Gln Cys

<210> SEQ ID NO 172
<211> LENGTH: 19
<212> TYPE: PRT
<213> ORGANISM: Artificial Sequence
<220> FEATURE:
<223> OTHER INFORMATION: Ig HC signal peptide 97

<400> SEQUENCE: 172

Met Glu Phe Gly Leu Thr Trp Val Phe Leu Val Ala Val Ile Lys Gly
1               5                   10                  15

Val His Cys

<210> SEQ ID NO 173
<211> LENGTH: 19
<212> TYPE: PRT
<213> ORGANISM: Artificial Sequence
<220> FEATURE:
<223> OTHER INFORMATION: Ig HC signal peptide 98

<400> SEQUENCE: 173

Met Gln Phe Gly Leu Ser Trp Val Phe Leu Val Ala Leu Leu Arg Gly
```

```
1               5                  10                  15

Val Gln Cys

<210> SEQ ID NO 174
<211> LENGTH: 19
<212> TYPE: PRT
<213> ORGANISM: Artificial Sequence
<220> FEATURE:
<223> OTHER INFORMATION: Ig HC signal peptide 99

<400> SEQUENCE: 174

Met Asp Phe Gly Leu Ala Trp Val Phe Leu Val Ala Leu Leu Arg Gly
1               5                  10                  15

Val Gln Cys

<210> SEQ ID NO 175
<211> LENGTH: 19
<212> TYPE: PRT
<213> ORGANISM: Artificial Sequence
<220> FEATURE:
<223> OTHER INFORMATION: Ig HC signal peptide 100

<400> SEQUENCE: 175

Met Glu Phe Gly Leu Asn Trp Val Leu Leu Val Ala Leu Leu Arg Gly
1               5                  10                  15

Val Gln Cys

<210> SEQ ID NO 176
<211> LENGTH: 19
<212> TYPE: PRT
<213> ORGANISM: Artificial Sequence
<220> FEATURE:
<223> OTHER INFORMATION: Ig HC signal peptide 101

<400> SEQUENCE: 176

Met Glu Phe Gly Leu Ser Trp Val Phe Leu Val Ala Leu Leu Arg Gly
1               5                  10                  15

Val Gln Cys

<210> SEQ ID NO 177
<211> LENGTH: 19
<212> TYPE: PRT
<213> ORGANISM: Artificial Sequence
<220> FEATURE:
<223> OTHER INFORMATION: Ig HC signal peptide 102

<400> SEQUENCE: 177

Met Glu Phe Gly Leu Ser Trp Val Phe Leu Val Ala Leu Leu Arg Gly
1               5                  10                  15

Val Glu Cys

<210> SEQ ID NO 178
<211> LENGTH: 19
<212> TYPE: PRT
<213> ORGANISM: Artificial Sequence
<220> FEATURE:
<223> OTHER INFORMATION: Ig HC signal peptide 103

<400> SEQUENCE: 178

Met Glu Phe Gly Leu Ser Trp Val Phe Leu Val Ala Leu Phe Arg Gly
1               5                  10                  15

Val Gln Cys
```

<210> SEQ ID NO 179
<211> LENGTH: 19
<212> TYPE: PRT
<213> ORGANISM: Artificial Sequence
<220> FEATURE:
<223> OTHER INFORMATION: Ig HC signal peptide 104

<400> SEQUENCE: 179

Met Glu Ser Gly Leu Ser Trp Val Phe Leu Val Ala Leu Leu Arg Gly
1               5                   10                  15

Val Gln Cys

<210> SEQ ID NO 180
<211> LENGTH: 19
<212> TYPE: PRT
<213> ORGANISM: Artificial Sequence
<220> FEATURE:
<223> OTHER INFORMATION: Ig HC signal peptide 105

<400> SEQUENCE: 180

Met Glu Leu Gly Leu Ser Trp Val Phe Leu Val Ser Leu Leu Ala Gly
1               5                   10                  15

Val Gln Cys

<210> SEQ ID NO 181
<211> LENGTH: 19
<212> TYPE: PRT
<213> ORGANISM: Artificial Sequence
<220> FEATURE:
<223> OTHER INFORMATION: Ig HC signal peptide 106

<400> SEQUENCE: 181

Met Glu Leu Gly Leu Ser Trp Ile Phe Leu Val Ala Leu Leu Arg Gly
1               5                   10                  15

Val Gln Cys

<210> SEQ ID NO 182
<211> LENGTH: 19
<212> TYPE: PRT
<213> ORGANISM: Artificial Sequence
<220> FEATURE:
<223> OTHER INFORMATION: Ig HC signal peptide 107

<400> SEQUENCE: 182

Met Glu Phe Gly Leu Ser Trp Val Leu Leu Val Val Phe Leu Gln Gly
1               5                   10                  15

Val Gln Cys

<210> SEQ ID NO 183
<211> LENGTH: 19
<212> TYPE: PRT
<213> ORGANISM: Artificial Sequence
<220> FEATURE:
<223> OTHER INFORMATION: Ig HC signal peptide 108

<400> SEQUENCE: 183

Met Glu Phe Gly Leu Ser Trp Val Phe Leu Val Gly Ile Leu Lys Gly
1               5                   10                  15

Val Gln Cys

<210> SEQ ID NO 184
<211> LENGTH: 19
<212> TYPE: PRT

```
<213> ORGANISM: Artificial Sequence
<220> FEATURE:
<223> OTHER INFORMATION: Ig HC signal peptide 109

<400> SEQUENCE: 184

Met Glu Phe Gly Leu Ser Trp Val Tyr Leu Val Ala Ile Leu Lys Gly
1               5                   10                  15

Val Gln Cys

<210> SEQ ID NO 185
<211> LENGTH: 19
<212> TYPE: PRT
<213> ORGANISM: Artificial Sequence
<220> FEATURE:
<223> OTHER INFORMATION: Ig HC signal peptide 110

<400> SEQUENCE: 185

Met Glu Phe Trp Leu Ser Trp Val Phe Leu Val Ala Ile Leu Lys Gly
1               5                   10                  15

Val Gln Cys

<210> SEQ ID NO 186
<211> LENGTH: 20
<212> TYPE: PRT
<213> ORGANISM: Artificial Sequence
<220> FEATURE:
<223> OTHER INFORMATION: Ig LC signal peptide 1

<400> SEQUENCE: 186

Met Val Leu Gln Thr Gln Val Phe Ile Ser Leu Leu Leu Trp Ile Ser
1               5                   10                  15

Gly Ser Tyr Gly
            20

<210> SEQ ID NO 187
<211> LENGTH: 20
<212> TYPE: PRT
<213> ORGANISM: Artificial Sequence
<220> FEATURE:
<223> OTHER INFORMATION: Ig LC signal peptide 2

<400> SEQUENCE: 187

Met Arg Leu Pro Ala Gln Leu Leu Gly Leu Leu Met Leu Trp Val Ser
1               5                   10                  15

Gly Ser Ser Gly
            20

<210> SEQ ID NO 188
<211> LENGTH: 22
<212> TYPE: PRT
<213> ORGANISM: Artificial Sequence
<220> FEATURE:
<223> OTHER INFORMATION: Ig LC signal peptide 3

<400> SEQUENCE: 188

Met Glu Thr Pro Ala Gln Leu Leu Phe Leu Leu Leu Leu Trp Leu Pro
1               5                   10                  15

Val Ser Asp Thr Thr Gly
            20

<210> SEQ ID NO 189
<211> LENGTH: 20
<212> TYPE: PRT
<213> ORGANISM: Artificial Sequence
```

```
<220> FEATURE:
<223> OTHER INFORMATION: Ig LC signal peptide 4

<400> SEQUENCE: 189

Met Glu Thr Pro Ala Gln Leu Leu Phe Leu Leu Leu Trp Leu Pro
1               5                   10                  15

Gly Thr Thr Gly
            20

<210> SEQ ID NO 190
<211> LENGTH: 20
<212> TYPE: PRT
<213> ORGANISM: Artificial Sequence
<220> FEATURE:
<223> OTHER INFORMATION: Ig LC signal peptide 5

<400> SEQUENCE: 190

Met Glu Thr Pro Ala Gln Leu Leu Phe Leu Leu Leu Trp Leu Pro
1               5                   10                  15

Asp Ile Thr Gly
            20

<210> SEQ ID NO 191
<211> LENGTH: 20
<212> TYPE: PRT
<213> ORGANISM: Artificial Sequence
<220> FEATURE:
<223> OTHER INFORMATION: Ig LC signal peptide 6

<400> SEQUENCE: 191

Met Glu Ala Pro Ala Gln Leu Leu Phe Leu Leu Leu Trp Leu Pro
1               5                   10                  15

Asp Ser Thr Gly
            20

<210> SEQ ID NO 192
<211> LENGTH: 20
<212> TYPE: PRT
<213> ORGANISM: Artificial Sequence
<220> FEATURE:
<223> OTHER INFORMATION: Ig LC signal peptide 7

<400> SEQUENCE: 192

Met Glu Ala Pro Ala Gln Leu Leu Phe Leu Leu Leu Trp Leu Pro
1               5                   10                  15

Asp Thr Thr Gly
            20

<210> SEQ ID NO 193
<211> LENGTH: 22
<212> TYPE: PRT
<213> ORGANISM: Artificial Sequence
<220> FEATURE:
<223> OTHER INFORMATION: Ig LC signal peptide 8

<400> SEQUENCE: 193

Met Asp Met Arg Val Leu Ala Gln Leu Leu Gly Leu Leu Leu Cys
1               5                   10                  15

Phe Pro Gly Ala Arg Cys
            20

<210> SEQ ID NO 194
<211> LENGTH: 22
<212> TYPE: PRT
```

<213> ORGANISM: Artificial Sequence
<220> FEATURE:
<223> OTHER INFORMATION: Ig LC signal peptide 9

<400> SEQUENCE: 194

Met Asp Met Arg Val Pro Ala Gln Leu Leu Gly Leu Leu Leu Leu Trp
1               5                   10                  15

Leu Pro Asp Thr Arg Cys
            20

<210> SEQ ID NO 195
<211> LENGTH: 22
<212> TYPE: PRT
<213> ORGANISM: Artificial Sequence
<220> FEATURE:
<223> OTHER INFORMATION: Ig LC signal peptide 10

<400> SEQUENCE: 195

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 196
<211> LENGTH: 22
<212> TYPE: PRT
<213> ORGANISM: Artificial Sequence
<220> FEATURE:
<223> OTHER INFORMATION: Ig LC signal peptide 11

<400> SEQUENCE: 196

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 197
<211> LENGTH: 22
<212> TYPE: PRT
<213> ORGANISM: Artificial Sequence
<220> FEATURE:
<223> OTHER INFORMATION: Ig LC signal peptide 12

<400> SEQUENCE: 197

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 198
<211> LENGTH: 22
<212> TYPE: PRT
<213> ORGANISM: Artificial Sequence
<220> FEATURE:
<223> OTHER INFORMATION: Ig LC signal peptide 13

<400> SEQUENCE: 198

Met Lys Tyr Leu Leu Pro Thr Ala Ala Ala Gly Leu Leu Leu His Ala
1               5                   10                  15

Ala Gln Pro Ala Met Ala
            20

<210> SEQ ID NO 199
<211> LENGTH: 22

```
<212> TYPE: PRT
<213> ORGANISM: Artificial Sequence
<220> FEATURE:
<223> OTHER INFORMATION: Ig LC signal peptide 14

<400> SEQUENCE: 199

Met Lys Lys Asn Ile Ala Phe Leu Leu Ala Ser Met Phe Val Ser Ile
1               5                   10                  15

Ala Thr Asn Ala Tyr Ala
            20

<210> SEQ ID NO 200
<211> LENGTH: 21
<212> TYPE: PRT
<213> ORGANISM: Artificial Sequence
<220> FEATURE:
<223> OTHER INFORMATION: Ig LC signal peptide 15

<400> SEQUENCE: 200

Met Lys Gln Ser Thr Ile Ala Leu Ala Leu Leu Pro Leu Leu Phe Thr
1               5                   10                  15

Pro Val Thr Lys Ala
            20

<210> SEQ ID NO 201
<211> LENGTH: 22
<212> TYPE: PRT
<213> ORGANISM: Artificial Sequence
<220> FEATURE:
<223> OTHER INFORMATION: Ig LC signal peptide 16

<400> SEQUENCE: 201

Met Lys Lys Thr Ala Ile Ala Ile Ala Val Ala Leu Ala Gly Phe Ala
1               5                   10                  15

Thr Val Ala Gln Ala Ala
            20

<210> SEQ ID NO 202
<211> LENGTH: 22
<212> TYPE: PRT
<213> ORGANISM: Artificial Sequence
<220> FEATURE:
<223> OTHER INFORMATION: Signal peptide

<400> SEQUENCE: 202

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 203
<211> LENGTH: 8
<212> TYPE: DNA
<213> ORGANISM: Artificial Sequence
<220> FEATURE:
<223> OTHER INFORMATION: Variable region promoter octamer sequence

<400> SEQUENCE: 203 atgcaaat                                                           8

<210> SEQ ID NO 204
<211> LENGTH: 582
<212> TYPE: DNA
<213> ORGANISM: Artificial Sequence
<220> FEATURE:
```

<223> OTHER INFORMATION: Heavy chain intronic enhancer

<400> SEQUENCE: 204

```
cggcccccgat gcgggactgc gttttgacca tcataaatca gtttattttt tttaattaat    60
tgagcgaagc tggaagcaga tgatgaatta gagtcaagat ggctgcatgg gggtctccgg   120
cacccacagc aggtggcagg aagcaggtca ccgcgagagt ctattttagg aagcaaaaaa   180
acacaattgg taaatttatc acttctggtt gtgaagaggg ggttttgccc aggcccagat   240
ctgaaagtgc tctactgagc aaaacaacac ctggacaatt gcgtttcta aaataaggcg    300
aggctgaccg aaactgaaaa ggcttttttt aactatctga atttcatttc caatcttagc   360
ttatcaactg ctagtttgtg caaacagcat atcaacttct aaactgcatt cattttaaa   420
gtaagatgtt taagaaatta aacagtctta gggagagttt atgactgtat tcaaaaagtt   480
ttttaaatta gcttgttatc ccttcatgtg ataattaatc tcaaatactt tttcgatacc   540
tcagagcatt attttcataa tgactgtgtt cacaatcttt tt                      582
```

<210> SEQ ID NO 205
<211> LENGTH: 24
<212> TYPE: PRT
<213> ORGANISM: Artificial Sequence
<220> FEATURE:
<223> OTHER INFORMATION: T2A

<400> SEQUENCE: 205

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 206
<211> LENGTH: 22
<212> TYPE: PRT
<213> ORGANISM: Artificial Sequence
<220> FEATURE:
<223> OTHER INFORMATION: P2A

<400> SEQUENCE: 206

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 207
<211> LENGTH: 335
<212> TYPE: PRT
<213> ORGANISM: Artificial Sequence
<220> FEATURE:
<223> OTHER INFORMATION: truncated EGFR (tEGFR)

<400> SEQUENCE: 207

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn

```
                65                  70                  75                  80
Arg Thr Asp Leu His Ala Phe Glu Asn Leu Glu Ile Ile Arg Gly Arg
                    85                  90                  95

Thr Lys Gln His Gly Gln Phe Ser Leu Ala Val Val Ser Leu Asn Ile
                100                 105                 110

Thr Ser Leu Gly Leu Arg Ser Leu Lys Glu Ile Ser Asp Gly Asp Val
                115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
                180                 185                 190

Cys Arg Asn Val Ser Arg Gly Arg Glu Cys Val Asp Lys Cys Asn Leu
                195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
                260                 265                 270

Leu Val Trp Lys Tyr Ala Asp Ala Gly His Val Cys His Leu Cys His
                275                 280                 285

Pro Asn Cys Thr Tyr Gly Cys Thr Gly Pro Gly Leu Glu Gly Cys Pro
                290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```

<210> SEQ ID NO 208
<211> LENGTH: 239
<212> TYPE: PRT
<213> ORGANISM: Artificial Sequence
<220> FEATURE:
<223> OTHER INFORMATION: super-fold green fluorescent protein

<400> SEQUENCE: 208

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
                20                  25                  30

Glu Gly Glu Gly Asp Ala Thr Asn Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Thr Phe Lys Asp Asp Gly Thr Tyr Lys Thr Arg Ala Glu
```

-continued

```
                100                 105                 110
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
        210                 215                 220

Val Thr Ala Ala Gly Ile Thr His Gly Met Asp Glu Leu Tyr Lys
225                 230                 235
```

ENGINEERED B CELLS AND RELATED COMPOSITIONS AND METHODS

CROSS-REFERENCE TO RELATED APPLICATIONS

This application is a U.S. National Stage of International Application No. PCT/US2017/064075 filed Nov. 30, 2017, which claims priority from U.S. provisional application No. 62/429,709 filed Dec. 2, 2016, entitled "Engineered B Cells and Related Compositions and Methods," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042006600SeqList.txt, created on May 24, 2019, which is 64,085 bytes in size. The information in electronic format of the Sequence Listing is incorporated by reference in its entirety.

FIELD

The present disclosure relates in some aspects to engineered B cells, such as for adoptive cell therapy. In some aspects, the disclosure further relates to methods and compositions for engineering and producing the cells, compositions containing the cells, and methods for their administration to subjects. In some embodiments, the cells are engineered to produce and/or secrete an exogenous protein, such as a therapeutic protein, including antibodies and antigen-binding fragments thereof. In some aspects, features of the cells and methods provide for increased or improved activity, efficacy and/or persistence of the cells.

BACKGROUND

Various methods are available for treating diseases, including infectious diseases, cancers, and autoimmune diseases, using therapeutic proteins, such as antibodies or antigen-binding fragments thereof. Such approaches generally involve repeated injections of recombinantly-produced proteins, which can provide various therapeutic effects via one or more mechanisms. The presence of the therapeutic proteins in the body following administration is generally transient. Improved compositions and methods are needed, for example, to improve efficacy of such therapies, for example, by increasing the duration of action of the therapies. Provided are products, compositions, methods and articles of manufacture that meet such needs.

SUMMARY

Provided are engineered B cells capable of producing and/or secreting an exogenous protein, such as a therapeutic protein, such as for use in adoptive cell therapy, for example to treat diseases and/or conditions in a subject in need thereof. Also provided are compositions comprising the cells, methods of producing and using the cells, such as for treating a disease and/or condition, and articles of manufacture comprising the cells or for use in a method described herein.

In some embodiments, provided are engineered B cells comprising one or more nucleic acid molecules comprising one or more coding sequences encoding an exogenous protein under the control of one or more elements to effect secretion of the exogenous protein from the cell, wherein the exogenous protein is not an antibody.

In some embodiments, provided are engineered B cells comprising one or more nucleic acid molecules comprising one or more coding sequences encoding an exogenous protein, wherein expression of the exogenous protein in the engineered B cell is conditional.

In some embodiments, provided are engineered B cells comprising one or more nucleic acid molecules comprising one or more coding sequences encoding an exogenous protein, wherein the engineered B cell expresses an endogenous antibody and comprises a modification that prevents class-switching of the endogenous antibody and/or prevents switching of the endogenous antibody from a membrane-associated form to a secreted form.

In some embodiments, provided are engineered B cells comprising one or more nucleic acid molecules comprising one or more coding sequences encoding an exogenous protein, wherein at least one of the one or more nucleic acid molecules is integrated into or replaces all or a portion of a heavy chain immunoglobulin locus or a light chain immunoglobulin locus of the B cell.

In some embodiments, provided are engineered B cells comprising one or more nucleic acid molecules comprising one or more coding sequences encoding an exogenous protein, wherein the engineered B cell comprises one or more modifications resulting in a greater capacity for the engineered B cell to produce and/or secrete the exogenous protein.

In some embodiments, provided are engineered B cells comprising: one or more nucleic acid molecules comprising one or more coding sequences encoding an exogenous protein; and a chimeric receptor comprising a ligand binding domain, wherein, upon ligand binding, the receptor is capable of inducing (i) a mitogenic or proliferative signal; and/or (ii) a signal that is capable of modulating the differentiation of the engineered B cell.

In some embodiments, provided are engineered B cells comprising: one or more nucleic acid molecules comprising one or more coding sequences encoding an exogenous protein; and a recombinant receptor comprising a ligand binding domain, wherein, upon ligand binding, the receptor is capable of inducing (i) a mitogenic or proliferative signal; and/or (ii) a signal that is capable of modulating the differentiation of the engineered B cell, wherein the exogenous protein does not bind to the target of the ligand binding domain of the receptor and/or the exogenous protein does not contain a ligand binding site contained in the ligand binding domain of the receptor.

In some of any such embodiments, the exogenous protein is secreted by the B cell or is capable of being secreted by the B cell. In some embodiments, the one or more coding sequences comprises a nucleotide sequence encoding a secretory signal peptide. In some embodiments, the secretory signal peptide comprises an amino acid sequence selected from among SEQ ID NOs: 76-202.

In some of any such embodiments, the exogenous protein is a dimer. In some embodiments, the one or more nucleic acid molecules comprises a single nucleic acid molecule comprising a first coding sequence encoding a first domain or subunit of the dimer and a second coding sequence encoding a second domain or subunit of the dimer.

In some of any such embodiments, the exogenous protein is a therapeutic protein.

In some of any such embodiments, the exogenous protein binds to a target molecule associated with a disease or condition, wherein the molecule is optionally a protein, wherein the molecule or protein is expressed on the surface of a cell. In some embodiments, the disease or condition is selected from among a tumor or cancer, an autoimmune disease, an infectious disease or condition, and an inflammatory disease. In some embodiments, the disease or condition is a tumor or cancer. In some embodiments, the disease or condition is a viral infection. In some embodiments, the viral infection is human immunodeficiency virus (HIV) infection.

In some of any such embodiments, the exogenous protein binds to a molecule selected from ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1) or cyclin A1 (CCNA1)XX.

In some of any such embodiments, the exogenous protein is selected from blood factors, thrombolytic agents, hormones, growth factors, cytokines, and antibodies or antigen-binding fragments thereof. In some embodiments, the cytokines are selected from among chemokines, interferons, interleukins, lymphokines, and tumor necrosis factors.

In some of any such embodiments, the exogenous protein is an antibody or antigen-binding fragment thereof. In some embodiments, the antibody or antigen-binding fragment thereof binds to a cancer-associated antigen. In some embodiments, the antibody or antigen-binding fragment thereof binds to a pathogen-associated antigen. In some embodiments, the antibody or antigen-binding fragment thereof binds to a viral antigen. In some embodiments, the antibody or antigen-binding fragment thereof is a broadly neutralizing antiviral antibody or antigen-binding fragment thereof. In some embodiments, the antibody or antigen-binding fragment thereof is a broadly neutralizing anti-HIV antibody or antigen-binding fragment thereof.

In some of any such embodiments, the antibody is derived from alemtuzumab, atezolizumab, basiliximab, bevacizumab (Avastin®), blinatumomab, brentuximab vedotin, catumaxomab, cetuximab, daclizumab (Zenapax), daratumumab, denosumab, dinutuximab, elotuzumab, gemtuzumab (Mylotarg), ibritumomab tiuxetan (Zevalin), ipilimumab, necitumumab, nimotuzumab, nivolumab, obinutuzumab, ofatumumab, panitumumab, pembrolizumab, pertuzumab, pidilizumab (CT-011), ramucirumab, rituximab (Rituxan, MabThera), siltuximab, tositumomab (Bexxar®), trastuzumab, ado-trastuzumab emtansine, zalutumumab, CEA-scan Fab fragment, OC125 monoclonal antibody, ab75705, B72.3, MPDL3280A, MSB001078C, or MEDI4736, or is an antigen-binding fragment thereof. In some embodiments, the one or more nucleic acid molecules encodes the heavy and/or light chain of the antibody or antigen-binding fragment thereof. In some embodiments, the one or more nucleic acid molecules comprises a single nucleic acid molecule comprising a first coding sequence encoding the heavy chain and a second coding sequence encoding the light chain of the antibody or antigen-binding fragment thereof. In some embodiments, the antibody or antigen-binding fragment thereof comprises one or more modifications in the heavy chain and/or light chain such that when the exogenous antibody or antigen-binding fragment is expressed in a cell, the frequency of mispairing with a heavy chain and/or light chain of an endogenous antibody is reduced. In some embodiments, the one or more modifications are in the CH2 and/or CH3 region of the constant chain. In some embodiments, the one or more modifications comprise a knob-into-hole (KiH) modification or a dock and lock (DNL) modification. In some embodiments, the antibody or antigen-binding fragment thereof is a full-length antibody. In some embodiments, the antibody or antigen-binding fragment thereof is a single chain antibody fragment. In some embodiments, the antibody or antigen-binding fragment thereof is an scFv.

In some of any such embodiments where the one or more nucleic acid molecules comprises a first and second coding sequence, the first and second coding sequence are separated by an internal ribosome entry site (IRES), or a nucleotide sequence encoding a self-cleaving peptide or a peptide that causes ribosome skipping, which optionally is T2A, P2A, E2A, or F2A.

In some of any such embodiments, the one or more coding sequences encoding the exogenous protein do not comprise intronic sequences.

In some of any such embodiments, the engineered B cell is a primary B cell. In some embodiments, the engineered B cell is a B cell capable of differentiating into one or more of a plasmablast, a plasma cell, and a memory B cell. In some embodiments, the engineered B cell is a naïve mature B cell. In some embodiments, the engineered B cell comprises: one or more (such as all) phenotypic markers selected from PAX5+, BACH2+, BCL-2+, OBF1+, OCT2+, PU.1+, SPIB+, ETS1+, IRF8+, IRF4low, BLIMP1−, or XBP1−; and/or one or more (such as all) cell surface markers selected from CD19+, CD20+, CD21+, CD22+, CD23+, CD24+, CD10−, CD27−, or CD38low.

In some of any such embodiments, the engineered B cell is a plasmablast, a plasma cell, or a memory B cell. In some embodiments, the engineered B cell comprises one or more (such as all) phenotypic markers selected from PAX5−, BACH2−, BCL-2−, OBF1−, OCT2−, PU.1−, SPIB−, ETS1−, IRF8−, IRF4hi, BLIMP1mid, or XBP1+; and/or one or more (such as all) cell surface markers selected from CD19+, CD38high, CD27high, CD269+, MHCII+, CD20−, or CD138−. In some embodiments, the engineered B cell comprises one or more (such as all) phenotypic markers selected from PAX5−, BACH2−, BCL-2−, OBF1−, OCT2−, PU.1−, SPIB−, ETS1−, IRF8−, IRF4hi, BLIMP1hi, or XBP1+; and/or one or more (such as all) cell surface markers selected from CXCR4+, CD27+, CD38high, CD138+, CD269+, CD19low, CD20−, or MHCII−/low. In some embodiments, the engineered B cell comprises one or more (such as all) phenotypic markers selected from PAX5+, BACH2+, BCL-2+, OBF1+, OCT2+, PU.1+, SPIB+, ETS1+, IRF8+, IRF4low, BLIMP1−, or XBP1−; and/or one or more (such as all) cell surface markers selected from CD19+, CD20+, CD40+, CD27var, CXCR4,5,7+, CD23low, or CD38−.

In some of any such embodiments, the engineered B cell comprises one or more modifications resulting in a greater capacity for the engineered B cell to produce and/or secrete the exogenous protein. In some embodiments, the one or more modifications comprise altered expression of a protein involved in B cell lineage determination. In some embodiments, the one or more modifications comprise: reduced or eliminated expression of one or more proteins selected from PAX5, BACH2, BCL-6, OBF1, OCT2, PU.1, SPIB, ETS1, or IRF8, and/or increased expression of one or more proteins selected from IRF4, BLIMP1, or XBP1. In some embodiments, the altered expression is conditional. In some embodiments, the altered expression is inducible.

In some of any such embodiments, the one or more nucleic acid molecules further comprises at least one promoter operably linked to one of the one or more coding sequences. In some embodiments, the promoter is a B cell promoter. In some embodiments, the promoter is a plasma cell promoter. In some embodiments, the promoter is an immunoglobulin (Ig) promoter. In some embodiments, the promoter is an immunoglobulin heavy chain promoter, a kappa light chain promoter, or a lambda light chain promoter. In some embodiments, the promoter is a constitutively active promoter. In some embodiments, the promoter is selected from SV40, CMV, UBC, EF1A, PGK or CAGG.

In some of any such embodiments, expression of the exogenous protein is conditional. In some embodiments, at least one of the one or more coding sequences is operably linked to a conditional promoter, enhancer, or transactivator. In some embodiments, the conditional promoter, enhancer, or transactivator is an inducible promoter, enhancer, or transactivator or a repressible promoter, enhancer, or transactivator. In some embodiments, the at least one of the one or more coding sequences is operably linked to a conditional promoter that is an inducible promoter. In some embodiments, the conditional promoter is not an immunoglobulin promoter. In some embodiments, the promoter comprises a Lac operator sequence, a tetracycline operator sequence, a galactose operator sequence or a doxycycline operator sequence, or is an analog thereof.

In some of any such embodiments, at least one of the one or more nucleic acid molecules is integrated into or replaces all or a portion of a heavy chain immunoglobulin locus or a light chain immunoglobulin locus of the B cell. In some embodiments, the at least one of the one or more nucleic acid molecules comprises one or more coding sequences operably linked to an endogenous immunoglobulin promoter selected from an immunoglobulin heavy chain promoter, a kappa light chain promoter, or a lambda light chain promoter. In some embodiments, the one or more coding sequences are operably linked to an endogenous Ig enhancer. In some embodiments, the one or more nucleic acid molecules comprises one or more coding sequences in-frame with an adjacent remaining coding sequence of the immunoglobulin locus.

In some of any such embodiments, the exogenous protein is an antibody comprising a first polypeptide comprising a heavy chain sequence and a second polypeptide comprising a light chain sequence, and wherein the one or more coding sequences comprises a first coding sequence encoding the first polypeptide and a second coding sequence encoding the second polypeptide. In some embodiments, the first coding sequence is integrated into or replaces all or a portion of an endogenous immunoglobulin heavy chain locus and/or the second coding sequence is integrated into or replaces all or a portion of an endogenous immunoglobulin light chain locus, such that the engineered B cell is capable of expressing the first and second polypeptides. In some embodiments, the first coding sequence is operably linked to a promoter and/or enhancer associated with the endogenous immunoglobulin heavy chain locus and/or the second coding sequence is operably linked to a promoter and/or enhancer associated with the endogenous immunoglobulin light chain locus. In some embodiments, the first and second coding sequences are linked by a linker sequence, such that the engineered B cell is capable of expressing the first and second polypeptides. In some embodiments, the first and second coding sequences are integrated into or replace all or a portion of an endogenous immunoglobulin heavy chain or light chain locus. In some embodiments, the linker sequence is or comprises an internal ribosome entry site (IRES), or encodes a self-cleaving peptide or a peptide that causes ribosome skipping, which optionally is a T2A, a P2A, an E2A, or an F2A. In some embodiments, the exogenous protein is a single chain antibody fragment comprising a heavy chain sequence and a light chain sequence, and wherein the one or more coding sequences comprises a coding sequence encoding the single chain antibody fragment. In some embodiments, the coding sequence is integrated into or replace all or a portion of an endogenous immunoglobulin heavy chain or light chain locus, such that the engineered B cell is capable of expressing the single chain antibody fragment. In some embodiments, the single chain antibody fragment is an scFv.

In some of any such embodiments, the engineered B cell expresses an endogenous B cell receptor. In some embodiments, the endogenous B cell receptor is specific for a ligand present in a vaccine. In some embodiments, the vaccine is selected from among a diphtheria, tetanus, and/or pertussis vaccine, an influenza vaccine, a measles, mumps, rubella, and/or varicella vaccine, a hepatitis vaccine, a polio vaccine, a rabies vaccine, a shingles vaccine, a smallpox vaccine, a typhoid vaccine, and a yellow fever vaccine.

In some of any such embodiments, the B cell comprises an agent or genetic disruption that reduces or eliminates expression of an endogenous immunoglobulin heavy and/or light chain product. In some embodiments, the genetic disruption comprises a disruption in the gene encoding the endogenous immunoglobulin heavy and/or light chain product. In some embodiments, the genetic disruption is biallelic. In some embodiments, the expression of the endogenous immunoglobulin heavy and/or light chain product is reduced by at least 50, 60, 70, 80, 90, or 95% as compared to the expression in the B cell in the absence of the agent or genetic disruption. In some embodiments, the endogenous immunoglobulin heavy and/or light chain product is not expressed.

In some of any such embodiments, the one or more nucleic acid molecules is codon-optimized.

In some of any such embodiments, the engineered B cell expresses a recombinant receptor comprising a ligand binding domain, which, upon ligand binding, is capable of inducing (i) a mitogenic or proliferative signal; and/or (ii) a signal that is capable of modulating the differentiation of the engineered B cell. In some embodiments, the receptor is a chimeric receptor comprising an ITAM-containing intracellular signaling domain. In some embodiments, the signaling domain is separated from the ligand-binding domain by a transmembrane domain, and optionally one or more spacers or linkers. In some embodiments, the receptor is contained in a complex comprising an endogenous protein comprising an ITAM-containing intracellular signaling domain. In some embodiments, the ITAM-containing intracellular signaling domain comprises an intracellular signaling domain derived from CD79A, CD79B, CD3ζ, FcRγ, FcRβ, CD3γ, CD3δ, CD3ε, CD5, CD22, CD79a, CD79b, or CD66d. In some embodiments, upon ligand binding, the receptor signals via the ITAM-containing intracellular signaling domain.

In some of any such embodiments where the engineered B cell comprises a recombinant receptor, the ligand-binding domain comprises an antibody moiety. In some embodiments, the antibody moiety is or comprises a full length antibody or an antigen-binding fragment thereof. In some embodiments, the receptor comprises a transmembrane domain derived from a B cell receptor, the α, β, δ, or γ chain of the T-cell receptor, CD28, CD3ε, CD3ζ, CD45, CD4, CD5, CD8, CD9, CD16, CD22, CD33, CD37, CD64, CD80, CD86, CD134, CD137, or CD154. In some embodiments, the exogenous protein is an antibody or antigen-binding fragment and the ligand-binding domain of the receptor comprises the same heavy and/or light chain as the exogenous protein. In some embodiments, the receptor is a membrane-anchored form of the exogenous protein.

In some of any such embodiments, the receptor is encoded by a nucleic acid sequence that does not comprise intronic sequences.

In some of any such embodiments, the exogenous protein and the receptor recognize the same target antigen and/or the ligand binding domain and the exogenous protein contain the same ligand binding sites.

In some of any such embodiments, the exogenous protein and the receptor bind to different ligands and/or have different ligand binding sites.

In some of any such embodiments, the ligand-binding domain of the receptor binds a ligand associated with a disease or condition. In some embodiments, the ligand-binding domain of the receptor binds a ligand present in a tumor environment in the subject. In some embodiments, the ligand-binding domain of the receptor binds a virally associated ligand.

In some of any such embodiments, the ligand-binding domain of the receptor binds an environmental ligand in a subject selected from among ligands that are not overexpressed on a disease cell in the subject, ligands that exhibit widespread tissue or cell expression in the subject, ligands that are ubiquitously expressed in the subject, ligands that are systemically expressed in the subject, ligands that are not tissue specific in the subject, and ligands exogenous to the subject.

In some of any such embodiments, the one or more nucleic acid molecules further encodes the receptor. In some embodiments, the one or more nucleic acid molecules comprises a linker sequence separating the sequence of nucleotides encoding the exogenous protein and the sequence of nucleotides encoding the receptor. In some embodiments, the linker sequence is or comprises an internal ribosome entry site (IRES), or encodes a self-cleaving peptide or a peptide that causes ribosome skipping, which optionally is a T2A, a P2A, an E2A, or an F2A.

In some of any such embodiments, the engineered B cell expresses an endogenous antibody and comprises a modification that prevents class-switching of the endogenous antibody and/or prevents switching of the endogenous antibody from a membrane-associated form to a secreted form. In some embodiments, the modification that prevents class-switching comprises: reduced or eliminated expression of activation-induced deaminase (AID), uracil DNA glycosylase, and/or apyrimidic/apurinic (AP)-endonucleases; and/or mutation of one or more switch regions in the endogenous antibody locus. In some embodiments, the modification that prevents switching of an endogenous antibody expressed in the engineered B cell from a membrane-associated form to a secreted form comprises mutation of the polyadenylation signal upstream of the M1 exon at the endogenous antibody locus. In some embodiments, the endogenous antibody is an IgM or IgD.

In some of any such embodiments, the one or more coding sequences does not contain a nucleotide sequence encoding a transmembrane domain or the exogenous protein is not expressed on the cell surface or is not capable of being expressed on the cell surface.

In some of any such embodiments, the exogenous protein is secreted from the cell or is capable of being secreted from the cell upon ligand binding.

In some of any such embodiments, the B cell is a human B cell.

In some of any such embodiments, the engineered B cell is a primary cell obtained from a patient.

In some of any such embodiments, the engineered B cell is in a container or is in a formulation.

In some embodiments, provided are nucleic acid molecules comprising one or more coding sequences encoding a therapeutic protein and a receptor, wherein the receptor comprises a ligand binding domain, and wherein upon ligand binding, the receptor is capable of inducing (i) a mitogenic or proliferative signal; and/or (ii) a signal that is capable of modulating the differentiation of a B cell. In some embodiments, the nucleic acid molecules further comprise at least one promoter that is operatively linked to control expression of the therapeutic protein and/or the receptor. In some embodiments, the sequence of nucleotides encoding the therapeutic protein is operatively linked to a first promoter and the sequence of nucleotides encoding the receptor is operatively linked to a second promoter, which first and second promoter can be the same or different. In some embodiments, the nucleic acid molecule comprises a linker sequence separating the sequence of nucleotides encoding the therapeutic protein and the sequence of nucleotides encoding the receptor. In some embodiments, the linker sequence is or comprises an internal ribosome entry site (IRES), or encodes a self-cleaving peptide or a peptide that causes ribosome skipping, optionally a T2A, a P2A, an E2A, or an F2A.

In some embodiments, provided are vectors comprising the nucleic acid molecule of any one of the embodiments described above. In some embodiments, the vector is a viral vector. In some embodiments, the vector is a retroviral vector. In some embodiments, the vector is a lentiviral vector or a gammaretroviral vector.

In some embodiments, provided are engineered B cells comprising the nucleic acid molecule or vector of any one of the embodiments described above.

In some embodiments, provided are methods of producing an engineered B cell, comprising introducing into a B cell or a B cell precursor the nucleic acid molecule or vector of any of the embodiments described above.

In some embodiments, provided are methods of producing an engineered B cell, the methods comprising introducing one or more nucleic acid molecules comprising one or more coding sequences encoding an exogenous protein under the control of one or more elements to effect secretion of the exogenous protein into a B cell or B cell precursor, wherein the exogenous protein is not an antibody.

In some embodiments, provided are methods of producing an engineered B cell, the methods comprising introducing one or more nucleic acid molecules comprising one or more coding sequences encoding an exogenous protein into a B cell or B cell precursor, wherein expression of the exogenous protein in the engineered B cell is conditional.

In some embodiments, provided are methods of producing an engineered B cell, the methods comprising introducing one or more nucleic acid molecules comprising one or more coding sequences encoding an exogenous protein into a B cell or B cell precursor, wherein the engineered B cell (1) expresses an endogenous antibody and (2) comprises a modification that prevents class-switching of the endogenous antibody and/or prevents switching of the endogenous antibody from a membrane-associated form to a secreted form.

In some embodiments, provided are methods of producing an engineered B cell, the methods comprising introducing one or more nucleic acid molecules comprising one or more coding sequences encoding an exogenous protein into a B cell or B cell precursor, wherein at least one of the one or more nucleic acid molecules is integrated into a target locus selected from a heavy chain immunoglobulin locus or a light chain immunoglobulin locus by insertion into the target locus or replacement of all or a portion of the target locus.

In some embodiments, provided are methods of producing an engineered B cell, the methods comprising introducing one or more nucleic acid molecules comprising one or more coding sequences encoding an exogenous protein into a B cell or B cell precursor, wherein the engineered B cell comprises one or more modifications resulting in a greater capacity for the engineered B cell to produce and/or secrete the exogenous protein.

In some embodiments, provided are methods of producing an engineered B cell, the method comprising introducing one or more nucleic acid molecules comprising one or more coding sequences encoding an exogenous protein into a B cell or B cell precursor, wherein the B cell comprises a chimeric receptor comprising a ligand binding domain, wherein, upon ligand binding, the receptor is capable of inducing (i) a mitogenic or proliferative signal; and/or (ii) a signal that is capable of modulating the differentiation of the engineered B cell.

In some embodiments, provided are methods of producing an engineered B cell, the method comprising introducing one or more nucleic acid molecules comprising one or more coding sequences encoding an exogenous protein into a B cell or B cell precursor, wherein the B cell comprises a recombinant receptor comprising a ligand binding domain, wherein, upon ligand binding, the receptor is capable of inducing (i) a mitogenic or proliferative signal; and/or (ii) a signal that is capable of modulating the differentiation of the engineered B cell, and wherein the exogenous protein does not bind to the target of the ligand binding domain of the receptor and/or the exogenous protein does not contain a ligand binding site contained in the ligand binding domain of the receptor.

In some of any such embodiments, the exogenous protein is secreted by the engineered B cell or is capable of being secreted by the engineered B cell. In some embodiments, the one or more coding sequences comprises a nucleotide sequence encoding a secretory signal peptide. In some embodiments, the secretory signal peptide comprises and amino acid selected from among SEQ ID NOs: 76-202.

In some of any such embodiments, the exogenous protein is a dimer. In some embodiments, the one or more nucleic acid molecules comprises a single nucleic acid molecule comprising a first coding sequence encoding a first domain or subunit and a second coding sequence encoding a second domain or subunit of the dimer.

In some of any such embodiments, the exogenous protein is a therapeutic protein.

In some of any such embodiments, the exogenous protein binds to a target molecule associated with a disease or condition, wherein the molecule is optionally a protein, wherein the molecule or protein is expressed on the surface of a cell. In some embodiments, the disease or condition is selected from among a tumor or cancer, an autoimmune disease, an infectious disease or condition, an inflammatory disease. In some embodiments, the disease or condition is a tumor or cancer.

In some of any such embodiments, the exogenous protein binds to a molecule selected from ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1) or cyclin A1 (CCNA1)XX.

In some of any such embodiments, the exogenous protein is selected from blood factors, thrombolytic agents, hormones, growth factors, cytokines (including chemokines, interferons, interleukins, lymphokines, and tumor necrosis factors), and antibodies or antigen-binding fragments thereof.

In some of any such embodiments, the exogenous protein is an antibody or antigen-binding fragment thereof. In some embodiments, the antibody or antigen-binding fragment thereof binds to a cancer-associated antigen. In some embodiments, the antibody or antigen-binding fragment thereof binds to a pathogen-associated antigen. In some embodiments, the antibody or antigen-binding fragment thereof binds to a viral antigen. In some embodiments, the antibody or antigen-binding fragment thereof is a broadly neutralizing antiviral antibody or antigen-binding fragment thereof. In some embodiments, the antibody or antigen-binding fragment thereof is a broadly neutralizing anti-HIV antibody or antigen-binding fragment thereof.

In some embodiments, the antibody is derived from alemtuzumab, atezolizumab, basiliximab, bevacizumab (Avastin®), blinatumomab, brentuximab vedotin, catumaxomab, cetuximab, daclizumab (Zenapax), daratumumab, denosumab, dinutuximab, elotuzumab, gemtuzumab (Mylotarg), ibritumomab tiuxetan (Zevalin), ipilimumab, necitumumab, nimotuzumab, nivolumab, obinutuzumab, ofatumumab, panitumumab, pembrolizumab, pertuzumab, pidilizumab (CT-011), ramucirumab, rituximab (Rituxan, Mabthera), siltuximab, tositumomab (Bexxar®), trastuzumab, ado-trastuzumab emtansine, zalutumumab, CEA-scan Fab fragment, OC125 monoclonal antibody, ab75705, B72.3, MPDL3280A, MSB001078C, or MEDI4736, or is an antigen-binding fragment thereof. In some embodiments, the one or more nucleic acid molecules encodes the heavy and/or light chain of the antibody or antigen-binding fragment thereof. In some embodiments, the one or more nucleic acid molecules comprises a single nucleic acid molecule comprising a first coding sequence encoding the heavy chain and a second coding sequence encoding the light chain of the antibody or antigen-binding fragment thereof. In some embodiments, the antibody or antigen-binding fragment thereof comprises one or more modifications in the heavy chain and/or light chain such that when the exogenous antibody or antigen-binding fragment is expressed in a cell, the frequency of mispairing with a heavy chain and/or light chain of an endogenous antibody is reduced. In some embodiments, the one or more modifications are in the CH2 and/or CH3 region of the constant chain. In some embodiments, the one or more modifications comprise a knob-into-hole (KiH) modification or a dock and lock (DNL) modification. In some embodiments, the antibody or antigen-binding fragment thereof is a full-length antibody. In some embodiments, the antibody or antigen-binding fragment thereof is a single chain antibody fragment. In some embodiments, the antibody or antigen-binding fragment thereof is an scFv.

In some of any such embodiments where the one or more nucleic acid molecules comprises a first and second coding sequence, the first and second coding sequence are separated by an internal ribosome entry site (IRES), or a nucleotide sequence encoding a self-cleaving peptide or a peptide that causes ribosome skipping, which optionally is T2A, P2A, E2A, or F2A.

In some of any such embodiments, the one or more coding sequences encoding the exogenous protein do not comprise intronic sequences.

In some of any such embodiments, the B cell or B cell precursor is a hematopoietic stem cell (HSC) or a primary B cell selected from a naïve mature B cell, a plasmablast, a plasma cell, or a memory B cell. In some embodiments, the engineered B cell is a B cell capable of differentiating into one or more cells selected from a plasmablast, a plasma cell, or a memory B cell. In some embodiments, the engineered B cell is a naïve mature B cell. In some embodiments, the engineered B cell comprises: one or more (such as all) phenotypic markers selected from PAX5+, BACH2+, BCL-2+, OBF1+, OCT2+, PU.1+, SPIB+, ETS1+, IRF8+, IRF4low, BLIMP1−, or XBP1−; and/or one or more (such as all) cell surface markers selected from CD19+, CD20+, CD21+, CD22+, CD23+, CD24+, CD10−, CD27−, or CD38low. In some embodiments, the engineered B cell is a plasmablast, a plasma cell, or a memory B cell. In some embodiments, the engineered B cell comprises one or more (such as all) phenotypic markers selected from PAX5−, BACH2−, BCL-2−, OBF1−, OCT2−, PU.1−, SPIB−, ETS1−, IRF8−, IRF4hi, BLIMP1mid, or XBP1+; and/or one or more (such as all) cell surface markers selected from CD19+, CD38high, CD27high, CD269+, MHCII+, CD20−, or CD138−. In some embodiments, the engineered B cell comprises one or more (such as all) phenotypic markers selected from PAX5−, BACH2−, BCL-2−, OBF1−, OCT2−, PU.1−, SPIB−, ETS1−, IRF8−, IRF4hi, BLIMP1hi, or XBP1+; and/or one or more (such as all) cell surface markers selected from CXCR4+, CD27+, CD38high, CD138+, CD269+, CD19low, CD20−, or MHCII−/low. In some embodiments, the engineered B cell comprises one or more (such as all) phenotypic markers selected from PAX5+, BACH2+, BCL-2+, OBF1+, OCT2+, PU.1+, SPIB+, ETS1+, IRF8+, IRF4low, BLIMP1−, or XBP1−; and/or one or more (such as all) cell surface markers selected from CD19+, CD20+, CD40+, CD27var, CXCR4,5,7+, CD23low, or CD38−.

In some of any such embodiments, the method further comprises contacting the B cell or B cell precursor with one or more agents that modulate B cell differentiation. In some embodiments, the one or more agents are selected from IL-2, IL-3, IL-6, IL-10, SCF, G-CSF, CpG, CD40 ligand, Flt3 ligand, or thrombopoietin.

In some of any such embodiments, the method further comprises co-culturing the B cell or B cell precursor with cells that express one or more B cell lineage growth factors, optionally including IL-7 and CD40 ligand.

In some of any such embodiments, the engineered B cell comprises one or more modifications resulting in a greater capacity for the engineered B cell to produce and/or secrete the exogenous protein. In some embodiments, the one or more modifications comprise altered expression of a protein involved in B cell lineage determination. In some embodiments, the one or more modifications comprise: reduced or eliminated expression of one or more proteins selected from PAX5, BACH2, BCL-6, OBF1, OCT2, PU.1, SPIB, ETS1, or IRF8, and/or increased expression of one or more proteins selected from IRF4, BLIMP1, or XBP1. In some embodiments, the altered expression is conditional. In some embodiments, the altered expression is inducible.

In some of any such embodiments, the one or more nucleic acid molecules further comprises at least one promoter operably linked to one of the one or more coding sequences. In some embodiments, the promoter is a B cell promoter. In some embodiments, the promoter is a plasma cell promoter. In some embodiments, the promoter is an immunoglobulin (Ig) promoter. In some embodiments, the promoter is an immunoglobulin heavy chain promoter, a kappa light chain promoter, or a lambda light chain promoter. In some embodiments, the promoter is a constitutively active promoter. In some embodiments, the promoter is selected from SV40, CMV, UBC, EF1A, PGK or CAGG.

In some of any such embodiments, expression of the exogenous protein is conditional. In some embodiments, at least one of the one or more coding sequences is operably linked to a conditional promoter, enhancer, or transactivator. In some embodiments, the conditional promoter, enhancer, or transactivator is an inducible promoter, enhancer, or transactivator or a repressible promoter, enhancer, or transactivator. In some embodiments, the at least one of the one or more coding sequences is operably linked to a conditional promoter that is an inducible promoter. In some embodiments, the conditional promoter is not an immunoglobulin promoter. In some embodiments, the promoter comprises a Lac operator sequence, a tetracycline operator sequence, a galactose operator sequence or a doxycycline operator sequence, or is an analog thereof.

In some of any such embodiments, at least one of the one or more nucleic acid molecules is integrated into a target locus by insertion into the target locus or replacement of all or a portion of the target locus. In some embodiments, the target locus is a heavy chain immunoglobulin locus or a light chain immunoglobulin locus. In some embodiments, one or more coding sequences contained in the at least one of the one or more nucleic acid molecules are operably linked to an endogenous immunoglobulin promoter selected from an immunoglobulin heavy chain promoter, a kappa light chain promoter, or a lambda light chain promoter. In some embodiments, one or more coding sequences contained in the at least one of the one or more nucleic acid molecules are operably linked to an endogenous Ig enhancer. In some embodiments, one or more coding sequences contained in the at least one of the one or more nucleic acid molecules are in-frame with an adjacent remaining coding sequence of the immunoglobulin locus.

In some of any such embodiments, the exogenous protein is an antibody comprising a first polypeptide comprising a heavy chain sequence and a second polypeptide comprising a light chain sequence, and wherein the one or more coding sequences comprises a first coding sequence encoding the first polypeptide and a second coding sequence encoding the second polypeptide. In some embodiments, the first coding sequence is integrated into or replaces all or a portion of an endogenous immunoglobulin heavy chain locus and/or the second coding sequence is integrated into or replaces all or a portion of an endogenous immunoglobulin light chain locus, such that the engineered B cell is capable of expressing the first and second polypeptides. In some embodiments, the first coding sequence is operably linked to a promoter and/or enhancer associated with the endogenous immunoglobulin heavy chain locus and/or the second coding sequence is operably linked to a promoter and/or enhancer associated with the endogenous immunoglobulin light chain locus. In some embodiments, the first and second coding sequences are linked by a linker sequence, such that the engineered B cell is capable of expressing the first and second polypeptides. In some embodiments, the first and second coding sequences are integrated into or replace all or a portion of an endogenous immunoglobulin heavy chain or light chain locus. In some embodiments, the linker sequence is or comprises an internal ribosome entry site (IRES), or encodes a self-cleaving peptide or a peptide that causes ribosome skipping, which optionally is T2A, P2A, E2A, or F2A.

In some of any such embodiments, the exogenous protein is a single chain antibody fragment comprising a heavy chain sequence and a light chain sequence, and wherein the one or more coding sequences comprises a coding sequence encoding the single chain antibody fragment. In some embodiments, the coding sequence is integrated into or replace all or a portion of an endogenous immunoglobulin heavy chain or light chain locus, such that the engineered B cell is capable of expressing the single chain antibody fragment. In some embodiments, the single chain antibody fragment is an scFv.

In some of any such embodiments, the engineered B cell expresses an endogenous B cell receptor. In some embodiments, the endogenous B cell receptor is specific for a ligand present in a vaccine. In some embodiments, the vaccine is selected from among a diphtheria, tetanus, and/or pertussis vaccine, an influenza vaccine, a measles, mumps, rubella, and/or varicella vaccine, a hepatitis vaccine, a polio vaccine, a rabies vaccine, a shingles vaccine, a smallpox vaccine, a typhoid vaccine, and a yellow fever vaccine.

In some of any such embodiments, the at least one of the one or more nucleic acid molecules comprises sequences that allow for integration of the at least one of the one or more nucleic acid molecules into the B cell at the target locus by homologous recombination. In some embodiments, the at least one of the one or more nucleic acid molecules comprises flanking sequences that are homologous to sequences at the target locus.

In some of any such embodiments, integration into the target locus of the at least one of the one or more nucleic acid molecules is mediated by a designer nuclease selected from zinc-finger nucleases (ZFNs), transcription activator-like effector nucleases (TALENs), or RNA-guided nucleases (RGNs). In some embodiments, the RGN is a clustered, regularly interspaced, short palindromic repeats (CRISPR)-associated Cas9 (CRISPR-Cas9) nuclease.

In some of any such embodiments, at least one of the one or more nucleic acid molecules is inserted into a random locus.

In some of any such embodiments, the one or more nucleic acid molecules is introduced into the B cell by viral transduction, transposition, electroporation, or chemical transfection. In some embodiments, the one or more nucleic acid molecules is introduced into the B cell by transduction with a retroviral vector comprising the one or more nucleic acid molecules. In some embodiments, the one or more nucleic acid molecules is introduced into the B cell by transduction with a lentiviral vector comprising the one or more nucleic acid molecules. In some embodiments, the one or more nucleic acid molecules is introduced into the B cell by transposition with a transposon comprising the one or more nucleic acid molecules. In some embodiments, the one or more nucleic acid molecules is introduced into the B cell by electroporation or transfection of a vector comprising the one or more nucleic acid molecules.

In some of any such embodiments, the B cell comprises an agent or genetic disruption that reduces or eliminates expression of an endogenous immunoglobulin heavy and/or light chain product. In some embodiments, the genetic disruption comprises a disruption in the gene encoding the endogenous immunoglobulin heavy and/or light chain product. In some embodiments, the genetic disruption is biallelic. In some embodiments, the expression of the endogenous immunoglobulin heavy and/or light chain product is reduced by at least 50, 60, 70, 80, 90, or 95% as compared to the expression in the B cell in the absence of the agent or genetic disruption. In some embodiments, the endogenous immunoglobulin heavy and/or light chain product is not expressed.

In some of any such embodiments, the one or more nucleic acid molecules is codon-optimized.

In some of any such embodiments, the engineered B cell expresses a recombinant receptor comprising a ligand binding domain, which, upon ligand binding, is capable of inducing (i) a mitogenic or proliferative signal; and/or (ii) a signal that is capable of modulating the differentiation of the engineered B cell. In some embodiments, the receptor is a chimeric receptor comprising an ITAM-containing intracellular signaling domain. In some embodiments, the signaling domain is separated from the ligand-binding domain by a transmembrane domain, and optionally one or more spacers or linkers. In some embodiments, the receptor is contained in a complex comprising an endogenous protein comprising an ITAM-containing intracellular signaling domain. In some embodiments, the ITAM-containing intracellular signaling domain comprises an intracellular signaling domain derived from CD79A, CD79B, CD3ζ, FcRγ, FcRβ, CD3γ, CD3δ, CD3ε, CD5, CD22, CD79a, CD79b, or CD66d. In some embodiments, upon ligand binding, the receptor signals via the ITAM-containing intracellular signaling domain.

In some of any such embodiments where the engineered B cell comprises a recombinant receptor, the ligand-binding domain comprises an antibody moiety. In some embodiments, the antibody moiety is or comprises a full length antibody or an antigen-binding fragment thereof. In some embodiments, the receptor comprises a transmembrane domain derived from a B cell receptor, the α, β, δ, or γ chain of the T-cell receptor, CD28, CD3ε, CD3ζCD45, CD4, CD5, CD8, CD9, CD16, CD22, CD33, CD37, CD64, CD80, CD86, CD134, CD137, or CD154. In some embodiments, the exogenous protein is an antibody or antigen-binding fragment and the ligand-binding domain of the receptor comprises the same heavy and/or light chain as the exogenous protein. In some embodiments, the receptor is a membrane-anchored form of the exogenous protein. In some embodiments, the receptor is encoded by a nucleic acid sequence that does not comprise intronic sequences.

In some of any such embodiments, the exogenous protein and the receptor recognize the same target antigen and/or the ligand binding domain and the exogenous protein contain the same ligand binding sites.

In some of any such embodiments, the exogenous protein and the receptor bind to different ligands and/or have different ligand binding sites.

In some of any such embodiments, the ligand-binding domain of the receptor binds a ligand associated with a disease or condition. In some embodiments, the ligand-binding domain of the receptor binds a ligand present in a tumor environment in the subject. In some embodiments, the ligand-binding domain of the receptor binds a virally associated ligand.

In some of any such embodiments, the ligand-binding domain of the receptor binds an environmental ligand in a subject selected from among ligands that are not overexpressed on a disease cell in the subject, ligands that exhibit widespread tissue or cell expression in the subject, ligands that are ubiquitously expressed in the subject, ligands that are systemically expressed in the subject, ligands that are not tissue specific in the subject, and ligands exogenous to the subject.

In some of any such embodiments, the one or more nucleic acid molecules further encodes the receptor. In some embodiments, the one or more nucleic acid molecules comprises a linker sequence separating the sequence of nucleotides encoding the exogenous protein and the sequence of nucleotides encoding the receptor. In some embodiments, the linker sequence is or comprises an internal ribosome entry site (IRES), or encodes a self-cleaving peptide or a peptide that causes ribosome skipping, which optionally is T2A, P2A, E2A, or F2A.

In some of any such embodiments, the engineered B cell expresses an endogenous antibody and comprises a modification that prevents class-switching of the endogenous antibody and/or prevents switching of the endogenous antibody from a membrane-associated form to a secreted form. In some embodiments, the modification that prevents class-switching comprises: reduced or eliminated expression of activation-induced deaminase (AID), uracil DNA glycosylase, and/or apyrimidic/apurinic (AP)-endonucleases; and/or mutation of one or more switch regions in the endogenous antibody locus. In some embodiments, the modification that prevents switching of an endogenous antibody expressed in the engineered B cell from a membrane-associated form to a secreted form comprises mutation of the polyadenylation signal upstream of the M1 exon at the endogenous antibody locus. In some embodiments, the endogenous antibody is an IgM or IgD.

In some of any such embodiments, the one or more coding sequences does not contain a nucleotide sequence encoding a transmembrane domain or the exogenous protein is not expressed on the cell surface or is not capable of being expressed on the cell surface.

In some of any such embodiments, the exogenous protein is secreted from the cell or is capable of being secreted from the cell upon ligand binding.

In some of any such embodiments, the B cell is a human B cell.

In some of any such embodiments, the engineered B cell is a primary cell obtained from a patient.

In some embodiments, provided are engineered B cells prepared by the method of any of the embodiments described above.

In some embodiments, provided are pharmaceutical compositions comprising the engineered B cell of any one of the embodiments described above and a pharmaceutically acceptable carrier.

In some embodiments, provided are articles of manufacture, comprising the cells or the pharmaceutical composition of any one of the embodiments described above. In some embodiments, the article of manufacture is a container. In some embodiments, the container is a bag.

In some embodiments, provided are methods of treatment, comprising administering the engineered B cell or the pharmaceutical composition of any one of the embodiments described above to a subject having a disease or condition.

In some embodiments, the exogenous protein is a therapeutic protein useful for treating the disease or condition. In some embodiments, the therapeutic protein is selected from blood factors, thrombolytic agents, hormones, growth factors, cytokines (including chemokines, interferons, interleukins, lymphokines, and tumor necrosis factors), and antibodies or antigen-binding fragments thereof. In some embodiments, the exogenous protein is an antibody or antigen-binding fragment thereof that specifically binds to a ligand or antigen associated with the disease or condition. In some embodiments, the antibody or antigen-binding fragment thereof binds to a cancer-associated antigen. In some embodiments, the antibody or antigen-binding fragment thereof binds to a pathogen-associated antigen. In some embodiments, the antibody or antigen-binding fragment thereof binds to a viral antigen. In some embodiments, the antibody or antigen-binding fragment thereof is a broadly neutralizing antiviral antibody or antigen-binding fragment thereof. In some embodiments, the antibody or antigen-binding fragment thereof is a broadly neutralizing anti-HIV antibody or antigen-binding fragment thereof.

In some of any such embodiments, the engineered B cell is a naïve mature B cell or a memory B cell. In some embodiments, the method further comprises inducing the engineered B cell to increase production and/or secretion of the exogenous protein. In some embodiments, the inducing comprises administering to the subject an agent that binds to the ligand binding domain of an endogenous B cell receptor expressed in the engineered B cell. In some embodiments, the inducing comprises administering to the subject an agent that binds to the ligand binding domain of a recombinant or chimeric receptor expressed in the engineered B cell. In some embodiments, the engineered B cell is induced to differentiate into a plasmablast or a plasma cell.

In some of any such embodiments, the engineered B cell is a plasmablast or plasma cell.

In some of any such embodiments, the exogenous protein is under the control of an endogenous immunoglobulin promoter or a constitutively active promoter.

In some of any such embodiments, the exogenous protein is under the control of an inducible promoter, and the method further comprises administering to the subject an agent that activates the inducible promoter.

In some of any such embodiments, a therapeutic amount of the engineered B cell persists in the subject for at least about 1 month, at least 2 months, at least 6 months or at least a year following administration.

In some of any such embodiments, the treatment results in a duration of action of at least about 1 month, at least 2 months, at least 6 months or at least a year.

In some of any such embodiments, a single administration of the engineered B cell or composition results in an increased duration of action compared to the maximum tolerable duration of action resulting from a single direct administration of the exogenous protein. In some embodiments, the increase is at least 1.2-fold, 1.5-fold, 2-fold, 3-fold, 4-fold, or 5-fold.

In some of any such embodiments, the disease or conditions is a cancer, a tumor, an autoimmune disease or disorder, or an infectious disease.

In some of any such embodiments, the engineered B cell is autologous to the subject.

In some of any such embodiments, the engineered B cell is allogeneic to the subject.

In some of any such embodiments, the subject is human.

In some of any such embodiments, the dose of cells administered is at least or at least about or is or is about $1\times10^5$ cells per kilogram body weight of the subject, is at least or at least about or is or is about $1\times10^7$ cells, and/or is at least or at least about or is or is about $1\times10^7$ cells/m² of the subject.

DETAILED DESCRIPTION

I. Engineering B Cells to Produce Therapeutic Proteins

Provided herein are engineered B cells for adoptive cell therapy, e.g., adoptive immunotherapy. The provided cells express and/or secrete an exogenous protein that is known to be or that may be a therapeutic protein, such as an antibody or antigen-binding fragment thereof. In some aspects, the cells include engineered B cells at various stages of development or committed to different B cell lineages, or B cells that are capable of differentiating into cells at various stages of development and committed to different B cell lineages, including naïve mature B cells, plasmablasts, plasma cells, and memory B cells. Also provided are methods and uses of the cells, such as in adoptive therapy in the treatment of diseases or conditions, such as infectious diseases, cancer, and autoimmune diseases. Also provided are methods for producing the cells, compositions containing the cells, and kits and devices containing and for using, producing and/or administering the cells. In some embodiments, the cells provide a long-lived source of a therapeutic protein useful for treating a disease or condition.

In some embodiments, the provided B cells are engineered with a nucleic acid molecule encoding an exogenous protein targeting a disease or condition of interest. In some embodiments, the engineered B cells secrete the exogenous protein, e.g. antibody or other therapeutic protein. In some embodiments, the engineered B cells further comprise a modification of one or more endogenous genes to facilitate, such as increase, the ability of the engineered B cells to produce and/or secrete the exogenous protein.

Monoclonal antibody therapies have been used in the treatment of a number of diseases, including infectious diseases, cancers and autoimmune disease. Such approaches generally involve repeated injections of recombinantly-produced antibodies, which can provide various therapeutic effects via one or more mechanisms. The presence of the therapeutic antibodies in the body following administration is generally transient.

Efforts to develop immunotherapies targeting HIV and other viruses have not been entirely straightforward. Broadly neutralizing antibodies (BnAbs) have been isolated from sera and/or B cells from certain HIV-infected individuals. In individuals that produce them, BnAbs appear to be produced/maintained over time and to provide long-term protection. (Li, Y. et al. (2011) *Journal of virology*, 85(17): 8954-8967; Krumm, S. A. et al. (2016) *Retrovirology*, 13(1): 1; Kwong, P. D. et al. (2011). *Cold Spring Harbor perspectives in medicine*, 1(1):a007278). Certain of these broadly-neutralizing antibodies have shown promising results following passive transfer into infected individuals in animal models and, more recently, in human subjects. (Lu, C. L. et al. (2016). *Science*, 352(6288):1001-1004). Yet only a small percentage of infected individuals produce broadly-neutralizing antibodies, and efforts to induce their production in other individuals by vaccination have been largely unsuccessful. Gene delivery approaches (e.g., using AAV and other vectors) have also been explored to promote the expression and secretion of recombinant broadly-neutralizing antibodies in cells of a subject. (Balazs, A. B. et al. (2012). *Nature*, 481(7379): 81-84; Balazs, A. B. et al. (2014). *Nature medicine*, 20(3): 296) Some such approaches have successfully induced expression, but may be limited, for example, by the inability of the infected cells to persist long-term.

The engineered B cells described here provide a solution to address these shortcomings, and are generally applicable to any disease or condition that might benefit from antibody-based targeting approaches, or more broadly persistent, long-term expression of any therapeutic protein. Briefly, the provided embodiments involve engineering primary B cells (e.g., human B cells) to express a therapeutic protein, e.g. antibodies targeting one or more antigens/epitopes associated with a disease or condition of interest (e.g., in the case of HIV, to express broadly-neutralizing anti-HIV antibodies), or to express any protein that is therapeutic for treating a given disease or condition. As discussed in more detail below, the technology involves engineering the B cells in a way that promotes, or allows for the promotion of, (in a constitutive, transient and/or inducible manner) the production and/or secretion of an exogenous protein, such as recombinant antibodies or any other therapeutic protein. The technology also involves the administration of such engineered B cells to a subject in need of treatment for the disease or condition of interest, as well as formulations, compositions, and combinations including the cells, and methods of their production.

In some embodiments, the engineered B cells include secreting B cells or cells that are capable of differentiating into secreting B cells, such as memory B cells or progeny of a memory B cell. During B cell development, normally naïve B cells that are activated exhibit a transient ability to secrete IgM, and, following T cell help, can undergo immunoglobulin class switching to produce and secrete other immunoglobulins. In some aspects, such cells can become memory B cells that have ability to self-renew or result in cells that are more proficient at producing and secreting antibody (plasmablasts or plasma cells). In some aspects, memory B cells are filled with endoplasmic reticulum (ER), which, in some cases, is associated with the unfolded protein response associated with secretion.

The provided embodiments exploit the protein secretory machinery of the B cell, which, in some cases, is related to changes in the capacity of the endoplasmic reticulum that occurs in connection with the unfolded protein response in B cells. In some embodiments, the secretory capacity of B cells is related to their differentiation state and is a normal process of B cell development. Normally, B cells develop from hematopoietic stem cells (HSCs) that originate from bone marrow. HSCs first differentiate into multipotent progenitor (MPP) cells, then common lymphoid progenitor (CLP) cells. From here, their development into B cells occurs in several stages, each marked by various gene expression patterns and immunoglobulin H chain and L chain gene loci arrangements, the latter due to B cells undergoing V(D)J recombination as they develop. The progression of development from precursor B cells to immature B cells is as follows: early pro-B cell ($CD43^+$, $CD45^+$, $MHCII^+$), late-pro B cell ($CD43^+$, $CD45^+$, $CD19^+$, $CD40^+$, $MHCII^+$), large pre-B cell ($CD43^+$, $CD45^+$, $CD19^+$, $CD40^+$, $MHCII^+$), small pre-B cell ($CD45^+$, $CD19^+$, $CD40^+$, $MHCII^+$), and immature B cell ($CD45^+$, $CD19^+$, $CD40^+$, $IgM^+$, $MHCII^+$).

B cells undergo two types of selection while developing in the bone marrow to ensure proper development. Positive selection occurs through antigen-independent signaling involving both the pre-BCR and the BCR. If these receptors do not bind to their ligand, B cells do not receive the proper signals and cease to develop. Negative selection occurs through the binding of self-antigen with the BCR; If the BCR can bind strongly to self-antigen, then the B cell undergoes one of four fates: clonal deletion, receptor editing, anergy, or ignorance (B cell ignores signal and continues development). This negative selection process leads to a state of central tolerance, in which the mature B cells don't bind with self antigens present in the bone marrow.

To complete development, immature B cells migrate from the bone marrow to the spleen as well as pass through two transitional stages: T1 and T2 (CD45$^+$, CD19$^+$, CD40$^+$, IgM$^+$, IgD$^+$, CD21$^+$, MHCII$^+$). Throughout their migration to the spleen and after spleen entry, they are considered T1 B cells. Within the spleen, T1 B cells transition to T2 B cells. T2 B cells differentiate into either follicular (FO) B cells or marginal zone (MZ) B cells depending on signals received through the BCR and other receptors. While immature and during the T1 phase, B cells express BCR of class IgH, but BCR expression changes to the classes IgM and IgD after transition into the T2 phase and while mature up to activation.

Once differentiated, they are now considered mature B cells, or naïve B cells. Typical phenotypic markers of naïve mature B cells in humans may include one or more (such as all) of PAX5$^+$, BACH2$^+$, BCL-2$^+$, OBF1$^+$, OCT2$^+$, PU.1$^+$, SPIB$^+$, ETS1$^+$, IRF8$^-$, IRF4$^{low}$, BLIMP1$^+$, and XBP1$^-$, and typical surface markers in humans may include one or more (such as all) of CD19$^+$, CD20$^+$, CD21$^+$, CD22$^+$, CD23$^+$, CD24$^+$, CD10$^-$, CD27$^-$, and CD38$^{low}$.

Mature B cells can differentiate into plasmablasts, plasma cells, or memory B cells. Plasmablasts are short-lived, proliferating antibody-secreting cells.

Plasmablasts are generated early in an infection and their antibodies tend to have a weaker affinity towards their target antigen compared to plasma cell. Plasmablasts can result from T cell-independent activation of B cells or the extrafollicular response from T cell-dependent activation of B cells. Plasma cells are long-lived, non-proliferating antibody-secreting cells. There is evidence that B cells first differentiate into a plasmablast-like cell, then differentiate into a plasma cell. Typical phenotypic markers of plasmablasts in humans may include one or more (such as all) of PAX5$^-$, BACH2$^-$, BCL-2$^-$, OBF1$^-$, OCT2$^-$, PU.1$^-$, SPIB$^-$, ETS1$^-$, IRF8$^-$, IRF4$^{hi}$, BLIMP1$^{mid}$, and XBP1$^+$, and typical surface markers in humans may include one or more (such as all) of CD19$^+$, CD38$^{high}$, CD27$^{high}$, CD269$^+$, MHCII$^+$, CD20$^-$, and CD138$^-$.

Plasma cells are generated later in an infection and, compared to plasmablasts, have antibodies with a higher affinity towards their target antigen due to affinity maturation in the germinal center (GC) and produce more antibodies. Plasma cells typically result from the germinal center reaction from T cell-dependent activation of B cells, however they can also result from T cell-independent activation of B cells. Typical phenotypic markers of plasma cells in humans may include one or more (such as all) of PAX5$^-$, BACH2$^-$, BCL-2$^-$, OBF1$^-$, OCT2$^-$, PU.1$^-$, SPIB$^-$, ETSI$^-$, IRF8$^-$, IRF4$^{hi}$, BLIMP1$^{hi}$, and XBP1$^+$, and typical surface markers in humans may include one or more (such as all) of CXCR4$^+$, CD27$^+$, CD38$^{high}$, CD138$^+$, CD269$^+$, CD19$^{low}$, CD20$^-$, and MHCII$^{-/low}$.

Memory B cells are dormant B cells. Their function is to circulate through the body and initiate a stronger, more rapid antibody response (known as the secondary antibody response) if they detect the antigen that had activated their parent B cell (memory B cells and their parent B cells share the same BCR, thus they detect the same antigen). Memory B cells can be generated from T cell-dependent activation through both the extrafollicular response and the germinal center reaction as well as from T cell-independent activation of B1 cells. Typical phenotypic markers of memory B cells in humans may include one or more (such as all) of PAX5$^+$, BACH2$^+$, BCL-2$^+$, OBF1$^+$, OCT2$^+$, PU.1$^+$, SPIB$^+$, ETS1$^+$, IRF8$^+$, IRF4$^{low}$, BLIMP1$^-$, and XBP1$^-$, and typical surface markers in humans may include one or more (such as all) of CD19$^+$, CD20$^+$, CD40$^+$, CD27$^{var}$, CXCR4,5,7$^+$, CD23$^{low}$, and CD38$^-$.

In some embodiments, the provided engineered cells are memory cells, or have the ability to differentiate into memory cells, such as memory cells that have the ability to divide and reproduce to make a plasma cell. In some embodiments, the provided engineered cells further contain a receptor (such as a recombinant or chimeric receptor) to drive, such as induce or stimulate, a mitogenic or proliferative signal or a signal capable of modulating the differentiation of the B cell into a secreting B cell (also referred to herein as a driving receptor). In some embodiments, the driving receptor mimics the signaling ability of an endogenous B cell receptor (BCR). In some aspects, following a differentiation signal, expression of an integral membrane protein BCR can switch to expression of a secretory immunoglobulin by alternative poly(A) site usage that can lead to removal of the sequence encoding the transmembrane domain from the mRNA transcript. Further, in some aspects, the differentiation changes the secretion ability of the cell such that, for example, on a per cell basis a plasmablast or plasma cell has more synthetic capacity to secrete proteins due to a higher ER content.

Thus, in some embodiments, the engineered cells have, or are able to change or differentiate into cells that have, a higher capacity to synthesize proteins and/or a higher capacity to secrete proteins. In some embodiments, the driving receptor is an endogenous BCR that is responsive to a known ligand such as a vaccine or other ligand, e.g. tetanus-specific BCR responsive to a diphtheria tetanus vaccine. In some embodiments, the B cell is further engineered with an exogenous driving receptor that has the ability to induce a B cell signaling pathway, such as via an ITAM-containing intracellular signaling domain (e.g. CD79a or CD79b) in response to ligand binding, thereby inducing or stimulating a mitogenic or proliferative signal or a signal capable of modulating the differentiation of the B cell into a secreting B cell.

In some embodiments, the provided engineered B cells secrete the exogenous protein, such as a therapeutic protein. Also provided are compositions, methods and kits for using the engineered B cells in adoptive cell therapy methods for treating any disease or condition which the secretable exogenous protein, such as therapeutic protein, is known to or likely to treat or ameliorate.

II. Engineered B Cells

Provided herein are engineered B cells that express and secrete an exogenous protein, such as a therapeutic protein, including an antibody or antigen-binding fragment thereof. In some cases, such a therapeutic protein may target one or more pathways and/or molecules involved in a disease or condition, such as infectious disease, cancer, autoimmune disease or other disease or condition. In some cases, the engineered B cell may express and secrete a therapeutic antibody targeting a pathogen-derived antigen or a tumor- or cancer-associated antigen. In some aspects, expression of the exogenous protein in the engineered B cells is conditional, such as in inducible. In some aspects, expression of the exogenous protein in the engineered B cells is constitutive.

In some embodiments, the provided engineered B cells are those in which certain genes have been modified, including genes encoding an endogenous immunoglobulin, genes involved in production and/or secretion of the exogenous protein, and genes involved in B cell lineage determination.

In some embodiments, the provided engineered B cells also include those that express a driving receptor, such as a ligand-binding receptor, capable of inducing a mitogenic or proliferative signal or a signal capable of modulating the differentiation of the cell, such as upon ligand binding. In some embodiments, upon ligand binding, the receptor signals the engineered B cell to express and/or secrete the exogenous protein. In some embodiments, the driving receptor is an endogenous B cell receptor. In some embodiments, the driving receptor is an exogenous, such as recombinant or engineered, receptor, such as a chimeric receptor. In some embodiments, the engineered B cell includes a modification that results in reduced or disrupted expression of an endogenous B cell receptor. In some of the engineered B cells, the cells may be modified to prevent class-switching of an endogenous antibody and/or to prevent switching of the endogenous antibody from a membrane-anchored form to a secreted form. Such features in some aspects confer persistent, long-term delivery of the exogenous protein to an individual, for example in the context of adoptive cell therapy.

The cells generally are engineered by introducing one or more engineered nucleic acid molecules. The nucleic acid molecules encode an exogenous protein, such as a therapeutic protein, for example an antibody or antigen-binding fragment thereof. In some embodiments, the nucleic acid molecules do not encode an antibody or antigen-binding fragment thereof. In some of the engineered B cells, the nucleic acid is integrated into a targeted locus, such as an endogenous immunoglobulin locus. In other of the engineered B cells, the nucleic acid is integrated into a random locus. Also among the nucleic acids are those that further encode a receptor (e.g. driving receptor) described herein. Also provided are nucleic acids affecting expression of endogenous genes, such as by gene editing. For example, some such nucleic acids effect repression of expression and/or disruption of endogenous genes, or effect increased expression of endogenous genes.

In some embodiments, the engineered B cell comprises nucleic acid encoding an exogenous protein that is an antibody or antigen-binding fragment thereof. In some embodiments, the engineered B cell comprises nucleic acid encoding an exogenous protein that is not an antibody. In some embodiments, the exogenous protein is selected from blood factors, thrombolytic agents, hormones, growth factors, and cytokines (including chemokines, interferons, interleukins, lymphokines, and tumor necrosis factors).

In some embodiments, the engineered B cell comprises nucleic acid encoding an exogenous protein that is conditionally expressed. For example, in some embodiments, the nucleic acid comprises an inducible regulatory element operably linked to a sequence of nucleotides encoding the exogenous protein.

In some embodiments, the engineered B cell comprises nucleic acid encoding an exogenous protein and is modified to prevent class-switching of an endogenous antibody and/or to prevent switching of the endogenous antibody from a membrane-anchored form to a secreted form. For example, in some embodiments, the engineered B cell comprises one or more modifications that alter one or more proteins involved in regulating immunoglobulin class switching and/or the switch from a membrane-anchored form to a secreted form. In some embodiments, the engineered B cell comprises one or more modifications that alter one or more nucleotide sequences at the immunoglobulin locus involved in regulating immunoglobulin class switching and/or the switch from a membrane-anchored form to a secreted form.

In some embodiments, the engineered B cell comprises nucleic acid encoding an exogenous protein, wherein the nucleic acid is integrated into an endogenous immunoglobulin locus. For example, in some embodiments, the nucleic acid is inserted into or replaces all or a portion of an endogenous immunoglobulin locus, such as by homologous recombination. In some embodiments, the integration is facilitated by a designer nuclease.

In some embodiments, the engineered B cell comprises nucleic acid encoding an exogenous protein and is modified to increase the capacity of the cell to produce and/or secrete the exogenous protein. For example, in some embodiments, the engineered B cell is modified to alter the expression of one or more proteins involved in B cell lineage determination, or to adopt a phenotype of an antibody-secreting B cell, such as a plasmablast or plasma cell.

In some embodiments, the engineered B cell comprises nucleic acid encoding an exogenous protein and a receptor comprising a ligand binding domain, wherein upon ligand binding, the receptor is capable of inducing (i) a mitogenic or proliferative signal; and/or (ii) a signal that is capable of modulating the differentiation of the engineered B cell. In some embodiments, the receptor is a chimeric receptor. In some embodiments, the exogenous protein is a ligand-binding protein, and the receptor and exogenous protein do not bind the same ligand, or contain different ligand binding domains. In some embodiments, binding of ligand to the receptor increases expression and/or secretion of the exogenous protein.

In some aspects, features of the provided engineered B cells and methods avoid the transient availability of exogenous proteins delivered to a subject directly or engineered to be expressed in other cell types in the subject. For example, in some embodiments, they allow for persistent capacity to express and/or secrete the exogenous protein in a subject in the context of adoptive cell therapy, where the engineered B cells are long-lived, and/or can be induced to proliferate and/or secrete the exogenous protein, such as by binding a ligand associated with a disease or condition for which the exogenous protein provides a therapeutic benefit.

A. Cells

The starting population of cells used in the engineering methods may be derived from a number of sources. The starting cell population may be derived from PBMCs or other blood samples, tonsils, bone marrow or other like preparations in which B cells are present. In some aspects, the starting population of cells may include bulk (non-selected) B cells or a specific B cell subset, such as mature, immature, memory, naïve, or other B cell subset. In some embodiments, the starting cell population may comprise precursor cells capable of differentiating into B cells, such as hematopoietic stem cells (HSCs). With reference to the subject to be treated, the starting cells may be allogeneic and/or autologous. Among the methods include off-the-shelf methods. In some aspects, such as for off-the-shelf technologies, the starting cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of B cells are precursor or immature B cells, naïve mature B cells, memory B cells, plasmablasts, and plasma cells. Precursor or immature B cells include HSCs, multipotent progenitor (MPP) cells, common lymphoid progenitor (CLP) cells, early pro-B cells, late pro-B cells, large pre-B cells, small pre-B cells, immature B cells, T1 B cells, and T2 B cells.

In some embodiments, one or more of the B cell populations is enriched for or depleted of cells that are positive for (marker$^+$) or express high levels (marker$^{high}$) of one or more particular markers, such as surface markers, or that are negative for (marker$^-$) or express relatively low levels (marker$^{low}$) of one or more markers. In some cases, such markers are those that are absent or expressed at relatively low levels on certain populations of B cells (such as naïve cells) but are present or expressed at relatively higher levels on certain other populations of B cells (such as non-naïve cells).

In one embodiment, the cells are (1) enriched for (i.e., positively selected for) cells that are positive for or express high levels of one or more of (such as all of) PAX5, BACH2, BCL-2, OBF1, OCT2, PU.1, SPIB, ETS1, and IRF8 and/or depleted of (e.g., negatively selected for) cells that are positive for or express high levels of one or more of (such as all of) IRF4, BLIMP1, and XBP1; and/or (2) enriched for (i.e., positively selected for) cells that are positive for or express high surface levels of one or more of (such as all of) CD19, CD20, CD21, CD22, CD23, and CD24 and/or depleted of (e.g., negatively selected for) cells that are positive for or express high surface levels of one or more of (such as all of) CD10, CD27, and CD38. In some embodiments, the cells are enriched for naïve mature B cells.

In one embodiment, the cells are (1) enriched for (i.e., positively selected for) cells that are positive for or express high levels of one or more of (such as all of) IRF4, BLIMP1, and XBP1 and/or depleted of (e.g., negatively selected for) cells that are positive for or express high levels of one or more of (such as all of) PAX5, BACH2, BCL-2, OBF1, OCT2, PU.1, SPIB, ETS1, and IRF8; and/or (2) enriched for (i.e., positively selected for) cells that are positive for or express high surface levels of one or more of (such as all of) CD19, CD38, CD27, CD269, and MHCII and/or depleted of (e.g., negatively selected for) cells that are positive for or express high surface levels of CD20 and/or CD138. In some embodiments, the cells are enriched for plasmablasts.

In one embodiment, the cells are (1) enriched for (i.e., positively selected for) cells that are positive for or express high levels of one or more of (such as all of) IRF4, BLIMP1, and XBP1 and/or depleted of (e.g., negatively selected for) cells that are positive for or express high levels of one or more of (such as all of) PAX5, BACH2, BCL-2, OBF1, OCT2, PU.1, SPIB, ETS1, and IRF8; and/or (2) enriched for (i.e., positively selected for) cells that are positive for or express high surface levels of one or more of (such as all of) CXCR4, CD27, CD38, CD138, and CD269 and/or depleted of (e.g., negatively selected for) cells that are positive for or express high surface levels of one or more of (such as all of) CD19, CD20, and MHCII. In some embodiments, the cells are enriched for plasma cells.

In one embodiment, the cells are (1) enriched for (i.e., positively selected for) cells that are positive for or express high levels of one or more of (such as all of) PAX5, BACH2, BCL-2, OBF1, OCT2, PU.1, SPIB, ETS1, and IRF8 and/or depleted of (e.g., negatively selected for) cells that are positive for or express high levels of one or more of (such as all of) IRF4, BLIMPL and XBP1; and/or (2) enriched for (i.e., positively selected for) cells that are positive for or express high surface levels of one or more of (such as all of) CD19, CD20, CD40, CXCR4, CXCR5, and CXCR7 and/or depleted of (e.g., negatively selected for) cells that are positive for or express high surface levels of CD23 and/or CD38. In some embodiments, the cells are enriched for memory B cells.

B. Nucleic Acid Encoding Exogenous Protein

In some embodiments, the engineered B cells comprise one or more nucleic acids comprising one or more coding sequences encoding an exogenous protein introduced via genetic engineering. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types. In some embodiments, at least some of the one or more coding sequences are codon-optimized for a particular organism, such as humans. In some embodiments, at least some of the one or more coding sequences do not comprise intronic sequences. In some embodiments, at least some of the one or more coding sequences do not comprise sequences encoding a transmembrane domain.

Any of the exogenous proteins described herein can be encoded by polynucleotides containing one or more nucleic acid molecules encoding the exogenous protein, in any combinations or arrangements. For example, one, two, three or more polynucleotides can encode one, two, three or more different polypeptide chains contained in the exogenous protein. In some embodiments, one vector or construct comprises nucleic acid molecules encoding one or more polypeptide chains contained in the exogenous protein, and one or more separate vectors or constructs comprise nucleic acid molecules encoding one or more additional polypeptide chains contained in the exogenous protein. Each of the nucleic acid molecules can also encode one or more marker(s), such as a surface marker. In some embodiments, the one or more marker(s) is a transduction marker, surrogate marker and/or a selection marker.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO:5 or 207) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, or epidermal growth factor receptor (e.g., tEGFR).

In some embodiments, the marker is or comprises a fluorescent protein, such as green fluorescent protein (GFP), enhanced green fluorescent protein (EGFP), such as superfold GFP (sfGFP; set forth in SEQ ID NO:208), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from E. coli, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In certain cases where nucleic acid molecules encode two or more different polypeptide chains, each of the polypeptide chains can be encoded by a separate nucleic acid molecule. For example, two separate nucleic acids are provided, and each can be individually transferred or introduced into the cell for expression in the cell.

In some embodiments, the nucleic acid molecule is a single polynucleotide encoding a plurality of different polypeptide chains. In some embodiments, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g. encoding one or more chains of an exogenous protein for secretion) by a message from a single promoter.

In some embodiments, a single promoter may direct expression of an RNA that contains, in a single open reading frame (ORF), two or three genes (e.g. encoding different polypeptide chains of the exogenous protein) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and system disclosed herein, without limitation, include 2A sequences from the foot-and-mouth disease virus (F2A, e.g., SEQ ID NO: 4), equine rhinitis A virus (E2A, e.g., SEQ ID NO: 3), Thosea asigna virus (T2A, e.g., SEQ ID NO: 1 or 205), and porcine teschovirus-1 (P2A, e.g., SEQ ID NO: 2 or 206) as described in U.S. Patent Publication No. 20070116690.

In some embodiments, the nucleic acids encoding the marker and the nucleic acid encoding the recombinant receptor are operably linked to two different promoters.

Also provided herein are vectors and constructs comprising the nucleic acid molecules.

Also provided are compositions containing one or more of the nucleic acid molecules, vectors or constructs, such as any described herein. In some embodiments, the nucleic acid molecules, vectors, constructs or compositions can be used to engineer cells, such as B cells, to express any of the exogenous proteins and/or recombinant receptors described herein.

I. Therapeutic Proteins

Among the exogenous proteins are blood factors, thrombolytic agents, hormones, growth factors, cytokines, and antibodies or antigen-binding fragments thereof. In some embodiments, the cytokines include, without limitation, chemokines, interferons, interleukins, lymphokines, and tumor necrosis factors. In some embodiments, the exogenous protein is a therapeutic protein useful for treating and/or preventing a disease or condition in an individual.

Exemplary blood factors include Factor I, Factor II, Factor III, Factor IV, Factor V, Factor VI, Factor VII, Factor VIII, Factor IX, Factor X, Factor XI, Factor XII, and Factor XIII In some embodiments, the blood factor is therapeutic for treating and/or preventing a disease or condition, such as any of the diseases or conditions described herein.

Exemplary thrombolytic agents include streptokinase, urokinase, and tissue plasminogen activator. In some embodiments, the tissue plasminogen activator is selected from alteplase, reteplase, or tenecteplase. In some embodiments, the thrombolytic agent is therapeutic for treating and/or preventing a disease or condition, such as any of the diseases or conditions described herein.

Exemplary hormones include insulin, glucagon, growth hormone, and gonadotropins. In some embodiments, the gonadotropin is selected from follicle-stimulating hormone (FSH), luteinizing hormone (LH), and human chorionic gonadotropin (hCG). In some embodiments, the hormone is therapeutic for treating and/or preventing a disease or condition, such as any of the diseases or conditions described herein.

Exemplary growth factors include granulocyte colony-stimulating factor (G-CSF), granulocyte-macrophage colony-stimulating factor (GM-CSF), bone morphogenetic proteins (BMPs), erythropoietin, and thrombopoietin. In some embodiments, the BMP is selected from BMP1, BMP2, BMP3, BMP4, BMP5, BMP6, BMP6, BMP8a, BMP8b, BMP10, or BMP15. In some embodiments, the growth factor is therapeutic for treating and/or preventing a disease or condition, such as any of the diseases or conditions described herein.

Exemplary chemokines include CC chemokines (CCL1, CCL2, and the like), CXC chemokines (CXCL1, CXCL2, and the like), C chemokines (XCL1 and XCL2), and CX3C chemokines (CX3CL1). In some embodiments, the chemokine is therapeutic for treating and/or preventing a disease or condition, such as any of the diseases or conditions described herein.

Exemplary interferons include interferons-α, -β, and -γ. In some embodiments, the exogenous protein is selected from interferon alpha 2a, interferon alpha 2b, human leukocyte interferon-alpha (HuIFN-alpha-Le), interferon beta 1a, interferon beta 1b, of interferon gamma 1b. In some embodiments, the interferon is therapeutic for treating and/or preventing a disease or condition, such as any of the diseases or conditions described herein.

Exemplary interleukins include interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-16 (IL-16), interleukin-17 (IL-17), interleukin-18 (IL-18), interleukin-19 (IL-19), interleukin-20 (IL-20), interleukin-21 (IL-21), interleukin-22 (IL-22), interleukin-23 (IL-23), interleukin-24 (IL-24), interleukin-25 (IL-25), interleukin-26 (IL-26), interleukin-27 (IL-27), interleukin-28 (IL-28), interleukin-29 (IL-29), interleukin-30 (IL-30), interleukin-31 (IL-31), interleukin-32 (IL-32), interleukin-33 (IL-33), interleukin-35 (IL-35), and interleukin-36 (IL-36). In some embodiments, the interleukin is selected from IL-1, IL-1α, IL-1β, IL-2, IL-3, IL-4, IL-6, IL-8, IL-10, IL-11, IL-12, IL-13, or IL-18. In some embodiments, the interleukin is therapeutic for treating and/or preventing a disease or condition, such as any of the diseases or conditions described herein.

Exemplary tumor necrosis factors include tumor necrosis factor alpha (TNFα), lymphotoxin alpha (LTα), lymphotoxin beta (LTβ), CD40L, CD27L, CD30L, FASL, 4-1BBL, OX40L, and TNF-related apoptosis inducing ligand (TRAIL). In some embodiments, the tumor necrosis factor is therapeutic for treating and/or preventing a disease or condition, such as any of the diseases or conditions described herein.

Antibodies

In some embodiments, the exogenous protein is an antibody or antigen-binding fragment thereof. In some embodiments, the exogenous protein is or includes an antigen-binding portion or portions of an antibody molecule, such as a single-chain antibody fragment (scFv) derived from the variable heavy ($V_H$) and variable light ($V_L$) chains of a monoclonal antibody (mAb).

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda.

In some embodiments, the exogenous protein is an antibody fragment. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150:880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the exogenous protein comprises an antibody heavy chain domain that specifically binds an antigen, such as a cancer marker, viral antigen, or cell surface antigen of a cell or disease to be targeted, such as a virally-infected cell, a tumor cell, or a cancer cell, such as any of the target antigens described herein or known in the art.

Antibody fragments can be made by various techniques, including but not limited to proteolytic digestion of an intact antibody, as well as production by recombinant methods. In some embodiments, the antibodies are recombinantly-produced fragments, such as fragments comprising arrangements that do not occur naturally, such as those with two or more antibody regions or chains joined by synthetic linkers, e.g., peptide linkers, and/or that are not produced by digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, the exogenous protein is or comprises an antibody or an antigen-binding fragment (e.g. scFv) that specifically recognizes a ligand, e.g., an antigen, such as an intact antigen expressed on the surface of a cell, or a soluble ligand, e.g., an antigen, such as any as described herein.

In some embodiments, the exogenous protein, such as an antibody or antigen-binding fragment (e.g. scFv) may contain at least a portion of an immunoglobulin constant region, such as one or more constant region domain. In some embodiments, the constant regions include a light chain constant region and/or a heavy chain constant region 1 (CH1). In some embodiments, the antibody includes a CH2 and/or CH3 domain, such as an Fc region. In some embodiments, the Fc region is an Fc region of a human IgG, such as an IgG1 or IgG4.

In some embodiments, the Fc domain contains a modification (e.g., substitution) such that the interface of the Fc molecule is modified to facilitate and/or promote heterodimerization. In some embodiments, the modifications contain a knob-into-hole (KiH) or dock and lock (DNL) modification(s). In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides Amino acids targeted for replacement and/or modification to create protuberances or cavities in a polypeptide are typically interface amino acids that interact or contact with one or more amino acids in the interface of a second polypeptide.

The CH3 interface of human IgG1, for example, involves sixteen residues on each domain located on four anti-parallel β-strands which buries 1090 Å2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731, 168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

In some embodiments, the heterodimeric molecule contains a T366W mutation in the CH3 domain of the "knobs chain" and T366S, L368A, Y407V mutations in the CH3 domain of the "hole chain". In some cases, an additional interchain disulfide bridge between the CH3 domains can also be used (Merchant, A. M., et al., Nature Biotech. 16 (1998) 677-681) e.g. by introducing a Y349C mutation into the CH3 domain of the "knobs" or "hole" chain and a E356C mutation or a S354C mutation into the CH3 domain of the other chain. In some embodiments, the heterodimeric molecule contains S354C, T366W mutations in one of the two CH3 domains and Y349C, T366S, L368A, Y407V mutations in the other of the two CH3 domains. In some embodiments, the heterodimeric molecule comprises E356C, T366W mutations in one of the two CH3 domains and Y349C, T366S, L368A, Y407V mutations in the other of the two CH3 domains. In some embodiments, the heterodimeric molecule comprises Y349C, T366W mutations in one of the two CH3 domains and E356C, T366S, L368A, Y407V mutations in the other of the two CH3 domains. In some embodiments, the heterodimeric molecule comprises Y349C, T366W mutations in one of the two CH3 domains and S354C, T366S, L368A, Y407V mutations in the other of the two CH3 domains. Examples of other knobs-in-holes technologies are known, such as those described in EP 1 870 459 A1.

In some embodiments of the engineered B cell described herein, the one or more nucleic acid molecules comprise one or more coding sequences comprising a first coding sequence encoding a first polypeptide comprising a heavy chain antibody sequence and, optionally, a second coding sequence encoding a second polypeptide comprising a light chain antibody sequence. In some embodiments, the first polypeptide comprises a heavy chain variable domain sequence and/or the second polypeptide comprises a light chain variable domain sequence. In some embodiments, the first polypeptide comprises a full-length heavy chain antibody sequence and/or the second polypeptide comprises a full-length light chain antibody sequence. In some embodiments, the first and second coding sequences are contained in separate nucleic acid molecules, and the exogenous protein comprises the first and second polypeptides contained in separate polypeptide chains. In some embodiments, the one or more nucleic acid molecules comprise a single nucleic acid molecule comprising the first and second coding sequences. In some embodiments, the single nucleic acid molecule comprises a nucleotide linker linking the first and second coding sequences. In some embodiments, the nucleotide linker encodes a peptide linker, and the exogenous protein comprises a single polypeptide chain comprising the first polypeptide and the second polypeptide linked by the peptide linker. In some embodiments, the nucleotide linker is or comprises an internal ribosome entry site (IRES), or is or comprises a nucleotide sequence encoding a self-cleaving peptide or a peptide that causes ribosome skipping, including, without limitation, a P2A, a T2A, an E2A, and an F2A, and the exogenous protein comprises the first and second polypeptides contained in separate polypeptide chains.

Antigens targeted by the exogenous protein (e.g., an antibody or antigen-binding fragment thereof) in some embodiments include cancer- or tumor-associated antigens. In some embodiments, the antigen is selected from among antigens associated with hematological cancers including, without limitation, leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, plasmacytoma, Waldenstrom's macroglobulinemia, heavy chain disease, myelodysplastic syndrome, hairy cell leukemia and myelodysplasia.

In some embodiments, the antigen is selected from among antigens associated with solid tumors including, without limitation, sarcomas and carcinomas, including adrenocortical carcinoma, cholangiocarcinoma, fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, stomach cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, thyroid cancer (e.g., medullary thyroid carcinoma and papillary thyroid carcinoma), pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer (e.g., cervical carcinoma and pre-invasive cervical dysplasia), colorectal cancer, cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, esophageal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, kidney cancer, melanoma, cancer of the uterus (e.g., endometrial carcinoma), urothelial cancers (e.g., squamous cell carcinoma, transitional cell carcinoma, adenocarcinoma, ureter cancer, and urinary bladder cancer), and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Exemplary exogenous proteins (e.g., antibodies or antigen-binding fragments thereof) include exogenous proteins that bind to a tumor- or cancer-associated antigen, such as a molecule selected from among carbonic anhydrase IX, alpha-fetoprotein, alpha-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1alpha, colon-specific antigen-p (CSAp), CEA (CEACAM5), CEACAM6, c-met, DAM, EGFR, EGI-RvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-gamma, IFN-alpha, IFN-beta, IL-2, IL-4R, IL-6R, IL-13R, IL-15R, IL-17R, IL-18R, IL-6, IL-8, IL-12, IL-15, IL-7, IL-18, IL-25, insulin-like growth factor-1 (IGF-1), KC4-antigen, KS-1-antigen, KS 1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, PIGF, ILGF, ILGF-1R, IL-6, IL-25, RSS, RANTES, T101, SAGE, 5100, survivin, survivin-2B, TAC, TAG-72, tenascin, TRAIL receptors, TNF-alpha, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207).

In some embodiments, the exogenous protein is an antibody or antigen-binding fragment thereof derived from alemtuzumab, atezolizumab, basiliximab, bevacizumab (Avastin®), blinatumomab, brentuximab vedotin, catumaxomab, cetuximab, daclizumab (Zenapax), daratumumab, denosumab, dinutuximab, elotuzumab, gemtuzumab (Mylotarg), ibritumomab tiuxetan (Zevalin), ipilimumab, necitumumab, nimotuzumab, nivolumab, obinutuzumab, ofatumumab, panitumumab, pembrolizumab, pertuzumab, pidilizumab (CT-011), ramucirumab, rituximab (Rituxan, Mabthera), siltuximab, tositumomab (Bexxar®), trastuzumab, ado-trastuzumab emtansine, zalutumumab, CEA-scan Fab fragment, OC125 monoclonal antibody, ab75705, B72.3, MPDL3280A, MSB001078C, or MEDI4736. In some embodiments, the antibody or antigen-binding fragment thereof is therapeutic for treating and/or preventing a disease or condition.

Also included are exogenous proteins (e.g., antibodies or antigen-binding fragments) that bind to pathogen-associated (such as virally-encoded) antigens, including, without limitation, antigens derived from *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, *Astroviridae*, *Babesia* genus, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia* genus, *Borrelia* spp, *Brucella* genus, *Brugia malayi*, Bunyaviridae family, *Burkholderia cepacia* and other *Burkholderia* species, *Burkholderia mallei*, *Burkholderia pseudomallei*, Caliciviridae family, *Campylobacter* genus, *Candida albicans*, *Candida* spp, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium* spp, *Clostridium tetani*, *Coccidioides* spp, coronaviruses, *Corynebacterium diphtheriae*, *Coxiella burnetii*, Crimean-Congo hemorrhagic fever virus, *Cryptococcus neoformans*, *Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis*, *Ehrlichia ewingii*, *Ehrlichia* genus, *Entamoeba histolytica*, *Enterococcus* genus, *Enterovirus* genus, *Enteroviruses*, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis*, *Fusobacterium* genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Human T cell leukemia virus 1 (HTLV-1), Japanese encephalitis virus, JC virus, Junin virus, Kaposi's Sarcoma associated herpesvirus (KSHV), *Kingella kingae, Klebsiella granulomatis*, Kuru prion, Lassa virus, *Legionella pneumophila, Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai, Microsporidia phylum, Molluscum contagiosum* virus (MCV), Mumps virus, *Mycobacterium leprae* and *Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi*, Orthomyxoviridae family (Influenza), *Paracoccidioides brasiliensis, Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari, Rickettsia* genus, *Rickettsia prowazekii, Rickettsia rickettsii, Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia* genus, *Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum, Varicella zoster* virus (VZV), *Varicella zoster* virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica, Yersinia pestis*, or *Yersinia pseudotuberculosis*.

In some embodiments, the exogenous protein is an antibody or antigen-binding fragment thereof that binds to an HIV-associated antigen, such as a molecule selected from among HIV Gag polyprotein (p55), HIV Pol polyprotein, HIV Gag-Pol precursor (p160), HIV matrix protein (MA, p17), HIV capsid protein (CA, p24), HIV spacer peptide 1 (SP1, p2), HIV nucleocapsid protein (NC, p9), HIV spacer peptide 2 (SP2, p1), HIV P6 protein, HIV reverse transcriptase (RT, p50), HIV RNase H (p15), HIV integrase (IN, p31), HIV protease (PR, p10), HIV Env (gp160), gp120, gp41, HIV transactivator (Tat), HIV regulator of expression of virion proteins (Rev), HIV lentivirus protein R (Vpr), HIV Vif, HIV negative factor (Nee, and HIV virus protein U (Vpu). In some embodiments, the HIV-associated antigen is an HIV-1 and/or HIV-2 associated antigen.

In some embodiments, the exogenous protein is an antibody or antigen-binding fragment thereof derived from a neutralizing (such as broadly neutralizing) antiviral antibody. In some embodiments, the antibody or antigen-binding fragment thereof is derived from a neutralizing (such as broadly neutralizing) anti-HIV antibody. In some embodiments, the antibody or antigen-binding fragment thereof is capable of binding to HIV-1 and/or HIV-2. In some embodiments, the antibody or antigen-binding fragment thereof is capable of neutralizing one or more groups of HIV-1. Exemplary HIV-1 groups include HIV-1 Group M, HIV-1 Group N, HIV-1 Group O, and HIV-1 Group P. In some embodiments, the antibody or antigen-binding fragment thereof is capable of neutralizing one or more, including at least one, at least two, at least three, at least four, at least five, or more, subtypes, and/or recombinant forms thereof, of HIV-1. Subtypes and recombinant forms thereof are known; exemplary subtypes include subtype A (including A1 and A2), subtype B, subtype C, and recombinant forms including CRF_AE. In some embodiments, the antibody or antigen-binding fragment thereof is capable of neutralizing one or more groups, including subtypes thereof, of HIV-2. Exemplary HIV-2 groups include HIV-2 Group A, HIV-2 Group B, HIV-2 Group C, HIV-2 Group D, HIV-2 Group E, HIV-2 Group F, HIV-2 Group G, and HIV-2 Group H. In some embodiments, the broadly neutralizing anti-HIV antibody targets an epitope of gp160. In some embodiments, the broadly neutralizing anti-HIV antibody targets an epitope of gp120. In some embodiments, the broadly neutralizing anti-HIV antibody targets the high-mannose patch centered around the glycan at position 332 of gp120. In some embodiments, the broadly neutralizing anti-HIV antibody targets the CD4-binding site (CD4bs) of gp120. In some embodiments, the broadly neutralizing anti-HIV antibody targets an epitope of gp41. In some embodiments, the broadly neutralizing anti-HIV antibody targets the membrane-proximal external region (MPER) of gp41. In some embodiments, the broadly neutralizing anti-HIV antibody is, or is derived from, a molecule selected from among 10-1074, 10E8, 12A12, 12A21, 2F5, 35022, 3BC176, 3BNC117, 3BNC55, 3BNC60, 3BNC62, 447-52D, 4E10, 5H/I1-BMV-D5, 8ANC131, 8ANC134, 8ANC195, b12, M66.6, CAP206-CH12, 10E8 I, PG6, PG16, CH01, CH02, CH03, CH04, 2G12, PCDN-33A, PCDN-33B, PCDN-38A, PG16, PG9, PGDM1400, PGDM1401, PGDM1402, PGDM1403, PGDM1404, PGDM1405, PGDM1406, PGDM1407, PGDM1408, PGDM1409, PGDM1410, PGDM1411, PGDM1412, PGT121, PGT122, PGT123, PGT124, PGT125, PGT126, PGT127, PGT128, PGT129, PGT130, PGT131, PGT132, PGT133, PGT134, PGT135, PGT136, PGT137, PGT141, PGT142, PGT143, PGT144, PGT145, PGT151, PGT152, HJ16, CH103, CH104, CH105, CH106, HGN194, HJ16, HK20, VRC01, VRC02, VRC03, VRC07, VRC23, VRC-PG04, VRC-PG04b, VRC-PG20, VRC-CH30, VRC-CH31, VRC-CH32, VRC-CH33, VRC-CH34, NIH45-46, 1NC9, 1B2530, and Z13. See, for example, Pritchard, L. K. et al. (2015). *Nature communications,* 6; Sok, D., et al. (2013). *PLoS Pathog,* 9(11), e1003754; Sok, D., et al. (2014). *Science translational medicine,* 6(236), 236ra63-236ra63; Doores, K. J., et al. (2015). *Journal of virology,* 89(2), 1105-1118; and Falkowska, E., et al. (2014). *Immunity,* 40(5), 657-668. In some embodiments, the exogenous protein is a fragment of any of the aforementioned anti-HIV antibodies.

The exogenous protein may also be any circulating protein whose deficiency in an individual is associated with a disease or condition. In some embodiments, the exogenous protein is a functional form of a non-functional circulating protein expressed in an individual.

2 Regulatory Sequences

In some embodiments of an engineered B cell described herein, expression of the exogenous protein is under the control of a B cell-specific promoter and/or enhancer. In some embodiments, the B cell-specific promoter directs specific transgene expression in B cells. For example, a B cell-specific promoter may be capable of directing expression of an exogenous protein in plasmablasts and/or plasma cells. Another non-limiting example of a B cell-specific promoter is a promoter capable of directing expression of an exogenous protein throughout B-cell development from hematopoietic cells in primary and secondary lymphoid organs. In some embodiments, a B cell-specific promoter is capable of driving expression of an exogenous protein without affecting B-cell development. It is not intended that the methods or systems disclosed herein be limited by the source of the B cell-specific promoter. In some embodiments, a B cell-specific promoter may be the promoter/enhancer sequence of any B-cell specific genes, and/or variants or engineered portions thereof, that normally controls the expression of genes expressed in a B-cell, examples of which include, but are not limited to, promoters/enhancers of CD19, CD20, CD21, CD22, CD23, CD24, CD40, CD72, Blimp-1, CD79b (also known as B29 or Ig beta), mb-1 (also known as Ig alpha), IRF4, XBP1, tyrosine kinase blk, VpreB, immunoglobulin heavy chain, immunoglobulin kappa light chain, immunoglobulin lambda light chain, immunoglobulin J-chain, etc. In some embodiments of an engineered B cell described herein, expression of the exogenous protein is under the control of an immunoglobulin promoter and/or enhancer. In some embodiments, the immunoglobulin promoter and/or enhancer is a heavy chain promoter and/or enhancer, a kappa light chain promoter and/or enhancer, or a lambda light chain promoter and/or enhancer.

In some embodiments, the immunoglobulin promoter and/or enhancer is a heavy chain promoter and/or enhancer selected from among a heavy chain variable region promoter, an intronic enhancer (Eμ), and one or more enhancers contained in an IgH 3' regulatory region (3' RR). In some embodiments, the heavy chain variable region promoter comprises an octamer element. In some embodiments, the octamer element comprises the nucleotide sequence of SEQ ID NO: 203. In some embodiments, the Eμ enhancer comprises a core element (cEμ) and optionally one or two flanking nuclear matrix attachment regions (MARs). In some embodiments, the Eμ comprises the nucleotide sequence of SEQ ID NO: 204, or a variant thereof that exhibits at least 85%, 86%, 87%, 88%, 89%, 90%, 91%, 92%, 93%, 94%, 95%, 96%, 97%, 98%, 99% or more sequence identity to SEQ ID NO: 204. See for example Grosschedl, R., & Whitehead, D. B. (1985) *Cell*, 41(3): 885-897, Ernst, P., & Smale, S. T. (1995) *Immunity* 2(5): 427-438; Nikolajczyk, B. S. et al. (1999) *Cold Spring Harbor symposia on quantitative biology* (Vol. 64, pp. 99-108); Laumen, H. et al. (2000) *European journal of immunology* 30(2): 458-469; Ju, Z. et al. (2007) *Journal of Biological Chemistry* 282(48): 35169-35178.

In some embodiments, the immunoglobulin promoter and/or enhancer is a light chain promoter and/or enhancer selected from among a light chain variable region promoter, a kappa light chain intronic enhancer (Eκ), a lambda light chain intronic enhancer (Eλ), a kappa light chain 3' enhancer (3' Eκ), a lambda light chain 3' enhancer (3'Eλ). In some embodiments, the light chain variable region promoter comprises an octamer element. In some embodiments, the octamer element comprises the nucleotide sequence of SEQ ID NO: 203. In some embodiments, the Eκ enhancer comprises a core element (cEκ) and optionally one or two flanking MARs.

In some embodiments of an engineered B cell described herein, expression of the exogenous protein is constitutive. In some embodiments, the expression is under the control of a constitutively active promoter. In some embodiments, the promoter is selected from an RNA pol I, pol II or pol III promoter. In some embodiments, the promoter is selected from: a pol III promoter that is a U6 or an H1 promoter; or a pol II promoter that is a CMV, a SV40 early region or an adenovirus major late promoter. In some embodiments, the promoter is selected from SV40, CMV, UBC, EF1A, PGK, or CAGG.

In some embodiments of an engineered B cell described herein, expression of the exogenous protein is conditional. In some embodiments, the expression is under the control of a conditional promoter or enhancer or transactivator. In some embodiments, the conditional promoter or enhancer or trans activator is an inducible promoter, enhancer or transactivator or a repressible promoter, enhancer or transactivator. In some embodiments, the conditional promoter is an inducible promoter. In some embodiments, the promoter includes a Lac operator sequence, a tetracycline operator sequence, a galactose operator sequence, a doxycycline operator sequence, or analogs thereof. In some examples, the inducible promoter comprises a tetracycline response element (TRE). In some examples, the conditional promoter or enhancer or transactivator permits expression of the provided recombinant receptors upon the presence of the required condition, such as presence of an inducer, e.g., tetracycline or doxycycline, and the presence of the corresponding transcription factor for the promoter, enhancer or activator. In some examples, the corresponding transcription factor is naturally present in the engineered B cell. In other examples, a nucleic acid encoding the corresponding transcription factor is also introduced into the engineered B cell. In some embodiments, the promoter is a repressible promoter. In some embodiments, the promoter includes a Lac repressible element or a tetracycline repressible element.

3. Signal Sequences

In some embodiments of an engineered B cell described herein, the one or more coding sequences encoding the exogenous protein comprises a signal sequence coding region (SSCR) encoding a signal sequence fused to the exogenous protein. In some embodiments, a signal sequence is a polypeptide sequence or combination of sequences that are sufficient to mediate the translocation of a polypeptide to the cell surface. Translocation of a polypeptide to the cell surface is mediated by the secretory pathway, including the translocation of a polypeptide from the cytosol to the endoplasmic reticulum, and the subsequent transport of the polypeptide through the golgi apparatus, and to the cell membrane, where, for proteins lacking a transmembrane domain as is the case for the provided encoded exogenous proteins, the protein can be secreted from the cell.

In some embodiments, a signal sequence includes naturally-occurring and synthetic signal sequences. Examples of signal peptides include, but are not limited to, the endogenous signal peptides for immunoglobulin heavy and light chains and variants thereof (see for example Haryadi, R., et al. (2015) *PloS one*, 10(2): e0116878); the endogenous signal peptide for HGH and variants thereof; the endogenous signal peptide for interferons and variants thereof, including the signal peptide of type I, II and III interferons and variants thereof; and the endogenous signal peptides for known cytokines and variants thereof, such as the signal peptide of erythropoietin (EPO), insulin, TGF-β1, TNF, IL1-α, and IL1-β, and variants thereof. In some embodiments, the signal peptide is a modified HGH signal peptide. Exemplary Homo sapiens signal sequences can be found, for example, in U.S. Patent Publication No. US20130316366. In some embodiments, the one or more coding sequences encoding the exogenous protein comprise a SSCR encoding a signal sequence selected from among SEQ ID NOs: 76-202 such that the signal sequence is fused to the exogenous protein to allow for secretion.

4. Methods of Introducing Nucleic Acid into Cells

In some embodiments, the nucleic acids described herein are transferred into cells (such as B cells or B cell precursors) using recombinant infectious virus particles, such as, e.g., vectors derived from simian virus 40 (SV40), adenoviruses, or adeno-associated virus (AAV). In some embodiments, the nucleic acids are transferred into cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November; 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SH-V), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, the nucleic acids described herein are transferred into cells (such as B cells or B cell precursors) via electroporation (see, e.g., Chicaybam et al., (2013) PLoS ONE 8(3): e60298 and Van Tedeloo et al. (2000) Gene Therapy 7(16): 1431-1437). In some embodiments, the nucleic acids are transferred into cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the genetically engineered nucleic acids encoding the exogenous protein include those described, e.g., in international patent application Publication No.: WO2014055668, and U.S. Pat. No. 7,446,190.

In some embodiments, the nucleic acid described herein is integrated into a random locus in the engineered B cell. In some embodiments, the nucleic acid is inserted into the random locus. In some embodiments, the nucleic acid replaces all or a portion of the random locus. Techniques for introduction of a transgene using genetic engineering, such as by viral transduction, are well known. See for example WO9429438, WO9533824, WO9712052, WO200111067, WO200218609, WO2013014537, and WO2014026110.

In some embodiments, the nucleic acid described herein is integrated into a target locus in the engineered B cell. In some embodiments, the nucleic acid comprises sequences that allow for integration at the target locus by homologous recombination. In some embodiments, the nucleic acid comprises flanking sequences that are homologous to sequences at the target locus. In some embodiments, the nucleic acid is inserted into the target locus. In some embodiments, the nucleic acid replaces all or a portion of the target locus. In some embodiments, integration into the target locus is mediated by a designer nuclease selected from zinc-finger nucleases (ZFNs), transcription activator-like effector nucleases (TALENs), or RNA-guided nucleases (RGNs). In some embodiments, the RGN is a clustered, regularly interspaced, short palindromic repeats (CRISPR)-associated Cas9 (CRISPR-Cas9) nuclease. Techniques for using CRISPR/Cas9-mediate gene knock-in are known in the art. See for example Auer, T. O. et al. (2014) *Genome research* 24(1): 142-153; Kimura, Y., et al. (2014) *Scientific reports*, 4; Aida, T., et al. (2015) *Genome biology*, 16(1): 1; and Park, A., et al. (2014) *PloS one*, 9(4): e95101.

In some embodiments, the nucleic acid described herein is integrated into a target locus in the engineered B cell, wherein the target locus is an immunoglobulin locus. In some embodiments, the immunoglobulin locus is selected from a heavy chain immunoglobulin locus, a kappa light chain immunoglobulin locus, or a lambda light chain immunoglobulin locus. In some embodiments, the nucleic acid is integrated in the immunoglobulin locus such that the endogenous immunoglobulin encoded by the locus cannot be expressed. In some embodiments, the nucleic acid is integrated in the immunoglobulin locus such that the endogenous immunoglobulin encoded by the locus can still be expressed. In some embodiments, the nucleic acid is inserted in the immunoglobulin locus without replacing any sequences. In some embodiments, the nucleic acid is inserted upstream of the coding sequences in the immunoglobulin locus. In some embodiments, the nucleic acid is operably linked to a promoter and/or enhancer at the immunoglobulin locus. In some other embodiments, the nucleic acid replaces all or a portion of the immunoglobulin locus, such as all or a portion of the immunoglobulin locus coding sequences. In some embodiments, the nucleic acid replaces all or most of the immunoglobulin locus, and comprises regulatory sequences sufficient for expression of the exogenous protein. In some embodiments, the nucleic acid replaces a portion of the immunoglobulin locus, such as a portion of a coding sequence in the immunoglobulin locus. In some embodiments, the nucleic acid does not replace one or more of the regulatory sequences at the immunoglobulin locus, and comprises a coding sequence operably linked to one or more of the remaining regulatory sequences, such that the exogenous protein is regulated similarly to the endogenous immunoglobulin prior to integration of the exogenous protein. In some such embodiments, the nucleic acid may comprise a coding sequence that is in frame with a remaining coding sequence at the immunoglobulin locus, such that the exogenous protein is expressed as a fusion protein further including a portion of the endogenous immunoglobulin protein. In some embodiments, methods of targeting a nucleic acid to an endogenous immunoglobulin locus are known in the art, e.g. U.S. Pat. No. 5,204,244 and WO2013144566.

In some embodiments, the exogenous protein is an antibody comprising a first polypeptide comprising a heavy chain sequence and a second polypeptide comprising a light chain sequence and the one or more coding sequences comprises a first coding sequence encoding the first polypeptide and a second coding sequence encoding the second polypeptide. In some embodiments, the first coding sequence is integrated into or replaces all or a portion of an endogenous immunoglobulin heavy chain locus and/or the second coding sequence is integrated into or replaces all or a portion of an endogenous immunoglobulin light chain locus, such that the engineered B cell is capable of expressing the first and second polypeptides. In some embodiments, the first coding sequence is operably linked to a promoter and/or enhancer associated with the endogenous immunoglobulin heavy chain locus and/or the second coding sequence is operably linked to a promoter and/or enhancer associated with the endogenous immunoglobulin light chain locus. In some other embodiments, the first and second coding sequences are linked by a nucleotide linker sequence, such that the engineered B cell is capable of expressing the first and second polypeptides. In some embodiments, the first and second coding sequences are integrated into or replace all or a portion of an endogenous immunoglobulin heavy chain or light chain locus. In some embodiments, the linker sequence is or comprises an internal ribosome entry site (IRES), or encodes a self-cleaving peptide or a peptide that causes ribosome skipping including, without limitation, P2A, T2A, E2A, and F2A.

In some embodiments, the exogenous protein is a single chain antibody fragment comprising a heavy chain sequence and a light chain sequence, and the one or more coding sequences comprises a coding sequence encoding the single chain antibody fragment. In some embodiments, the coding sequence is integrated into or replace all or a portion of an endogenous immunoglobulin heavy chain or light chain locus, such that the engineered B cell is capable of expressing the single chain antibody fragment. In some embodiments, the single chain antibody fragment is an scFv.

Additional nucleic acids for introduction include those comprising (1) genes to improve the efficacy of therapy, such as by promoting viability and/or function of the transferred engineered B cells; (2) genes to provide a genetic marker for selection and/or evaluation of the cells, such as to assess in vivo survival or localization; and/or (3) genes to improve safety, for example, by making the engineered B cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

C. Receptor

The engineered B cell includes a receptor comprising a ligand binding domain, wherein, upon ligand binding, the receptor is capable of inducing (i) a mitogenic or proliferative signal; and/or (ii) a signal that is capable of modulating the differentiation of the engineered B cell (hereinafter also called "driving receptor"). In some embodiments, the receptors (driving receptors) include an extracellular antigen (or ligand) binding domain linked to a transmembrane domain. In some embodiments, the receptors also include one or more intracellular signaling components linked to the transmembrane domain, in some aspects via linkers. Such molecules may mimic or approximate a signal through a natural B cell receptor.

In some embodiments, the receptor (driving receptor) is a membrane-anchored form of an antibody (e.g., immunoglobulin component of a B cell receptor), and signals via an associated CD79 molecule. In some embodiments, the receptor is an endogenous B cell receptor. In some embodiments, the endogenous B cell receptor is specific for a ligand present in a vaccine. In some embodiments, the vaccine is selected from among a diphtheria, tetanus, and/or pertussis vaccine, an influenza vaccine, a measles, mumps, rubella, and/or varicella vaccine, a hepatitis vaccine, a polio vaccine, a rabies vaccine, a shingles vaccine, a smallpox vaccine, a typhoid vaccine, and a yellow fever vaccine.

In some embodiments, the receptor (driving receptor) is a recombinant receptor (such as a chimeric receptor) constructed with a specificity for a particular antigen (or marker or ligand), such as an antigen expressed in a particular tissue or cell type in which activity of the engineered B cell is desired, such as a cell type associated with a disease or condition to be targeted by the exogenous protein, e.g., a cancer marker or pathogen antigen, or an antigen that is more widely expressed either systemically or in a specific tissue or location, e.g. an environmental ligand as described. In some embodiments, the receptor includes in its extracellular portion one or more antigen binding molecules that specifically binds the antigen or ligand, such as one or more antigen-binding fragment, domain, or portion, or one or more antibody variable domains, and/or antibody molecules. In some embodiments, the receptor includes an antigen-binding portion or portions of an antibody molecule, such as a single-chain antibody fragment (scFv) derived from the variable heavy (VH) and variable light (VL) chains of a monoclonal antibody (mAb).

In some embodiments, the receptor (driving receptor) comprises an antibody heavy chain domain that specifically binds the antigen or ligand, such as the cell surface antigen of a cell or disease to be targeted, such as a pathogen-infected cell, a tumor cell, or a cancer cell, such as any of the antigens described herein or known in the art.

In some aspects, the antigen-specific binding, or recognition component is linked to a transmembrane domain, and optionally to one or more intracellular signaling domains. In some embodiments, the receptor includes a transmembrane domain fused to the extracellular domain of the receptor. In one embodiment, the transmembrane domain that naturally is associated with one of the domains in the receptor is used. In some instances, the transmembrane domain is selected or modified by amino acid substitution to avoid binding of such domains to the transmembrane domains of the same or different surface membrane proteins to minimize interactions with other members of the receptor complex.

In some embodiments, the receptor (driving receptor) includes at least one intracellular signaling component or components. In some embodiments, the receptor includes an intracellular component of the BCR complex, such as a CD79A or CD79B chain that mediates B-cell activation. Thus, in some aspects, the antigen binding molecule is linked to one or more cell signaling modules. In some embodiments, cell signaling modules include ITAM-containing intracellular signaling domains such as those derived from CD79A, CD79B, CD3ζ; FcRγ, FcRβ, CD3γ, CD3δ, CD3ε, CD5, CD22, CD79a, CD79b, or CD66d. In some embodiments, the receptor further includes a portion of one or more additional molecules such as Fc receptor γ, CD8, CD4, CD25, or CD16.

In some embodiments, upon ligation of the receptor (driving receptor), the cytoplasmic domain or intracellular signaling domain of the receptor activates at least one of the normal effector functions or responses of the engineered B cell. For example, in some contexts, the receptor induces a function of a B cell such as immunoglobulin class switching, switching from a membrane-anchored immunoglobulin form to a secreted immunoglobulin form, and/or differentiation of the engineered B cell. In some embodiments, signaling by the receptor induces production and/or secretion of the exogenous protein. In some embodiments, the intracellular signaling domain or domains include the cytoplasmic sequences of the B cell receptor (BCR), and in some aspects also those of co-receptors that in the natural context act in concert with such receptor to initiate signal transduction following receptor engagement, and/or any derivative or variant of such molecules, and/or any synthetic sequence that has the same functional capability.

1. Ligands or Antigens

In some embodiments, the engineered or endogenous receptors are capable of binding to ligands, such as antigens, via the ligand-binding domain, which can be the antigen-binding domain. In some of the embodiments, the receptor provided contains a ligand-binding domain that binds, such as specifically binds, the ligand. In some embodiments, the ligand-binding domain is or comprises a ligand-binding portion, such as all or a portion of an extracellular domain (ECD), of a receptor. In some embodiments, the ligand-binding domain is or includes an antibody or an antigen-binding fragment thereof, such as an scFv.

In some aspects, the ligand is expressed on the surface of cells, is associated with the membrane or surface of cells, is soluble and/or is a part of or associated with the extracellular matrix (ECM). In some embodiments, the ligand is associated with the membrane or surface of a cell. For example, the ligand is a transmembrane protein, such as a transmembrane receptor. In some examples, the ligand is associated with the membrane via interaction with a transmembrane protein. In some embodiments, the ligand is a cell surface protein expressed on the surface of an immune cell, such as a T cell or B cell. In some embodiments, the ligand is a cell surface receptor.

In some aspects, the ligand can be a polypeptide, a protein, an amino acid, a glycoprotein, a proteoglycan, a glycosaminoglycan, a lipid, a nucleic acid, a nucleotide, a nucleoside, a sugar, a polysaccharide, a small molecule, a metabolite, a lipoprotein, a steroid, an ion and/or combinations thereof. In some embodiments, the antigen is a polypeptide. In some embodiments, it is a carbohydrate or other molecule.

In some embodiments, the ligand, such as antigen, is selectively expressed or overexpressed on cells of the disease or condition, e.g., the tumor or pathogenic cells, as compared to normal or non-targeted cells or tissues. Thus, among the ligands and/or antigens targeted by the receptors are those expressed in the context of a disease, condition, or cell type to be targeted by the exogenous protein, e.g. therapeutic protein. In some embodiments, binding of the engineered B cells to such antigens via the described receptors, e.g. recombinant receptors or chimeric receptors containing or associated with one or more ITAM B cell signaling domains, such as signaling domains from CD79a or CD79b, stimulates signaling by the receptor to induce production and/or secretion of the exogenous protein in the proximity of cells associated with the disease. Among the diseases and conditions are proliferative, neoplastic, and malignant diseases and disorders, including cancers and tumors, including hematologic cancers. Also included are infectious diseases, autoimmune diseases, and any other disease or condition amenable to treatment with a therapeutic protein.

In some embodiments, antigens targeted by the receptors in some embodiments include cancer- or tumor-associated antigens. In some embodiments, the antigen is selected from among antigens associated with hematological cancers including, without limitation, leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, plasmacytoma, Waldenstrom's macroglobulinemia, heavy chain disease, myelodysplastic syndrome, hairy cell leukemia and myelodysplasia.

In some embodiments, the antigen is selected from among antigens associated with solid tumors including, without limitation, sarcomas and carcinomas, including adrenocortical carcinoma, cholangiocarcinoma, fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, stomach cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, thyroid cancer (e.g., medullary thyroid carcinoma and papillary thyroid carcinoma), pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer (e.g., cervical carcinoma and pre-invasive cervical dysplasia), colorectal cancer, cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, esophageal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, kidney cancer, melanoma, cancer of the uterus (e.g., endometrial carcinoma), urothelial cancers (e.g., squamous cell carcinoma, transitional cell carcinoma, adenocarcinoma, ureter cancer, and urinary bladder cancer), and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, the antigen is selected from among carbonic anhydrase IX, alpha-fetoprotein, alpha-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1alpha, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-gamma, IFN-alpha, IFN-beta, IL-2, IL-4R, IL-6R, IL-13R, IL-15R, IL-17R, IL-18R, IL-6, IL-8, IL-12, IL-15, IL-7, IL-18, IL-25, insulin-like growth factor-1 (IGF-1), KC4-antigen, KS-1-antigen, KS 1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, PIGF, ILGF, ILGF-1R, IL-6, IL-25, RSS, RANTES, T101, SAGE, S100, survivin, survivin-2B, TAC, TAG-72, tenascin, TRAIL receptors, TNF-alpha, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product, including peptide/MHC complexes derived therefrom (see, e.g., Sensi et al., Clin Cancer Res 2006, 12:5023-32; Parmiani et al., J Immunol 2007, 178: 1975-79; Novellino et al. Cancer Immunol Immunother 2005, 54:187-207).

Antigens targeted by the receptors in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the receptor binds a pathogen-associated (such as virally-encoded) antigen, including, without limitation, antigens derived from *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, Astroviridae, *Babesia* genus, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia* genus, *Borrelia* spp, *Brucella* genus, *Brugia malayi*, Bunyaviridae family, *Burkholderia cepacia* and other *Burkholderia* species, *Burkholderia mallei*, *Burkholderia pseudomallei*, Caliciviridae family, *Campylobacter* genus, *Candida albicans*, *Candida* spp, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium* spp, *Clostridium tetani*, *Coccidioides* spp, coronaviruses, *Corynebacterium diphtheriae*, *Coxiella burnetii*, Crimean-Congo hemorrhagic fever virus, *Cryptococcus neoformans*, *Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis*, *Ehrlichia ewingii*, *Ehrlichia* genus, *Entamoeba histolytica*, *Enterococcus* genus, *Enterovirus* genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FPI prion, Filarioidea superfamily, Flaviviruses, *Francisella tularensis*, *Fusobacterium* genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Human T cell leukemia virus 1 (HTLV-1), Japanese encephalitis virus, JC virus, Junin virus, Kaposi's Sarcoma associated herpesvirus (KSHV), *Kingella kingae*, *Klebsiella granulomatis*, Kuru prion, Lassa virus, *Legionella pneumophila*, *Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, Molluscum contagiosum virus (MCV), Mumps virus, *Mycobacterium leprae* and *Mycobacterium lepromatosis*, *Mycobacterium tuberculosis*, *Mycobacterium ulcerans*, *Mycoplasma pneumoniae*, *Naegleria fowleri*, *Necator americanus*, *Neisseria gonorrhoeae*, *Neisseria meningitidis*, *Nocardia asteroides*, *Nocardia* spp, *Onchocerca volvulus*, *Orientia tsutsugamushi*, Orthomyxoviridae family (Influenza), Paracoccidioides *brasiliensis*, *Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari*, *Rickettsia* genus, *Rickettsia prowazekii*, *Rickettsia rickettsii*, *Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii*, *Staphylococcus* genus, *Staphylococcus* genus, *Streptococcus agalactiae*, *Streptococcus pneumoniae*, *Streptococcus pyogenes*, *Strongyloides stercoralis*, *Taenia* genus, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton* spp, *Trichuris trichiura*, *Trypanosoma brucei*, *Trypanosoma cruzi*, *Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica*, *Yersinia pestis*, or *Yersinia pseudotuberculosis*.

In some embodiments, the ligand, such as antigen, is an environmental ligand that is more widely expressed or not selectively expressed or overexpressed on cells of a disease or condition. In some aspects, the environmental ligands are ligands not overexpressed on a disease cell, ligands that exhibit widespread tissue or cell expression, ligands that are ubiquitously expressed, ligands that are systemically expressed, or ligands that are not tissue specific. In some embodiments, binding of the engineered B cells to such ligands, such as antigens, via the described receptors, e.g. recombinant receptors or chimeric receptors containing or associated with one or more ITAM B cell signaling domains, such as signaling domains from CD79a or CD79b, stimulates signaling by the receptor to induce more widespread, such as systemic, production and/or secretion of the exogenous protein.

Among the ligands, such as environmental ligands, include those that are not overexpressed, or show relatively low expression, in the context of a disease, condition, or cell type to be targeted via the exogenous protein. In some embodiments, the expression of the ligand is higher on normal cells compared to diseased cells. Among the diseases and conditions are proliferative, neoplastic, and malignant diseases and disorders, including cancers and tumors, including hematologic cancers, cancers of the immune system, such as a lymphoma, a leukemia, and/or a myeloma, such as B, T, and myeloid leukemia and a multiple myeloma. In some examples, the disease or disorder is a solid tumor, such as a sarcoma, a carcinoma or a lymphoma. In other examples, the disease or disorder is an infection, such as a bacterial, viral, parasitic or fungal infection.

In some embodiments, the ligand includes ligands of homing receptors, ligands of adhesion receptors or ligands of chemokine receptors, e.g., homing or trafficking molecules, adhesion molecules or chemokines. In some embodiments, the ligand is a homing molecule or adhesion molecule. In some examples, the ligand is an Ig superfamily cell adhesion molecule (CAM), a cadherin, a selectin, an integrin, a homing or adhesion receptor. Cell adhesion molecules are typically expressed on the cell surface, and are involved in adhesion with other cells or with the extracellular matrix (ECM). Immune cells, such as leukocytes, including T cells, are recruited to different sites of the body, via the interaction between adhesion molecules present in sites such as the vascular endothelial cells and the homing or adhesion receptors expressed on the immune cells, such as an integrin.

In some embodiments, the ligand is a homing molecule or adhesion molecule that is a ligand to a homing or adhesion receptor expressed on an immune cell. In some embodiments, the ligand is a selectin, a vascular addressin, an intracellular adhesion molecule (ICAM) or a cadherin. Adhesion receptors expressed on immune cells can recognize and bind endothelial cell-expressed ligands, such as ICAM-1, 2 and 3 and VCAM-1/mucosal addressin cell adhesion molecule-1 (MAdCAM-1). In some embodiments, the ligand is selected from among E-selectin, P-selectin, PNAd, MAdCAM-1, ICAM-1, VCAM-1, E-cadherin, collagen type I, collagen type IV and laminin 1 In some embodiments, the ligand is N-CAM (Myelin protein zero), PE-CAM, L1-CAM, Nectin (PVRL1, PVRL2, PVRL3), CDH1, CDH2, CDH3, Desmoglein (DSG1, DSG2, DSG3, DSG4), Desmocollin (DSC1, DSC2, DSC3), Protocadherin PCDH1, PCDH15, T-cadherin, CDH4, CDH5, CDH6, CDH8, CDH11, CDH12, CDH15, CDH16, CDH17, CDH9, CDH10, L-selectin, Integrins, LFA-1 (CD11a+CD18), Integrin alphaXbeta2 (CD11c+CD18), Macrophage-1 antigen (CD11b+CD18), VLA-4 (CD49d+CD29), Glycoprotein (ITGA2B+ITGB3), CD44, Carcinoembryonic antigen, CD22, CD24, CD44, CD146 or CD164.

In some aspects, the ligand is a chemokine, or a ligand of a chemokine receptor. For example, the ligand is a ligand of a chemokine receptor selected from among CCR7, CCR5, CCR10 and CCR9, or is a chemokine selected from among CCL19, CCL21, CCL3, CCL4, CCL5, CCL8, CCL11, CCL13, CCL14, CCL16, CCL27, CCL28, and CCL25.

In some embodiments, the ligand is expressed on the surface of or is associated with the endothelium or endothelial cells. For example, the ligand is selected from ACE/CD143, C1q R1/CD93, VE-Cadherin, CC Chemokine Receptor D6, CD31/PECAM-1, CD34, CD36/SR-B3, CD151, CD160, CD300LG/Nepmucin, CL-K1/COLEC11, CL-P1/COLEC12, Coagulation Factor III/Tissue Factor, DC-SIGNR/CD299, DCBLD2/ESDN, ECSCR, EMMPRIN/CD147, Endoglin/CD105, Endomucin, Endosialin/CD248, EPCR, Erythropoietin R, ESAM, FABPS/E-FABP, FABP6, ICAM-1/CD54, ICAM-2/CD102, IL-1 RI, IL-13 R alpha 1, Integrin alpha 4/CD49d, Integrin alpha 4 beta 1, Integrin alpha 4 beta 7/LPAM-1, Integrin beta 2/CD18, KLF4, LYVE-1, MCAM/CD146, Nectin-2/CD112, PD-ECGF/Thymidine Phosphorylase, Podocalyxin, Podoplanin, S1P1/EDG-1, S1P2/EDG-5, S1P3/EDG-3, S1P4/EDG-6, S1P5/EDG-8, E-Selectin/CD62E, E-Selectin (CD62E)/P-Selectin (CD62P), P-Selectin/CD62P, SLAM/CD150, Stabilin-1, Stabilin-2, TEM7/PLXDC1, TEM8/ANTXR1, Thrombomodulin/BDCA-3, THSD1, Tie-2, TNF RI/TNI-RSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, VGSQ and vWF-A2.

In some aspects, the ligand is a component of or associated with the extracellular matrix (ECM). For example, the ligand is a proteoglycan, a glycosaminoglycan, a polysaccharide, a protein or a combination thereof present in the ECM. In some aspects, the ligand is a proteoglycan or a glycosaminoglycan, such as heparin, heparan sulfate, chondroitin sulfate and/or keratan sulfate. In other aspects, the ligand is a polysaccharide, such as a hyaluronan. In other aspects, the ligand is a protein, such as a collagen, an elastin, a laminin, a fibronectin, a vitronectin, a tenascin, a thrombospondin, a fibrillin, a fibulin, a latent TGF-β binding protein (LTBP), a matrix metalloproteinase, a heparanase, or a disintegrin and metalloproteinase with thrombospondin motifs (ADAMTS) family protein.

In some examples, the ligand is a lipid molecule or a lipoprotein, or a combination or a complex thereof, such as plasma lipoprotein particles. For example, the ligand is a cell membrane lipid, such as phosphatidylcholine (PC), sphingomyelin (SM), phosphatidylethanolamine (PE), phosphoinositol (PI) or phosphatidylserine (PS). In some examples, the ligand is a plasma lipoprotein particle or portion thereof, which can include apolipoproteins such as ApoA, ApoB, ApoC, ApoE, triacylglycerol, cholesterol and phospholipids.

In some embodiments, the ligand is expressed systemically, such as in the systemic circulation. In some embodiments, the ligand is expressed on cells present in the circulation or blood cells, e.g., leukocytes or erythrocytes. For example, the ligand is expressed on red blood cells, such as ABO blood group antigen, Rh factor, Aquaporin 1, Glut1, Kidd antigen protein, RhAG, $Na^+/K^+$ ATPase, $Ca^{2+}$ ATPase, $Na^+$ $K^+$ cotransporter, $Na^+$-$Cl^-$ cotransporter, Na—H exchanger, K—Cl cotransporter, Gardos Channel, ICAM-4, BCAM, RhAG, Protein 4.1R, Glycophorin C and D, XK, RhD/RhCE, Duffy protein, Adducin, Dematin, hemoglobin or heme.

In some aspects, the ligand is a soluble ligand, such as a soluble molecule present in the blood or circulation. In some aspects, the soluble ligand can be temporarily associated with a cell membrane or a cell surface molecule or the ECM. In some embodiments, the soluble ligand is a signaling molecule, a metabolite, a small molecule, a chemokine, a cytokine, a growth factor, a hormone, a soluble receptor, an antibody, a drug, an ion, a nucleic acid, an amino acid, a lipid, a steroid, or a sugar, or fragments or combinations thereof.

In some aspects, the ligand is endogenous to the subject. In other aspects, the ligand is exogenous to the subject, such that receptor signaling is induced upon administration of the ligand to the subject. In some embodiments, the ligand is a drug or a small molecule, and is administered to the subject. In some aspects, the exogenously administered ligand is a synthetic ligand or a natural ligand.

In some aspects, the ligand is a soluble proteinaceous ligand, such as soluble FAS ligand or soluble NKG2D ligand. In some embodiments, the ligand is an antibody or a portion thereof. In some examples, the soluble ligand is cleaved from a membrane-bound molecule. In some examples, the ligand is a hormone, a growth factor or a cytokine, such as Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Foetal bovine somatotrophin (FBS), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Keratinocyte growth factor (KGF), Migration-stimulating factor (MSF), Myostatin (GDF-8), Nerve growth factor (NGF) and other neurotrophins, Platelet-derived growth factor (PDGF), Thrombopoietin (TPO), T-cell growth factor (TCGF), Transforming growth factor alpha (TGF-α), TGF-β, Tumor necrosis factor-alpha (TNF-α), Vascular endothelial growth factor (VEGF), Wnt signaling pathway molecules, Placental growth factor (PGF), Interleukin (IL)-1, IL-2, IL-3, IL-4, IL-5, IL-6, IL-7 or Renalase.

In some aspects, the ligand is a small molecule or a metabolite, e.g., adenosine. In some aspects, the ligand is a soluble metabolite, such as adenosine, adenosine triphosphate, adenosine diphosphate or adenosine monophosphate, lactate, nitric oxide or bicarbonate.

In some embodiments, the ligand is an immunomodulatory protein, such as a protein that is expressed on immune cells. In some embodiments, the ligand, such as immunomodulatory protein can sometimes be found in or expressed in the tumor microenvironment. In some aspects, the ligand is a signaling molecule, a receptor, or an immune checkpoint molecule or an antigen.

For example, in some embodiments, the ligand is an immune checkpoint molecule. In some embodiments, the immune checkpoint molecule immune checkpoint molecule is expressed on an antigen presenting cell. In some embodiments, the ligand is CD27, OX40, GITR, CD137, CD28, ICOS, A2AR, CD276, VTCN1, B7-H7, BTLA, CTLA-4, CD152, IDO, TDO, KIR, LAG3, PD-1, TIM-3, VISTA, M-CSF, PDL1, PDL2, CD80, CD86, B7RP1, B7-H3, B7-H4, HVEM, CD137L, OX40L, CD70, CD40, GAL9 or adenosine. In some embodiments, binding of the provided ligand binding domain to the ligand that is an immune checkpoint molecule, such as CTLA-4, PD-1, PDL1 or PDL2, antagonizes the function of the immune checkpoint present on antigen-presenting cells (APCs), thereby enhancing or boosting the immune response. In some embodiments, the ligand is a metabolic immune checkpoint molecule, e.g., adenosine.

In some embodiments, binding of the ligand binding domain can stimulate or enhance a signal through a ligand that is a receptor. In some cases, binding of the ligand binding domain of a provided driving receptor to the ligand reduces or decreases the interaction of the ligand for its inhibitory receptor. Thus, in some cases, the interaction between the ligand and the ligand-binding domain of the driving receptor can induce both signal cell signaling to induce a mitogenic or proliferative signal in the B cell to which the receptor is engineered and act as a checkpoint to block the normal inhibitory signaling pathways to which the ligand may otherwise normally promote.

In some examples, the ligand is a cell surface receptor and binding of the provided ligand binding domain to the driving receptor antagonizes or interferes with the activating or inhibitory signal through the activating or inhibitory receptor. In some embodiments, binding of the ligand binding domain of the provided driving receptor to a ligand that is a receptor, e.g. CTLA-4, can interfere with CTLA-4 signaling, and thereby reverse immunosuppression mediated by CTLA-4. In some examples, binding of the ligand binding domain to a ligand that is the NK cell inhibitory receptor CD94 and/or NKG2A, can interfere with signaling through the CD94/NKG2A heterodimer, thereby reversing suppression of NK cell function.

In some embodiments, the ligand is a receptor expressed on an NK cell, such as an NK cell inhibitory receptor, such as CD94, NKG2A and/or killer cell immunoglobulin-like receptors (KIRs). In other examples, the ligand is an activating or costimulatory receptor on NK cells, e.g., TRAIL, CD16, NKp30a, NPp30b, NKG2C, NKG2D, 4Ba, DNAM-1, CD137, OX40 or CD27.

In some aspects, the ligand is exogenous to the subject. In some examples, the ligand is administered to the subject.

In some embodiments, the ligand-binding domain is or includes a ligand-binding portion of a receptor, such as a cytokine receptor, a signaling molecule receptor, a small molecule receptor, a hormone receptor, a homing or adhesion molecule receptor or a T-cell receptor. In some embodiments, the receptor is a monomeric receptor. In some embodiments, the receptor is dimeric and the receptor dimerizes upon binding of the ligand. In some embodiments, the ligand binding domain is a ligand binding portion or an extracellular portion of a receptor. For example, the ligand binding domain is the extracellular portion of a chemokine receptor, such as CCR7, CCR5, CCR10 and CCR9.

In some examples, the ligand-binding domain is an antibody or an antigen-binding portion or fragment thereof that specifically binds the ligand. In some embodiments, the ligand-binding domain is or includes an antigen-binding portion or portions of an antibody molecule, such as a single-chain antibody fragment (scFv) derived from the variable heavy ($V_H$) and variable light ($V_L$) chains of a monoclonal antibody (mAb).

In some embodiments, the receptor contains an antibody or an antigen-binding fragment (e.g. scFv) that specifically recognizes a ligand, e.g., an antigen, such as an intact antigen expressed on the surface of a cell, or a soluble ligand, e.g., an antigen, such as any as described above.

2. Linker, Transmembrane Domain and Spacer

In some embodiments, the provided driving receptors, such as recombinant receptors provided herein, e.g., chimeric receptors, includes a transmembrane domain. In some embodiments, the transmembrane domain links an extracellular domain, e.g., ligand binding domain, to an intracellular signaling domain, e.g., an intracellular ITAM signaling domain. The ligand binding domain, transmembrane domain, and/or intracellular signaling domain can be linked directly or indirectly. In some embodiments, the extracellular domain and transmembrane domain are linked by a spacer, such as any described herein.

In some embodiments, the ligand binding domain is linked to the intracellular signaling domain via one or more transmembrane domain. In some embodiments, the transmembrane domain is fused to the extracellular domain. In some aspects, a transmembrane domain that naturally is associated with a ligand binding domain derived from a receptor or a portion thereof, is used. In some instances, the transmembrane domain is selected or modified by amino acid substitution to avoid binding of such domains to the transmembrane domains of the same or different surface membrane proteins to minimize interactions with other members of the receptor complex.

In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the intracellular signaling domain of the receptor.

The transmembrane domain in some embodiments is derived either from a natural or from a synthetic source. Where the source is natural, the domain in some aspects is derived from any membrane-bound or transmembrane protein, such as a cell surface receptor that includes a transmembrane domain, e.g., an integrin receptor, a cytokine receptor or a chemokine receptor. In some embodiments, the transmembrane domain in some embodiments is synthetic. In some embodiments, the synthetic transmembrane domain comprises predominantly hydrophobic residues such as leucine and valine. In some embodiments, a triplet of phenylalanine, tryptophan and valine will be found at each end of a synthetic transmembrane domain. In some embodiments, the linkage is by linkers, spacers, and/or transmembrane domain(s).

In some embodiments, the transmembrane domain include those derived from (i.e., comprise at least the transmembrane region(s) of) molecules expressed on the surface of immune cells, such as B cells, including a B cell receptor, or the transmembrane region of a molecule, including, CD19, CD20, CD21, CD22, CD27, CD23, CD24, CD38, CD40, CD138, CD269, CXCR4, CXCR5 or CXCR7. In some embodiments, the transmembrane region(s) of molecules expressed on cell include molecules expressed on the surface of T cell or other immune cell, including the α, β, δ, or γ chain of the T-cell receptor, CD28, CD3E, CD3, CD45, CD4, CD5, CD8, CD8 alpha, CD9, CD16, CD22, CD33, CD37, CD40, CD64, CD80, CD86, CD134, CD137, CD154, RANK, interleukin-1 receptor type 1 (IL1R-1), interleukin-1 receptor type 1 accessory protein (IL1R-1AcP), and/or transmembrane regions containing functional variants thereof such as those retaining a substantial portion of the structural, e.g., transmembrane, properties thereof.

In some embodiments, the recombinant receptor, e.g., chimeric receptor, further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the portion of the constant region serves as a spacer region between the ligand-binding domain, such as the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to $C_H2$ and $C_H3$ domains, or IgG4 hinge linked to the $C_H3$ domain. Exemplary spacers include, but are not limited to, those described in Hudecek et al. (2013) *Clin. Cancer Res.,* 19:3153, International PCT Pub. No. WO2014/031687, U.S. Pat. No. 8,822,647 or U.S. Application Pub. No. US2014/0271635.

In some embodiments, the constant region or portion thereof is of a human IgG, such as IgG4 or IgG1. In some embodiments, the spacer has the sequence ESKYGPPCPPCP (set forth in SEQ ID NO: 6). In some embodiments, the spacer has the sequence set forth in SEQ ID NO: 7. In some embodiments, the spacer has the sequence set forth in SEQ ID NO: 8. In some embodiments, the constant region or portion is of IgD. In some embodiments, the spacer has the sequence set forth in SEQ ID NO: 9. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any one of SEQ ID NOs: 6-9

In some embodiments, the spacer contains only a hinge region of an IgG, such as only a hinge of IgG4 or IgG1, such as the hinge only spacer set forth in SEQ ID NO: 6. In other embodiments, the spacer is or comprises an Ig hinge, e.g., an IgG4-derived hinge, optionally linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO: 8. In some embodiments, the spacer is an Ig hinge, e.g., an IgG4 hinge, linked to a $C_H3$ domain only, such as set forth in SEQ ID NO: 7. In some embodiments, the spacer is or comprises a glycine-serine rich sequence or other flexible linker such as known flexible linkers.

Any of the linkages of domains of the driving receptors provided can be direct or indirect, e.g., linked by a linker and/or spacer. Any of the domains can be present in plurality, in tandem or separated by other domains, linkers or spacers.

D. Additional Modifications

In some embodiments, the engineered B cells described herein comprise one or more additional modifications. In some embodiments, the modification affects the expression, activity, and/or function of an endogenous immunoglobulin. In some embodiments, the modification affects the capacity for the engineered B cell to produce and/or secrete the exogenous protein. In some embodiments, the modification affects the lineage determination of the engineered B cell. In some embodiments, any of the modifications can be carried out using a gene modification strategy, such as any described in Section VI.

1. Endogenous Immunoglobulin

In some embodiments, the engineered B cells described herein comprise one or more modifications that affect the expression of an endogenous immunoglobulin heavy and/or light chain. In some embodiments, the expression of the endogenous immunoglobulin heavy and/or light chain is reduced. In some embodiments, the expression of the endogenous immunoglobulin heavy and/or light chain is reduced by at least about 50% (such as by at least about any of 55%, 60%, 65%, 70%, 75%, 80%, 85%, 90%, 95%, or more, including any ranges between these values) as compared to the expression in the engineered B cell in the absence of the modification. In some embodiments, the expression of the endogenous immunoglobulin heavy and/or light chain is eliminated.

In some embodiments, the modification comprises introduction of an agent that affects the expression of the endogenous immunoglobulin heavy and/or light chain into the engineered B cell. In some embodiments, the agent is an inhibitory nucleic acid molecule. In some embodiments, an inhibitory nucleic acid, such as siRNA or shRNA, is used to repress endogenous immunoglobulin heavy and/or light chain expression. Methods of using inhibitory agents, including inhibitory nucleic acids, including using RNA interference technology, such as siRNA or shRNA, to repress cell expression of the endogenous immunoglobulin heavy and/or light chain are well within the level of a skilled artisan, and are described in detail below. Commercially available reagents, such as siRNA or shRNA reagents, are readily available, see e.g. from GeneCopoeia (see e.g. catalog number HSH054299).

In some embodiments, the modification comprises gene editing to introduce a genetic disruption that affects the expression of the endogenous immunoglobulin heavy and/or light chain. In some embodiments, the genetic disruption comprises a disruption in the gene encoding the endogenous immunoglobulin heavy and/or light chain. In some embodiments, the genetic disruption is biallelic. In some embodiments, knockdown in carried out using methods using CRISPR systems for knockout of an endogenous immunoglobulin heavy and/or light chain gene are known in the art. Commercially available kits, gRNA vectors and donor vectors, for knockout of an endogenous immunoglobulin heavy and/or light chain gene, via CRISPR also are readily available. For example, commercially available reagents for knockout of an endogenous immunoglobulin heavy and/or light chain gene are available, for example, for knockout of an immunoglobulin heavy constant gamma 1 (IGHG1) are available, such as from GeneCopoeia (see e.g. catalog number HTN254299).

2. Production and/or Secretion of the Exogenous Protein

In some embodiments, the engineered B cells described herein comprise one or more modifications that affect the capacity for the engineered B cell to produce and/or secrete the exogenous protein. In some embodiments, the modification affects the lineage determination of the engineered B cell. In some embodiments, the modification affects the expression of one or more genes involved in determining the cell type of the engineered B cell (e.g., naïve mature B cell, plasmablast, plasma cell, or memory B cell).

In some embodiments, the one or more genes involved in determining the cell type of the engineered B cell is selected from among PAX5, BACH2, BCL-6, OBF1, OCT2, PU.1, SPIB, ETS1, IRF8, IRF4, BLIMP1, and XBP1. In some embodiments, the expression of some of the one or more genes is reduced as compared to the expression in the engineered B cell in the absence of the modification. In some embodiments, the expression of one or more genes selected from among PAX5, BACH2, BCL-6, OBF1, OCT2, PU.1, SPIB, ETS1, and IRF8 is reduced. In some embodiments, the expression is reduced by at least about 50% (such as by at least about any of 55%, 60%, 65%, 70%, 75%, 80%, 85%, 90%, 95%, or more, including any ranges between these values). In some embodiments, the expression of some of the one or more genes is eliminated.

In some embodiments, the expression of some of the one or more genes is increased as compared to the expression in the engineered B cell in the absence of the modification. In some embodiments, the expression of one or more genes selected from among IRF4, BLIMP1, and XBP1 is increased. In some embodiments, the expression is increased by at least about 50% (such as by at least about any of 50%, 60%, 70%, 80%, 90%, 100%, 200%, 300%, 400%, 500%, or more, including any ranges between these values).

In some embodiments, the engineered B cell comprises or further comprises a disruption of, or an agent that reduces expression of, a PAX5 gene. In some embodiments, an inhibitory nucleic acid, such as siRNA or shRNA, is used to repress PAX5 expression. Methods of using inhibitory agents, including inhibitory nucleic acids, including using RNA interference technology, such as siRNA or shRNA, to repress cell expression of PAX5 are well within the level of a skilled artisan, and are described in detail below. Commercially available reagents, such as siRNA or shRNA reagents, are readily available, see e.g. from GeneCopoeia (see e.g. catalog number HSH069449). In some embodiments, gene editing methods are used to repress or disrupt PAX5. Methods using CRISPR systems for knockout of a PAX5 gene are known in the art. For example, exemplary target sequences for guide RNA sequences can include any set forth in SEQ ID NOS: 10-15. Commercially available kits, gRNA vectors and donor vectors, for knockout of a PAX5 gene, via CRISPR also are readily available. For example, commercially available reagents for knockout of a PAX5 gene are available, for example, from GeneCopoeia (see e.g. catalog number HTN269449).

In some embodiments, the engineered B cell comprises or further comprises a disruption of, or an agent that reduces expression of, a BACH2 gene. In some embodiments, an inhibitory nucleic acid, such as siRNA or shRNA, is used to repress BACH2 expression. Methods of using inhibitory agents, including inhibitory nucleic acids, including using RNA interference technology, such as siRNA or shRNA, to repress cell expression of BACH2 are well within the level of a skilled artisan, and are described in detail below. Commercially available reagents, such as siRNA or shRNA reagents, are readily available, see e.g. from GeneCopoeia (see e.g. catalog number HSH065389). In some embodiments, gene editing methods are used to repress or disrupt BACH2. Methods using CRISPR systems for knockout of a BACH2 gene are known in the art. For example, exemplary target sequences for guide RNA sequences can include any set forth in SEQ ID NOS: 16-21. Commercially available kits, gRNA vectors and donor vectors, for knockout of a BACH2 gene, via CRISPR also are readily available. For example, commercially available reagents for knockout of a BACH2 gene are available, for example, from GeneCopoeia (see e.g. catalog number HTN265389).

In some embodiments, the engineered B cell comprises or further comprises a disruption of, or an agent that reduces expression of, a BCL-6 gene. In some embodiments, an inhibitory nucleic acid, such as siRNA or shRNA, is used to repress BCL-6 expression. Methods of using inhibitory agents, including inhibitory nucleic acids, including using RNA interference technology, such as siRNA or shRNA, to repress cell expression of BCL-6 are well within the level of a skilled artisan, and are described in detail below. Commercially available reagents, such as siRNA or shRNA reagents, are readily available, see e.g. from OriGene (see e.g. catalog number TL306420). In some embodiments, gene editing methods are used to repress or disrupt BCL-6. Methods using CRISPR systems for knockout of a BCL-6 gene are known in the art. For example, exemplary target sequences for guide RNA sequences can include any set forth in SEQ ID NOS: 22-27. Commercially available kits, gRNA vectors and donor vectors, for knockout of a BCL-6 gene, via CRISPR also are readily available. For example, commercially available reagents for knockout of a BCL-6 gene are available, for example, from OriGene (see e.g. catalog number KN219007G1).

In some embodiments, the engineered B cell comprises or further comprises a disruption of, or an agent that reduces expression of, an OBF1 gene. In some embodiments, an inhibitory nucleic acid, such as siRNA or shRNA, is used to repress OBF1 expression. Methods of using inhibitory agents, including inhibitory nucleic acids, including using RNA interference technology, such as siRNA or shRNA, to repress cell expression of OBF1 are well within the level of a skilled artisan, and are described in detail below. Commercially available reagents, such as siRNA or shRNA reagents, are readily available, see e.g. from GeneCopoeia (see e.g. catalog number HSH013528). In some embodiments, gene editing methods are used to repress or disrupt OBF1. Methods using CRISPR systems for knockout of an OBF1 gene are known in the art. For example, exemplary target sequences for guide RNA sequences can include any set forth in SEQ ID NOS: 28-33. Commercially available kits, gRNA vectors and donor vectors, for knockout of an OBF1 gene, via CRISPR also are readily available. For example, commercially available reagents for knockout of an OBF1 gene are available, for example, from GeneCopoeia (see e.g. catalog number HTN213528).

In some embodiments, the engineered B cell comprises or further comprises a disruption of, or an agent that reduces expression of, an OCT2 gene. In some embodiments, an inhibitory nucleic acid, such as siRNA or shRNA, is used to repress OCT2 expression. Methods of using inhibitory agents, including inhibitory nucleic acids, including using RNA interference technology, such as siRNA or shRNA, to repress cell expression of OCT2 are well within the level of a skilled artisan, and are described in detail below. Commercially available reagents, such as siRNA or shRNA reagents, are readily available, see e.g. from GeneCopoeia (see e.g. catalog number HSH055116). In some embodiments, gene editing methods are used to repress or disrupt OCT2. Methods using CRISPR systems for knockout of an OCT2 gene are known in the art. For example, exemplary target sequences for guide RNA sequences can include any set forth in SEQ ID NOS: 34-39. Commercially available kits, gRNA vectors and donor vectors, for knockout of an OCT2 gene, via CRISPR also are readily available. For example, commercially available reagents for knockout of an OCT2 gene are available, for example, from GeneCopoeia (see e.g. catalog number HTN255116).

In some embodiments, the engineered B cell comprises or further comprises a disruption of, or an agent that reduces expression of, a PU.1 gene. In some embodiments, an inhibitory nucleic acid, such as siRNA or shRNA, is used to repress PU.1 expression. Methods of using inhibitory agents, including inhibitory nucleic acids, including using RNA interference technology, such as siRNA or shRNA, to repress cell expression of PU.1 are well within the level of a skilled artisan, and are described in detail below. Commercially available reagents, such as siRNA or shRNA reagents, are readily available, see e.g. from OriGene (see e.g. catalog number TG316738). In some embodiments, gene editing methods are used to repress or disrupt PU.1. Methods using CRISPR systems for knockout of a PU.1 gene are known in the art. For example, exemplary target sequences for guide RNA sequences can include any set forth in SEQ ID NOS: 40-45. Commercially available kits, gRNA vectors and donor vectors, for knockout of a PU.1 gene, via CRISPR also are readily available. For example, commercially available reagents for knockout of a PU.1 gene are available, for example, from OriGene (see e.g. catalog number KN212818).

In some embodiments, the engineered B cell comprises or further comprises a disruption of, or an agent that reduces expression of, an SPIB gene. In some embodiments, an inhibitory nucleic acid, such as siRNA or shRNA, is used to repress SPIB expression. Methods of using inhibitory agents, including inhibitory nucleic acids, including using RNA interference technology, such as siRNA or shRNA, to repress cell expression of SPIB are well within the level of a skilled artisan, and are described in detail below. Commercially available reagents, such as siRNA or shRNA reagents, are readily available, see e.g. from GeneCopoeia (see e.g. catalog number HSH064328). In some embodiments, gene editing methods are used to repress or disrupt SPIB. Methods using CRISPR systems for knockout of an SPIB gene are known in the art. For example, exemplary target sequences for guide RNA sequences can include any set forth in SEQ ID NOS: 46-51. Commercially available kits, gRNA vectors and donor vectors, for knockout of an SPIB gene, via CRISPR also are readily available. For example, commercially available reagents for knockout of an SPIB gene are available, for example, from GeneCopoeia (see e.g. catalog number HTN264328).

In some embodiments, the engineered B cell comprises or further comprises a disruption of, or an agent that reduces expression of, an ETS1 gene. In some embodiments, an inhibitory nucleic acid, such as siRNA or shRNA, is used to repress ETS1 expression. Methods of using inhibitory agents, including inhibitory nucleic acids, including using RNA interference technology, such as siRNA or shRNA, to repress cell expression of ETS1 are well within the level of a skilled artisan, and are described in detail below. Commercially available reagents, such as siRNA or shRNA reagents, are readily available, see e.g. from GeneCopoeia (see e.g. catalog number HSH054427). In some embodiments, gene editing methods are used to repress or disrupt ETS1. Methods using CRISPR systems for knockout of an ETS1 gene are known in the art. For example, exemplary target sequences for guide RNA sequences can include any set forth in SEQ ID NOS: 52-57. Commercially available kits, gRNA vectors and donor vectors, for knockout of an ETS1 gene, via CRISPR also are readily available. For example, commercially available reagents for knockout of an ETS1 gene are available, for example, from GeneCopoeia (see e.g. catalog number HTN254427).

In some embodiments, the engineered B cell comprises or further comprises a disruption of, or an agent that reduces expression of, an IRF8 gene. In some embodiments, an inhibitory nucleic acid, such as siRNA or shRNA, is used to repress IRF8 expression. Methods of using inhibitory agents, including inhibitory nucleic acids, including using RNA interference technology, such as siRNA or shRNA, to repress cell expression of IRF8 are well within the level of a skilled artisan, and are described in detail below. Commercially available reagents, such as siRNA or shRNA reagents, are readily available, see e.g. from GeneCopoeia (see e.g. catalog number HSH009251). In some embodiments, gene editing methods are used to repress or disrupt IRF8. Methods using CRISPR systems for knockout of an IRF8 gene are known in the art. For example, exemplary target sequences for guide RNA sequences can include any set forth in SEQ ID NOS: 58-63. Commercially available kits, gRNA vectors and donor vectors, for knockout of an IRF8 gene, via CRISPR also are readily available. For example, commercially available reagents for knockout of an IRF8 gene are available, for example, from GeneCopoeia (see e.g. catalog number HTN209251).

In some embodiments, the engineered B cell comprises or further comprises an agent or genetic modification that increases expression of an IRF4 gene. In some embodiments, a nuclease inactive CRISPR/Cas system is used to activate IRF4 expression. Methods of using such systems to activate cell expression of IRF4 are well within the level of a skilled artisan, and are described in detail below. For example, exemplary guide RNA sequences can include any set forth in SEQ ID NOS: 64-66. Commercially available reagents, such as nuclease dead Cas9 (dCas9) and gRNA vectors, are readily available, see e.g. from Santa Cruz Biotechnology (see e.g. catalog number sc-400288-ACT). In some embodiments, gene editing methods are used to increase expression of IRF4. Methods using CRISPR systems for knock-in of an IRF4 gene are known in the art.

In some embodiments, the engineered B cell comprises or further comprises an agent or genetic modification that increases expression of a BLIMP1 gene. In some embodiments, a nuclease inactive CRISPR/Cas system is used to activate BLIMP1 expression. Methods of using such systems to activate cell expression of BLIMP1 are well within the level of a skilled artisan, and are described in detail below. For example, exemplary guide RNA sequences can include any set forth in SEQ ID NOS: 67-72. Commercially available reagents, such as nuclease dead Cas9 (dCas9) and gRNA vectors, are readily available, see e.g. from Santa Cruz Biotechnology (see e.g. catalog number sc-400585-ACT). In some embodiments, gene editing methods are used to increase expression of BLIMPE Methods using CRISPR systems for knock-in of a BLIMP1 gene are known in the art.

In some embodiments, the engineered B cell comprises or further comprises an agent or genetic modification that increases expression of an XBP1 gene. In some embodiments, a nuclease inactive CRISPR/Cas system is used to activate XBP1 expression. Methods of using such systems to activate cell expression of XBP1 are well within the level of a skilled artisan, and are described in detail below. For example, exemplary guide RNA sequences can include any set forth in SEQ ID NOS: 73-75. Commercially available reagents, such as nuclease dead Cas9 (dCas9) and gRNA vectors, are readily available, see e.g. from Santa Cruz Biotechnology (see e.g. catalog number sc-400131-ACT). In some embodiments, gene editing methods are used to increase expression of XBP1. Methods using CRISPR systems for knock-in of an XBP1 gene are known in the art.

In some embodiments of an engineered B cell described herein comprising one or more modifications that affect the capacity for the engineered B cell to produce and/or secrete the exogenous protein, the III. Methods of Engineering B Cells Also provided are methods for the preparation and culture of the engineered B cells provided herein.

1. Cell Source

The cells and compositions containing the cells for engineering typically are isolated from a sample, such as a biological sample, e.g., one obtained from or derived from a subject. In some embodiments, the subject from which the cell is isolated is one having a particular disease or condition or in need of a cell therapy or to which cell therapy will be administered. The subject in some embodiments is a mammal, such as a human, such as a subject in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, and serum, tonsils, and bone marrow, including processed samples derived therefrom. In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, and bone marrow, and/or cells derived therefrom. Samples include, in the context of cell therapy, e.g., adoptive cell therapy, samples from autologous and allogeneic sources.

In some embodiments, the cells are derived from cell lines, e.g., B cell lines. The cells in some embodiments are obtained from a xenogeneic source, for example, from mouse, rat, non-human primate, and pig.

Cell Processing, Preparation, and Non-Affinity-Based Neparation

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including B cells.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

Separation Based on Affinity and/or Marker Profile

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some aspects, the sample or composition of cells to be separated is incubated with small, magnetizable or magnetically responsive material, such as magnetically responsive particles or microparticles, such as paramagnetic beads (e.g., such as Dynabeads® or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood.1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined B cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

Cryopreservation

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

Incubation and Culture

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a genetically engineered exogenous protein and/or receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. For examples of B cell culture methods, see WO2014146074, WO2010034103, WO2012072814, and WO2007067046.

In some embodiments, the stimulating conditions or agents include one or more agent, e.g., ligand, which is capable of stimulating the cell. Such agents can include IL-2, IL-3, IL-6, IL-10, SCF, G-CSF, CpG, CD40 ligand, Flt3 ligand, or thrombopoietin. Optionally, the method may further comprise the step of adding heat-killed bacterial cells, such as PANSORBIN® (heat-killed, formalin-fixed Staphylococcus aureus cells that have a coat of protein A).

In some aspects, incubation is carried out in accordance with techniques such as those described in U.S. Pat. No. 8,133,727 and Luo, X. M. et al. (2009) *Blood* 113(7): 1422-1431.

In some embodiments, the stimulating conditions include temperature suitable for the growth of human B lymphocytes, for example, at least about 25 degrees Celsius, generally at least about 30 degrees, and generally at or about 37 degrees Celsius. Optionally, the incubation may further comprise adding feeder cells providing the B cell lineage growth factor IL-7 (e.g., S17 cells or murine stromal MS5 cells).

In some aspects, the methods include assessing expression of one or more markers on the surface of the engineered B cells or cells being engineered. In one embodiment, the methods include assessing surface expression of one or more surface markers of a particular B cell lineage, for example, by affinity-based detection methods such as by flow cytometry.

2. Engineering

In some embodiments, there are provided methods of producing the engineered B cells described herein. Various methods for the introduction of genetically engineered components, such as an exogenous protein and/or a recombinant receptor (driving receptor) are well known and may be used with the provided methods and compositions. Exemplary methods include those for transfer of nucleic acids encoding the exogenous proteins and/or recombinant receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell.

In some embodiments, there is provided a method of producing an engineered B cell, comprising introducing one or more nucleic acid molecules comprising one or more coding sequences encoding an exogenous protein described herein into an input B cell or B cell precursor.

In some embodiments, the input cell is a B cell. In some embodiments, the B cell is selected from among a naïve mature B cell, a plasmablast, a plasma cell, and a memory B cell. In some embodiments, the input cell is a B cell precursor. In some embodiments, the B cell precursor is a hematopoietic stem cell (HSC). In some embodiments, the B cell precursor is induced to differentiate into a B cell selected from among a naïve mature B cell, a plasmablast, a plasma cell, and a memory B cell.

In some embodiments, the input cell is a B cell precursor, and inducing the input cell to differentiate into a B cell comprises in vitro maturation of the input cell. Various techniques for in vitro maturation of HSCs into secreting B lymphocytes and plasma cells are known and can be used in the methods described herein. See for example Luo, X. M., et al. (2009). *Blood,* 113(7), 1422-1431.

In some embodiments, the method further comprises modifying the input cell to increases the capacity of the engineered B cell to produce and/or secrete the exogenous protein. In some embodiments, the modifying comprises altering the expression of one or more genes selected from among PAX5, BACH2, BCL-6, OBF1, OCT2, PU.1, SPIB, ETS1, IRF8, IRF4, BLIMP1, and XBP1. In some embodiments, the expression of one or more of PAX5, BACH2, BCL-6, OBF1, OCT2, PU.1, SPIB, ETS1, and IRF8 is reduced or eliminated. In some embodiments, the expression of one or more of IRF4, BLIMP1, and XBP1 is increased. In some embodiments, the modified expression is transient. In some embodiments, the modified expression is conditional. In some embodiments, the modified expression is inducible. Methods for altering gene expression are known in the art and described in more detail below.

In some embodiments, the method further comprises modifying the input cell to prevent class-switching of an endogenous antibody expressed in the input cell. In some embodiments, the modifying comprises reducing or eliminating the expression of activation-induced deaminase (AID), uracil DNA glycosylase, and/or apyrimidic/apurinic (AP)-endonucleases. In some embodiments, the modified expression is transient. In some embodiments, the modified expression is conditional. In some embodiments, the modified expression is inducible. In some embodiments, the modifying comprises or further comprises mutating (such as deleting all or a portion of) one or more switch regions in the gene encoding the endogenous antibody.

In some embodiments, the method further comprises modifying the input cell to prevent switching of an endogenous antibody expressed in the input cell from a membrane-anchored form to a secreted form. In some embodiments, the modifying comprises or further comprises mutating (such as deleting all or a portion of) the polyadenylation signal upstream of the M1 exon in the gene encoding the endogenous antibody.

In some embodiments, the method comprises introducing into the input cell a driving receptor, such as a recombinant receptor, comprising a ligand binding domain, wherein, upon ligand binding, the receptor is capable of inducing (i) a mitogenic or proliferative signal; and/or (ii) a signal that is capable of modulating the differentiation of the engineered B cell. In some embodiments, the receptor is encoded by one or more coding sequences contained in the one or more nucleic acid molecules encoding the exogenous protein. In some embodiments, the receptor is encoded by one or more coding sequences contained in one or more separate nucleic acid molecules from the one or more nucleic acid molecules encoding the exogenous protein, and the method further comprises introducing into the input cell the one or more nucleic acid molecules encoding the receptor.

IV. Compositions, Formulations, Kits, Devices, Methods, and Uses

Also provided are cells, cell populations, and compositions containing the cells produced by the provided methods.

Among the compositions are pharmaceutical compositions and formulations for administration, such as for adoptive cell therapy. Also provided are therapeutic methods for administrating the cells and compositions to subjects, e.g., patients.

Provided are methods and uses of the cells, including therapeutic methods and uses, such as in adoptive cell therapy. In some embodiments, the methods include administration of the cells or a composition containing the cells to a subject, tissue, or cell, such as one having, at risk for, or suspected of having a disease, condition or disorder. In some embodiments, the methods treat cancers and other diseases, conditions, and disorders. In some embodiments, the cells, populations, and compositions are administered to a subject having the particular disease or condition to be treated, e.g., via adoptive B cell therapy. In some embodiments, the cells or compositions are administered to the subject, such as a subject having or at risk for the disease or condition. In some aspects, the methods thereby treat, e.g., ameliorate one or more symptom of, the disease or condition, such as by lessening tumor burden in a cancer expressing an antigen recognized by the engineered B cell, or by reducing the viral load in an infection characterized by a viral antigen recognized by the engineered B cell.

Methods for administration of cells for adoptive cell therapy are known and may be used in connection with the provided methods and compositions. For example, adoptive T cell therapy methods, which can be adapted to methods for adoptive B cell therapy, are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

In some embodiments, the cell therapy, e.g., adoptive B cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive B cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

Also provided are pharmaceutical compositions for use in such methods.

In some embodiments, the cells and cell populations are administered to a subject in the form of a composition, such as a pharmaceutical composition. In some embodiments, the pharmaceutical composition further comprises other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cell populations are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

In some aspects, the choice of carrier in the pharmaceutical composition is determined in part by the particular recombinant receptor, vector, or engineered B cells, as well as by the particular method used to administer the vector or engineered B cells. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition.

In addition, buffering agents in some aspects are included in the composition. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

In certain embodiments, a pharmaceutical composition comprising a cell population described herein can be formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known to those of ordinary skill in the art. Such systems can avoid repeated administrations of the composition, thereby increasing convenience to the subject and the physician.

The pharmaceutical composition in some embodiments comprises the cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

The cells and compositions in some embodiments are administered using standard administration techniques, formulations, and/or devices. Provided are formulations and devices, such as syringes and vials, for storage and administration of the compositions. Administration can be autologous or heterologous. For example, immunoresponsive cells or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions of the cells in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the genetically engineered in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cell populations are administered prior to the one or more additional therapeutic agents. In some embodiments, the cell populations are administered after to the one or more additional therapeutic agents.

Once the cells are administered to a mammal (e.g., a human), the biological activity of the engineered B cell populations in some aspects is measured by any of a number of known methods. Parameters to assess include specific binding of an engineered or natural B cell or other immune cell to antigen, in vivo, e.g., by imaging, or ex vivo, e.g., by ELISA or flow cytometry. In certain embodiments, the ability of the engineered B cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

In certain embodiments, engineered B cells are modified in any number of ways, such that their therapeutic or prophylactic efficacy is increased. For example, the engineered recombinant receptor expressed by the engineered B cells can be conjugated either directly or indirectly through a linker to a targeting moiety. The practice of conjugating compounds, e.g., the recombinant receptor, to targeting moieties is known in the art. See, for instance, Wadwa et al., J. Drug Targeting 3:111 (1995), and U.S. Pat. No. 5,087,616.

V. Methods of Administration and Uses in Adoptive Cell Therapy

Provided are methods of administering the cells, populations, and compositions, and uses of such cells, populations, and compositions to treat or prevent diseases, conditions, and disorders, including infectious diseases and cancers. In some embodiments, the cells, populations, and compositions are administered to a subject or patient having the particular disease or condition to be treated, e.g., via the exogenous protein, e.g. therapeutic protein, secreted by cells in connection with the adoptive B cell therapy. In some embodiments, cells and compositions prepared by the provided methods, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an exogenous protein produced and/or secreted from an engineered B cell. In some embodiments, the exogenous protein secreted by the administered engineered B cells is a therapeutic agent known to or that does treat the disease or condition.

In some embodiments, the provided methods generally involve administering doses of the provided engineered B cells to subjects having a disease or condition, such as a disease or condition a component of which is specifically recognized by and/or treated by the exogenous protein secreted by the B cell, e.g., therapeutic protein, such as an antibody or antigen-binding fragment thereof. The administrations generally effects an improvement in one or more symptoms of the disease or condition and/or treat or prevent the disease or condition or symptom thereof.

Among the diseases, conditions, and disorders are tumors, including solid tumors, hematologic malignancies, and melanomas, and infectious diseases, such as infection with a virus or other pathogen, e.g., HIV, HCV, HBV, CMV, and parasitic disease. In some embodiments, the disease or condition is a tumor, cancer, malignancy, neoplasm, or other proliferative disease. Such diseases include but are not limited to hematological (or hematogenous) cancers including leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, plasmacytoma, Waldenstrom's macroglobulinemia, heavy chain disease, myelodysplastic syndrome, hairy cell leukemia and myelodysplasia, and solid tumors including sarcomas and carcinomas, including adrenocortical carcinoma, cholangiocarcinoma, fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, stomach cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, thyroid cancer (e.g., medullary thyroid carcinoma and papillary thyroid carcinoma), pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer (e.g., cervical carcinoma and pre-invasive cervical dysplasia), colorectal cancer, cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, esophageal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, kidney cancer, melanoma, cancer of the uterus (e.g., endometrial carcinoma), urothelial cancers (e.g., squamous cell carcinoma, transitional cell carcinoma, adenocarcinoma, ureter cancer, and urinary bladder cancer), and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, the disease or condition is an infectious disease or condition, such as, but not limited to, viral, retroviral, bacterial, and protozoal infections. Such diseases include but are not limited to infection with a pathogen selected from among *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, Astroviridae, *Babesia* genus, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia* genus, *Borrelia* spp, *Brucella* genus, *Brugia malayi*, Bunyaviridae family, *Burkholderia cepacia* and other *Burkholderia* species, *Burkholderia mallei*, *Burkholderia pseudomallei*, Caliciviridae family, *Campylobacter* genus, *Candida albicans*, *Candida* spp, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium* spp, *Clostridium tetani*, *Coccidioides* spp, coronaviruses, *Corynebacterium diphtheriae*, *Coxiella burnetii*, Crimean-Congo hemorrhagic fever virus, *Cryptococcus neoformans*, *Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis*, *Ehrlichia ewingii*, *Ehrlichia* genus, *Entamoeba histolytica*, *Enterococcus* genus, *Enterovirus* genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FPI prion, Filarioidea superfamily, Flaviviruses, *Francisella tularensis*, Fusobacterium genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Human T cell leukemia virus 1 (HTLV-1), Japanese encephalitis virus, JC virus, Junin virus, Kaposi's Sarcoma associated herpesvirus (KSHV), *Kingella kingae*, *Klebsiella granulomatis*, Kuru prion, Lassa virus,

*Legionella pneumophila, Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai, Microsporidia phylum, Molluscum contagiosum* virus (MCV), Mumps virus, *Mycobacterium leprae* and *Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi,* Orthomyxoviridae family (Influenza), *Paracoccidioides brasiliensis, Paragonimus* spp, *Paragonimus westermani,* Parvovirus B19, *Pasteurella* genus, *Plasmodium* genus, *Pneumocystis jirovecii,* Poliovirus, Rabies virus, Respiratory syncytial virus (RSV), Rhinovirus, rhinoviruses, *Rickettsia akari, Rickettsia* genus, *Rickettsia prowazekii, Rickettsia rickettsii, Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia* genus, *Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum, Varicella zoster* virus (VZV), *Varicella zoster* virus (VZV), Variola major or Variola minor, vCJD prion, Venezuelan equine encephalitis virus, *Vibrio cholerae*, West Nile virus, Western equine encephalitis virus, *Wuchereria bancrofti,* Yellow fever virus, *Yersinia enterocolitica, Yersinia pestis,* and *Yersinia pseudotuberculosis.*

In some embodiments, the disease or condition is HIV infection. In some embodiments, the HIV infection is HIV-1 or HIV-2 infection, including infection with any of the HIV groups, subtypes, or variants described herein. Exemplary HIV-1 groups include HIV-1 Group M, HIV-1 Group N, HIV-1 Group O, and HIV-1 Group P. Subtypes and recombinant forms thereof are known; exemplary subtypes include subtype A (including A1 and A2), subtype B, subtype C, and recombinant forms including CRF_AE. Exemplary HIV-2 groups include HIV-2 Group A, HIV-2 Group B, HIV-2 Group C, HIV-2 Group D, HIV-2 Group E, HIV-2 Group F, HIV-2 Group G, and HIV-2 Group H.

In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease multiple sclerosis, asthma, and/or a disease or condition associated with transplant.

As used herein, a "subject" is a mammal, such as a human or other animal, and typically is human. In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply necessarily complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

Methods for administration of cells for adoptive cell therapy are known and may be used in connection with the provided methods and compositions. For example, adoptive T cell therapy methods, which can be adapted for adoptive B cell therapy, are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive B cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive B cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical or similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjunctival injection, subconjunctival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, intrathoracic, intracranial, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or other agent, such as a cytotoxic or therapeutic agent. Thus, the cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents.

In some embodiments, the methods comprise administration of a chemotherapeutic agent, e.g., a conditioning chemotherapeutic agent, for example, to reduce tumor burden prior to the dose administrations.

Once the cells are administered to the subject (e.g., human), the biological activity of the engineered B cell populations in some aspects is measured by any of a number of known methods. In some embodiments, the biological activity of the cells can be measured by assaying for expression and/or secretion of the exogenous protein, such as therapeutic protein. In certain embodiments, the biological activity of the cells also can be measured by assaying expression and/or secretion of certain cytokines, such as IFNγ, IL-2, IL-4, IL-6, IL-12 and TNFα. In some aspects the biological activity is measured by assessing clinical outcome, such as reduction in tumor burden or load. In some aspects, toxic outcomes, persistence and/or expansion of the cells, and/or presence or absence of a host immune response, are assessed.

In some embodiments, the methods comprise inducing the engineered B cell to increase production and/or secretion of the exogenous protein. In some embodiments, the inducing comprises administering to the subject an agent that binds to the ligand binding domain of an endogenous B cell receptor expressed in the engineered B cell. In some embodiments, the agent is a vaccine recognized by an endogenous B cell receptor, such as any as described. In some embodiments, the inducing comprises administering to the subject an agent that binds to the ligand binding domain of the driving receptor, such as a recombinant or chimeric receptor, expressed in the engineered B cell. In some embodiments, the binding of the ligand to the driving receptor of the engineered B cell induces the engineered B cell to differentiate into a plasmablast or a plasma cell. In some embodiments, the engineered B cell is a plasmablast or plasma cell. In some embodiments, the exogenous protein is under the control of an endogenous immunoglobulin promoter or a constitutively active promoter. In some embodiments, the exogenous protein is under the control of an inducible promoter, and the method further comprises administering to the subject an agent that activates the inducible promoter.

In some embodiments, the method results in a duration of action (the length of time that the particular method is effective) in a subject of at least about 1 month, at least 2 months, at least 6 months, at least a year, at least 2 years or more. In some embodiments, a single administration of the engineered B cell or composition to the subject results in an increased duration of action in the subject compared to the maximum tolerable duration of action (duration of action for the maximum tolerable dose of a therapeutic) resulting from a single direct administration of the exogenous protein to the subject. In some embodiments, the increase is at least 1.2-fold, 1.5-fold, 2-fold, 3-fold, 4-fold, or 5-fold.

Dosing

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells are administered at or within a tolerated difference of a desired dose of total cells, such as a desired dose of B cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio, e.g., within a certain tolerated difference or error of such a ratio.

In some embodiments, the cells are administered at or within a tolerated difference of a desired dose of one or more of the individual populations or sub-types of cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of B cells.

In certain embodiments, the cells, or individual populations of sub-types of cells, are administered to the subject at a range of about at least one million to about at least 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about at least 100 million cells to about at least 50 billion cells (e.g., about at least 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1 \times 10^5$ cells/kg, $1.5 \times 10^5$ cells/kg, $2 \times 10^5$ cells/kg, or $1 \times 10^6$ cells/kg body weight. For example, in some embodiments, the cells are administered at, or within a certain range of error of, between at or about $10^4$ and at or about $10^9$ B cells/kilograms (kg) body weight, such as between $10^5$ and $10^6$ B cells/kg body weight, for example, at or about $1 \times 10^5$ B cells/kg, $1.5 \times 10^5$ B cells/kg, $2 \times 10^5$ B cells/kg, or $1 \times 10^6$ B cells/kg body weight.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of several days, such as no more than three days, such as once a day for three days or for two days or by multiple infusions over a single day period.

Thus, in some aspects, the cells are administered in a single pharmaceutical composition.

In some embodiments, the cells are administered in a plurality of compositions, collectively containing the cells of a single dose.

Thus, one or more of the doses in some aspects may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, multiple doses are given, e.g., by administering a first dose and one or more subsequent doses, with each subsequent dose given at a point in time that is greater than about 28 days after the administration of the first or prior dose.

In some embodiments, the dose contains a number of cells, number of engineered B cells, or number of peripheral blood mononuclear cells (PBMCs) in the range from about $10^5$ to about $10^6$ of such cells per kilogram body weight of the subject, and/or a number of such cells that is no more than about $10^5$ or about $10^6$ such cells per kilogram body weight of the subject. For example, in some embodiments, the first or subsequent dose includes less than or no more than at or about $1 \times 10^5$, at or about $2 \times 10^5$, at or about $5 \times 10^5$, or at or about $1 \times 10^6$ of such cells per kilogram body weight of the subject. In some embodiments, the first dose includes at or about $1 \times 10^5$, at or about $2 \times 10^5$, at or about $5 \times 10^5$, or at or about $1 \times 10^6$ of such cells per kilogram body weight of the subject, or a value within the range between any two of the foregoing values. In particular embodiments, the numbers and/or concentrations of cells refer to the number of engineered B cells. In other embodiments, the numbers and/or concentrations of cells refer to the number or concentration of all cells, B cells, or peripheral blood mononuclear cells (PBMCs) administered.

In some embodiments, for example, where the subject is a human, the dose includes fewer than about $1 \times 10^8$ total engineered B cells, B cells, or peripheral blood mononuclear cells (PBMCs), e.g., in the range of about $1 \times 10^6$ to $1 \times 10^8$ such cells, such as $2 \times 10^6$, $5 \times 10^6$, $1 \times 10^7$, $5 \times 10^7$, or $1 \times 10^8$ or total such cells, or the range between any two of the foregoing values.

In some embodiments, the dose contains fewer than about $1 \times 10^8$ total engineered B cells, B cells, or peripheral blood mononuclear cells (PBMCs) cells per m² of the subject, e.g., in the range of about $1 \times 10^6$ to $1 \times 10^8$ such cells per m² of the subject, such as $2\times10^6$, $5\times10^6$, $1\times10^7$, $5\times10^7$, or $1\times10^8$ such cells per $m^2$ of the subject, or the range between any two of the foregoing values.

In certain embodiments, the number of cells, engineered B cells, B cells, or peripheral blood mononuclear cells (PBMCs) in the dose is greater than about $1\times10^6$ such cells per kilogram body weight of the subject, e.g., $2\times10^6$, $3\times10^6$, $5\times10^6$, $1\times10^7$, $5\times10^7$, $1\times10^8$, $1\times10^9$, or $1\times10^{10}$ such cells per kilogram of body weight and/or, $1\times10^8$, or $1\times10^9$, $1\times10^{10}$ such cells per $m^2$ of the subject or total, or the range between any two of the foregoing values.

In some aspects, the size of the dose is determined based on one or more criteria such as response of the subject to prior treatment, e.g. antiviral therapy or chemotherapy, disease burden in the subject, such as viral load or tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

VI. Modification of Gene Expression, Activity, and/or Function

In some embodiments, expression, activity, and/or function of one or more genes is modified in an engineered B cell described herein. Provided are methods for effecting such modifications.

In some embodiments, the modification is gene repression. In some embodiments, the gene repression is carried out by effecting a disruption in the gene (gene editing), such as a knock-out, insertion, missense or frameshift mutation, such as a biallelic frameshift mutation, deletion of all or part of the gene, e.g., one or more exon or portion thereof, and/or knock-in. Such disruptions in some embodiments are effected by sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of a gene or a portion thereof.

In some embodiments, the gene repression is carried out by introducing an inhibitory nucleic acid molecule targeting the gene. In some embodiments, the inhibitory nucleic acid includes a small interfering RNA (siRNA), a microRNA-adapted shRNA, a short hairpin RNA (shRNA), a hairpin siRNA, a microRNA (miRNA-precursor) or a microRNA (miRNA).

In some embodiments, the modification is gene activation. In some embodiments, the gene activation is carried out by increasing the copy number of the gene, such as knock-in of the gene, or by activating the transcription and/or translation of the gene. Knock-in in some embodiments is effected by RNA-guided nucleases such as a CRISPR-associated nuclease (Cas) in combination with a donor template comprising a coding sequence for the gene. Transcriptional activation in some embodiments is effected by RNA-guided nucleases such as a CRISPR-associated nuclease (Cas) comprising a nuclease-inactivating mutation and fused to a transcriptional activator.

1. Techniques for Gene Repression

In some embodiments, the repression of the expression, activity, and/or function of the gene is carried out by disrupting the gene. In some aspects, the gene is disrupted so that its expression is reduced by at least at or about 20, 30, or 40%, generally at least at or about 50, 60, 70, 80, 90, or 95% as compared to the expression in the absence of the gene disruption or in the absence of the components introduced to effect the disruption.

In some embodiments, gene disruption is carried out by induction of one or more double-stranded breaks and/or one or more single-stranded breaks in the gene, typically in a targeted manner. In some embodiments, the double-stranded or single-stranded breaks are made by a nuclease, e.g. an endonuclease, such as a gene-targeted nuclease. In some aspects, the breaks are induced in the coding region of the gene, e.g. in an exon. For example, in some embodiments, the induction occurs near the N-terminal portion of the coding region, e.g. in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the gene. For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/or a premature stop codon results in repression of the expression, activity, and/or function of the gene.

In some embodiments, the repression is transient or reversible, such that expression of the gene is restored at a later time. In other embodiments, the repression is not reversible or transient, e.g., is permanent.

In some embodiments, gene repression is achieved using antisense techniques, such as by RNA interference (RNAi), short interfering RNA (siRNA), short hairpin (shRNA), and/or ribozymes are used to selectively suppress or repress expression of the gene. siRNA technology includes that based on RNAi utilizing a double-stranded RNA molecule having a sequence homologous with the nucleotide sequence of mRNA which is transcribed from the gene, and a sequence complementary with the nucleotide sequence. siRNA generally is homologous/complementary with one region of mRNA which is transcribed from the gene, or may be siRNA including a plurality of RNA molecules which are homologous/complementary with different regions.

DNA-Targeting Molecules and Complexes; Targeted Endonucleases

In some embodiments, the repression is achieved using a DNA-targeting molecule, such as a DNA-binding protein or DNA-binding nucleic acid, or complex, compound, or composition, containing the same, which specifically binds to or hybridizes to the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease.

Zinc finger, TALE, and CRISPR system binding domains can be "engineered" to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

In some embodiments, the DNA-targeting molecule, complex, or combination contains a DNA-binding molecule and one or more additional domain, such as an effector domain to facilitate the repression or disruption of the gene. For example, in some embodiments, the gene disruption is carried out by fusion proteins that comprise DNA-binding proteins and a heterologous regulatory domain or functional fragment thereof. In some aspects, domains include, e.g., transcription factor domains such as activators, repressors, co-activators, co-repressors, silencers, oncogenes, DNA repair enzymes and their associated factors and modifiers, DNA rearrangement enzymes and their associated factors and modifiers, chromatin associated proteins and their modifiers, e.g. kinases, acetylases and deacetylases, and DNA modifying enzymes, e.g. methyltransferases, topoisomerases, helicases, ligases, kinases, phosphatases, polymerases, endonucleases, and their associated factors and modifiers. See, for example, U.S. Patent Application Publication Nos. 20050064474; 20060188987 and 2007/0218528, incorporated by reference in their entireties herein, for details regarding fusions of DNA-binding domains and nuclease cleavage domains. In some aspects, the additional domain is a nuclease domain. Thus, in some embodiments, gene disruption is facilitated by gene or genome editing, using engineered proteins, such as nucleases and nuclease-containing complexes or fusion proteins, composed of sequence-specific DNA-binding domains fused to or complexed with non-specific DNA-cleavage molecules such as nucleases.

In some aspects, these targeted chimeric nucleases or nuclease-containing complexes carry out precise genetic modifications by inducing targeted double-stranded breaks or single-stranded breaks, stimulating the cellular DNA-repair mechanisms, including error-prone non-homologous end joining (NHEJ) and homology-directed repair (HDR). In some embodiments the nuclease is an endonuclease, such as a zinc finger nuclease (ZFN), TALE nuclease (TALEN), an RNA-guided endonuclease (RGEN), such as a CRISPR-associated (Cas) protein, or a meganuclease.

In some embodiments, a donor nucleic acid, e.g., a donor plasmid or nucleic acid encoding the exogenous protein and/or recombinant receptor, is provided and is inserted by HDR at the site of gene editing following the introduction of the DSBs. Thus, in some embodiments, the disruption of the gene and the introduction of the nucleic acid encoding the exogenous protein and/or recombinant receptor are carried out simultaneously, whereby the gene is disrupted in part by knock-in or insertion of the nucleic acid encoding the exogenous protein and/or recombinant receptor.

In some embodiments, no donor nucleic acid is provided. In some aspects, NHEJ-mediated repair following introduction of DSBs results in insertion or deletion mutations that can cause gene disruption, e.g., by creating missense mutations or frameshifts.

ZFPs and ZFNs; TALs, TALEs, and TALENs

In some embodiments, the DNA-targeting molecule includes a DNA-binding protein such as one or more zinc finger protein (ZFP) or transcription activator-like protein (TAL), fused to an effector protein such as an endonuclease. Examples include ZFNs, TALEs, and TALENs. See Lloyd et al., Frontiers in Immunology, 4(221), 1-7 (2013).

In some embodiments, the DNA-targeting molecule comprises one or more zinc-finger proteins (ZFPs) or domains thereof that bind to DNA in a sequence-specific manner A ZFP or domain thereof is a protein or domain within a larger protein, that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP.

Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

In some aspects, repression of the gene is carried out by contacting a first target site in the gene with a first ZFP, thereby repressing the gene. In some embodiments, the target site in the gene is contacted with a fusion ZFP comprising six fingers and the regulatory domain, thereby inhibiting expression of the gene.

In some embodiments, the step of contacting further comprises contacting a second target site in the gene with a second ZFP. In some aspects, the first and second target sites are adjacent. In some embodiments, the first and second ZFPs are covalently linked. In some aspects, the first ZFP is a fusion protein comprising a regulatory domain or at least two regulatory domains. In some embodiments, the first and second ZFPs are fusion proteins, each comprising a regulatory domain or each comprising at least two regulatory domains. In some embodiments, the regulatory domain is a transcriptional repressor, a transcriptional activator, an endonuclease, a methyl transferase, a histone acetyltransferase, or a histone deacetylase.

In some embodiments, the ZFP is encoded by a ZFP nucleic acid operably linked to a promoter. In some aspects, the method further comprises the step of first administering the nucleic acid to the cell in a lipid:nucleic acid complex or as naked nucleic acid. In some embodiments, the ZFP is encoded by an expression vector comprising a ZFP nucleic acid operably linked to a promoter. In some embodiments, the ZFP is encoded by a nucleic acid operably linked to an inducible promoter. In some aspects, the ZFP is encoded by a nucleic acid operably linked to a weak promoter.

In some embodiments, the target site is upstream of a transcription initiation site of the gene. In some aspects, the target site is adjacent to a transcription initiation site of the gene. In some aspects, the target site is adjacent to an RNA polymerase pause site downstream of a transcription initiation site of the gene.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type IIS restriction enzyme and one or more zinc finger binding domains, which may or may not be engineered. In some embodiments, the cleavage domain is from the Type IIS restriction endonuclease Fok I. Fok I generally catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31, 978-31, 982.]

In some embodiments, ZFNs target a gene present in the engineered B cell. In some aspects, the ZFNs efficiently generate a double strand break (DSB), for example at a predetermined site in the coding region of the gene. Typical regions targeted include exons, regions encoding N-terminal regions, first exon, second exon, and promoter or enhancer regions. In some embodiments, transient expression of the ZFNs promotes highly efficient and permanent disruption of the target gene in the engineered B cells. In particular, in some embodiments, delivery of the ZFNs results in the permanent disruption of the gene with efficiencies surpassing 50%.

Many gene-specific engineered zinc fingers are available commercially. For example, Sangamo Biosciences (Richmond, Calif., USA) has developed a platform (CompoZr®) for zinc-finger construction in partnership with Sigma-Aldrich (St. Louis, Mo., USA), allowing investigators to bypass zinc-finger construction and validation altogether, and provides specifically targeted zinc fingers for thousands of proteins. Gaj et al., *Trends in Biotechnology*, 2013, 31(7), 397-405. In some embodiments, commercially available zinc fingers are used or are custom designed. (See, for example, Sigma-Aldrich catalog numbers CSTZFND, CSTZFN, CTI1-1KT, and PZD0020).

TALEs and TALENs

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 20110301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known. See, U.S. Patent Publication No. 20110301073. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE-nuclease (TALEN). In some aspects the TALEN is a fusion protein comprising a DNA-binding domain derived from a TALE and a nuclease catalytic domain to cleave a nucleic acid target sequence. In some embodiments, the TALE DNA-binding domain has been engineered to bind a target sequence within genes that encode the target antigen and/or the immunosuppressive molecule. For example, in some aspects, the TALE DNA-binding domain may target CD38 and/or an adenosine receptor, such as A2AR.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation (Critchlow and Jackson, *Trends Biochem Sci*. 1998 October; 23(10):394-8) or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., *Trends in Biotechnology*, 2013, 31(7), 397-405). A library of TALENs targeting 18,740 human protein-coding genes has been constructed (Kim et al., *Nature Biotechnology*. 31, 251-258 (2013)). Custom-designed TALE arrays are commercially available through Cellectis Bioresearch (Paris, France), Transposagen Biopharmaceuticals (Lexington, Ky., USA), and Life Technologies (Grand Island, N.Y., USA). Specifically, TALENs that target CD38 are commercially available (See Gencopoeia, catalog numbers HTN222870-1, HTN222870-2, and HTN222870-3, available on the World Wide Web at www.genecopoeia.com/product/search/detail.php?prt=26&cid=&key=HTN222870). Exemplary molecules are described, e.g., in U.S. Patent Publication Nos. US 2014/0120622, and 2013/0315884.

In some embodiments the TALENs are introduced as transgenes encoded by one or more plasmid vectors. In some aspects, the plasmid vector can contain a selection marker which provides for identification and/or selection of cells which received said vector.

RGENs (CRISPR/Cas Systems)

In some embodiments, the repression is carried out using one or more DNA-binding nucleic acids, such as disruption via an RNA-guided endonuclease (RGEN), or other form of repression by another RNA-guided effector molecule. For example, in some embodiments, the repression is carried out using clustered regularly interspaced short palindromic repeats (CRISPR) and CRISPR-associated (Cas) proteins. See Sander and Joung, *Nature Biotechnology*, 32(4): 347-355.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

In some embodiments, the CRISPR/Cas nuclease or CRISPR/Cas nuclease system includes a non-coding RNA molecule (guide) RNA, which sequence-specifically binds to DNA, and a Cas protein (e.g., Cas9), with nuclease functionality (e.g., two nuclease domains).

In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*.

In some embodiments, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. In some embodiments, the target site is selected based on its location immediately 5' of a protospacer adjacent motif (PAM) sequence, such as typically NGG, or NAG. In this respect, the gRNA is targeted to the desired sequence by modifying the first 20 nucleotides of the guide RNA to correspond to the target DNA sequence.

In some embodiments, the CRISPR system induces DSBs at the target site, followed by disruptions as discussed herein. In other embodiments, Cas9 variants, deemed "nickases" are used to nick a single strand at the target site. In some aspects, paired nickases are used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

In general, a CRISPR system is characterized by elements that promote the formation of a CRISPR complex at the site of a target sequence. Typically, the In the context of formation of a CRISPR complex, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The target sequence may comprise any polynucleotide, such as DNA or RNA polynucleotides. In some embodiments, the target sequence is located in the nucleus or cytoplasm of the cell. In some embodiments, the target sequence may be within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of the CRISPR complex.

As with the target sequence, in some embodiments, complete complementarity is not necessarily needed. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of the CRISPR system are introduced into the cell such that expression of the elements of the CRISPR system direct formation of the CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. In some embodiments, CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of the CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to the cell.

In some embodiments, a vector comprises a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb 1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from S. pyogenes or S. pneumoniae. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. In some embodiments, one or more codons (e.g. 1, 2, 3, 4, 5, 10, 15, 20, 25, 50, or more, or all codons) in a sequence encoding the CRISPR enzyme correspond to the most frequently used codon for a particular amino acid.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of the CRISPR complex to a target sequence may be assessed by any suitable assay. For example, the components of the CRISPR system sufficient to form the CRISPR complex, including the guide sequence to be tested, may be provided to the cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of the CRISPR complex, including the guide sequence to be tested and a control guide sequence different from the test guide sequence, and comparing binding or rate of cleavage at the target sequence between the test and control guide sequence reactions.

A guide sequence may be selected to target any target sequence. In some embodiments, the target sequence is a sequence within a genome of a cell. Exemplary target sequences include those that are unique in the target genome. In some embodiments, a guide sequence is selected to reduce the degree of secondary structure within the guide sequence. Secondary structure may be determined by any suitable polynucleotide folding algorithm.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences.

Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In some aspects, loop forming sequences for use in hairpin structures are four nucleotides in length, and have the sequence GAAA. However, longer or shorter loop sequences may be used, as may alternative sequences. In some embodiments, the sequences include a nucleotide triplet (for example, AAA), and an additional nucleotide (for example C or G). Examples of loop forming sequences include CAAA and AAAG. In some embodiments, the transcript or transcribed polynucleotide sequence has at least two or more hairpins. In some embodiments, the transcript has two, three, four or five hairpins. In a further embodiment, the transcript has at most five hairpins. In some embodiments, the single transcript further includes a transcription termination sequence, such as a polyT sequence, for example six T nucleotides.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CR ISPR enzyme are described in US20110059502, incorporated herein by reference. In some embodiments, a tagged CRISPR enzyme is used to identify the location of a target sequence.

In some embodiments, a CRISPR enzyme in combination with (and optionally complexed with) a guide sequence is delivered to the cell.

In some aspects, target polynucleotides are modified in a eukaryotic cell. In some embodiments, the method comprises allowing the CRISPR complex to bind to the target polynucleotide to effect cleavage of said target polynucleotide thereby modifying the target polynucleotide, wherein the CRISPR complex comprises the CRISPR enzyme complexed with a guide sequence hybridized to a target sequence within said target polynucleotide, wherein said guide sequence is linked to a tracr mate sequence which in turn hybridizes to a tracr sequence.

In some aspects, the methods include modifying expression of a polynucleotide in a eukaryotic cell. In some embodiments, the method comprises allowing the CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence.

Delivery of Nucleic Acids Encoding the Gene Disrupting Molecules and Complexes

In some aspects, a nucleic acid encoding the DNA-targeting molecule, complex, or combination, is administered or introduced to the cell. The nucleic acid typically is administered in the form of an expression vector, such as a viral expression vector. In some aspects, the expression vector is a retroviral expression vector, an adenoviral expression vector, a DNA plasmid expression vector, or an AAV expression vector. In some aspects, one or more polynucleotides encoding the disruption molecule or complex, such as the DNA-targeting molecule, is delivered to the cell. In some aspects, the delivery is by delivery of one or more vectors, one or more transcripts thereof, and/or one or proteins transcribed therefrom, is delivered to the cell.

In some embodiments, the polypeptides are synthesized in situ in the cell as a result of the introduction of polynucleotides encoding the polypeptides into the cell. In some aspects, the polypeptides could be produced outside the cell and then introduced thereto. Methods for introducing a polynucleotide construct into animal cells are known and include, as non-limiting examples stable transformation methods wherein the polynucleotide construct is integrated into the genome of the cell, transient transformation methods wherein the polynucleotide construct is not integrated into the genome of the cell, and virus mediated methods. In some embodiments, the polynucleotides may be introduced into the cell by for example, recombinant viral vectors (e.g. retroviruses, adenoviruses), liposome and the like. For example, in some aspects, transient transformation methods include microinjection, electroporation, or particle bombardment. In some embodiments, the polynucleotides may be included in vectors, more particularly plasmids or virus, in view of being expressed in the cells.

In some embodiments, viral and non-viral based gene transfer methods can be used to introduce nucleic acids in mammalian cells or target tissues. Such methods can be used to administer nucleic acids encoding components of a CRISPR, ZFP, ZFN, TALE, and/or TALEN system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon. TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer.

In some aspects, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into the cell to encode a gene product which serves as a marker by which to measure the alteration or modification of expression of the gene product. In a further embodiment, the DNA molecule encoding the gene product may be introduced into the cell via a vector. In some embodiments, the gene product is luciferase. In a further embodiment, the expression of the gene product is decreased.

Inhibitory Nucleic Acid Molecules

In some embodiments, gene repression is achieved using an inhibitory nucleic acid molecule that is an RNA interfering agent, which can be used to selectively suppress or repress expression of the gene. For example, gene repression can be carried out by RNA interference (RNAi), short interfering RNA (siRNA), short hairpin (shRNA), antisense, and/or ribozymes. In some embodiments, RNA interfering agents also can include other RNA species that can be processed intracellularly to produce shRNAs including, but not limited to, RNA species identical to a naturally occurring miRNA precursor or a designed precursor of an miRNA-like RNA.

In some embodiments, an RNA interfering agent is at least a partly double-stranded RNA having a structure characteristic of molecules that are known in the art to mediate inhibition of gene expression through an RNAi mechanism or an RNA strand comprising at least partially complementary portions that hybridize to one another to form such a structure. When an RNA contains complementary regions that hybridize with each other, the RNA will be said to self-hybridize. In some embodiments, an inhibitory nucleic acid, such as an RNA interfering agent, includes a portion that is substantially complementary to a target gene. In some embodiments, an RNA interfering agent targeted to a transcript can also be considered targeted to the gene that encodes and directs synthesis of the transcript. In some embodiments, a target region can be a region of a target transcript that hybridizes with an antisense strand of an RNA interfering agent. In some embodiments, a target transcript can be any RNA that is a target for inhibition by RNA interference.

In some embodiments, an RNA interfering agent is considered to be "targeted" to a transcript and to the gene that encodes the transcript if (1) the RNAi agent comprises a portion, e.g., a strand, that is at least approximately 80%, approximately 85%, approximately 90%, approximately 91%, approximately 92%, approximately 93%, approximately 94%, approximately 95%, approximately 96%, approximately 97%, approximately 98%, approximately 99%, or approximately 100% complementary to the transcript over a region about 15-29 nucleotides in length, e.g., a region at least approximately 15, approximately 17, approximately 18, or approximately 19 nucleotides in length; and/or (2) the Tm of a duplex formed by a stretch of 15 nucleotides of one strand of the RNAi agent and a 15 nucleotide portion of the transcript, under conditions (excluding temperature) typically found within the cytoplasm or nucleus of mammalian cells is no more than approximately 15° C. lower or no more than approximately 10° C. lower, than the Tm of a duplex that would be formed by the same 15 nucleotides of the RNA interfering agent and its exact complement; and/or (3) the stability of the transcript is reduced in the presence of the RNA interfering agent as compared with its absence.

In some embodiments, an RNA interfering agent optionally includes one or more nucleotide analogs or modifications. One of ordinary skill in the art will recognize that RNAi agents can include ribonucleotides, deoxyribonucleotide, nucleotide analogs, modified nucleotides or backbones, etc. In some embodiments, RNA interfering agents may be modified following transcription. In some embodiments, RNA interfering agents can contain one or more strands that hybridize or self-hybridize to form a structure that includes a duplex portion between about 15-29 nucleotides in length, optionally having one or more mismatched or unpaired nucleotides within the duplex.

In some embodiments, the term "short, interfering RNA" (siRNA) refers to a nucleic acid that includes a double-stranded portion between about 15-29 nucleotides in length and optionally further includes a single-stranded overhang {e.g., 1-6 nucleotides in length) on either or both strands. In some embodiments, the double-stranded portion can be between 17-21 nucleotides in length, e.g., 19 nucleotides in length. In some embodiments, the overhangs are present on the 3' end of each strand, can be about or approximately 2 to 4 nucleotides long, and can be composed of DNA or nucleotide analogs. An siRNA may be formed from two RNA strands that hybridize together, or may alternatively be generated from a longer double-stranded RNA or from a single RNA strand that includes a self-hybridizing portion, such as a short hairpin RNA. One of ordinary skill in the art will appreciate that one or more mismatches or unpaired nucleotides can be present in the duplex formed by the two siRNA strands. In some embodiments, one strand of an siRNA (the "antisense" or "guide" strand) includes a portion that hybridizes with a target nucleic acid, e.g., an mRNA transcript. In some embodiments, the antisense strand is perfectly complementary to the target over about 15-29 nucleotides, sometimes between 17-21 nucleotides, e.g., 19 nucleotides, meaning that the siRNA hybridizes to the target transcript without a single mismatch over this length. However, one of ordinary skill in the art will appreciate that one or more mismatches or unpaired nucleotides may be present in a duplex formed between the siRNA strand and the target transcript.

In some embodiments, a short hairpin RNA (shRNA) is a nucleic acid molecule comprising at least two complementary portions hybridized or capable of hybridizing to form a duplex structure sufficiently long to mediate RNAi (typically between 15-29 nucleotides in length), and at least one single-stranded portion, typically between approximately 1 and 10 nucleotides in length that forms a loop connecting the ends of the two sequences that form the duplex. In some embodiments, the structure may further comprise an overhang. In some embodiments, the duplex formed by hybridization of self-complementary portions of the shRNA may have similar properties to those of siRNAs and, in some cases, shRNAs can be processed into siRNAs by the conserved cellular RNAi machinery. Thus shRNAs can be precursors of siRNAs and can be similarly capable of inhibiting expression of a target transcript. In some embodiments, an shRNA includes a portion that hybridizes with a target nucleic acid, e.g., an mRNA transcript, and can be perfectly complementary to the target over about 15-29 nucleotides, sometimes between 17-21 nucleotides, e.g., 19 nucleotides. However, one of ordinary skill in the art will appreciate that one or more mismatches or unpaired nucleotides may be present in a duplex formed between the shRNA strand and the target transcript.

2. Techniques for Gene Activation

In some embodiments, the enhancement of the expression, activity, and/or function of the gene is carried out by modifying the expression of the endogenous gene, by introducing an exogenous copy of the gene, or by stabilizing and/or de-repressing the gene product. In some aspects, the expression and/or activity of gene is increased by at least or by about 20, 30, or 40%, generally at least or about 50, 60, 70, 80, 90, or 95% as compared to the expression and/or activity in the absence of the gene activation or in the absence of the components introduced to effect the enhancement.

In some embodiments, the expression of the endogenous gene is modified by disrupting a negative regulatory element associated with the gene or a negative transcriptional regulator of the gene, such as by any of the methods of targeted disruption described herein. In some embodiments, the expression of the endogenous gene is modified by introducing a positive regulatory element in association with the gene or a positive transcriptional activator of the gene. Methods for introducing genetic modifications and expressing exogenous proteins are well known in the art.

In some embodiments, the activation is transient or reversible, such that expression of the gene is reduced to unmodified levels at a later time. In other embodiments, the activation is not reversible or transient, e.g., is permanent.

In some embodiments, gene activation is achieved using antisense techniques, such as by RNA interference (RNAi), short interfering RNA (siRNA), short hairpin (shRNA), and/or ribozymes used to selectively suppress or repress expression of negative regulators of the gene.

DNA-Targeting Molecules and Complexes; Targeted Endonucleases

In some embodiments, the activation is achieved using a DNA-targeting molecule, such as a DNA-binding protein or DNA-binding nucleic acid, or complex, compound, or composition, containing the same, which specifically binds to or hybridizes to a regulatory element associated with the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease.

In some embodiments, the DNA-targeting molecule, complex, or combination contains a DNA-binding molecule and one or more additional domain, such as an effector domain to facilitate the activation of the gene. For example, in some embodiments, the gene activation is carried out by fusion proteins that comprise DNA-binding proteins and a heterologous regulatory domain or functional fragment thereof. In some aspects, domains include, e.g., transcription factor domains such as activators, co-activators, oncogenes, DNA repair enzymes and their associated factors and modifiers, DNA rearrangement enzymes and their associated factors and modifiers, chromatin associated proteins and their modifiers, e.g. kinases, acetylases and deacetylases, and DNA modifying enzymes, e.g. methyltransferases, topoisomerases, helicases, ligases, kinases, phosphatases, polymerases, endonucleases, and their associated factors and modifiers.

RGENs (CRISPR/Cas Systems)

In some embodiments, the activation is carried out using one or more DNA-binding nucleic acids, such as activation via an RNA-guided endonuclease (RGEN), or other form of activation by another RNA-guided effector molecule. For example, in some embodiments, the activation is carried out using CRISPR-associated (Cas) proteins. See Perez-Pinera, P., et al. (2013) *Nature methods*, 10(10): 973-976.

Both RuvC- and HNH-nuclease domains can be rendered inactive by point mutations (D10A and H840A in SpCas9), resulting in a nuclease dead Cas9 (dCas9) molecule that cannot cleave target DNA. The dCas9 molecule retains the ability to bind to target DNA based on the gRNA targeting sequence. dCas9 can be tagged with transcriptional activators, and targeting these dCas9 fusion proteins to the promoter region results in robust transcriptional activation of downstream target genes. The simplest dCas9-based activators and repressors consist of dCas9 fused directly to a single transcriptional activator, (e.g. VP64). Additionally, more elaborate activation strategies have been developed which result in greater activation of target genes in mammalian cells. These include: co-expression of epitope-tagged dCas9 and antibody-activator effector proteins (e.g. SunTag system), dCas9 fused to several different activation domains in series (e.g. dCas9-VPR) or co-expression of dCas9-VP64 with a "modified scaffold" gRNA and additional RNA-binding "helper activators" (e.g. SAM activators). Importantly, dCas9-mediated gene activation is reversible, since it does not permanently modify the genomic DNA.

VII. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, "repression" of gene expression refers to the elimination or reduction of expression of one or more gene products encoded by the subject gene in a cell, compared to the level of expression of the gene product in the absence of the repression. Exemplary gene products include mRNA and protein products encoded by the gene. Repression in some cases is transient or reversible and in other cases is permanent. Repression in some cases is of a functional or full-length protein or mRNA, despite the fact that a truncated or non-functional product may be produced. In some embodiments herein, gene activity or function, as opposed to expression, is repressed. Gene repression is generally induced by artificial methods, i.e., by addition or introduction of a compound, molecule, complex, or composition, and/or by disruption of nucleic acid of or associated with the gene, such as at the DNA level. Exemplary methods for gene repression include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination.

As used herein, a "disruption" of a gene refers to a change in the sequence of the gene, at the DNA level. Examples include insertions, mutations, and deletions. The disruptions typically result in the repression and/or complete absence of expression of a normal or "wild type" product encoded by the gene. Exemplary of such gene disruptions are insertions, frameshift and missense mutations, deletions, knock-in, and knock-out of the gene or part of the gene, including deletions of the entire gene. Such disruptions can occur in the coding region, e.g., in one or more exons, resulting in the inability to produce a full-length product, functional product, or any product, such as by insertion of a stop codon. Such disruptions may also occur by disruptions in the promoter or enhancer or other region affecting activation of transcription, so as to prevent transcription of the gene. Gene disruptions include gene targeting, including targeted gene inactivation by homologous recombination.

As used herein, the term "introducing" encompasses a variety of methods of introducing DNA into a cell, either in vitro or in vivo, such methods including transformation, transduction, transfection, and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se.

As used herein, a subject includes any living organism, such as humans and other mammals. Mammals include, but are not limited to, humans, and non-human animals, including farm animals, sport animals, rodents and pets.

As used herein, a composition refers to any mixture of two or more products, substances, or compounds, including cells. It may be a solution, a suspension, liquid, powder, a paste, aqueous, non-aqueous or any combination thereof.

As used herein, the terms "treatment," "treat," and "treating," refer to complete or partial amelioration or reduction of a disease or condition or disorder, or a symptom, adverse effect or outcome, or phenotype associated therewith. In certain embodiments, the effect is therapeutic, such that it partially or completely cures a disease or condition or adverse symptom attributable thereto.

As used herein, a "therapeutically effective amount" of a compound or composition or combination refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

In some embodiments, a decrease in expression of one or markers refers to loss of 1 $\log^{10}$ in the mean fluorescence intensity and/or decrease of percentage of cells that exhibit the marker of at least about 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20 and 100% when compared to a reference cell population. In some embodiments, a cell population positive for one or markers refers to a percentage of cells that exhibit the marker of at least about 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 50 and 100% when compared to a reference cell population.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

VIII. Exemplary Embodiments

Embodiment 1. An engineered B cell comprising one or more nucleic acid molecules comprising one or more coding sequences encoding an exogenous protein under the control of one or more elements to effect secretion of the exogenous protein from the cell, wherein the exogenous protein is not an antibody.

Embodiment 2. An engineered B cell comprising one or more nucleic acid molecules comprising one or more coding sequences encoding an exogenous protein, wherein expression of the exogenous protein in the engineered B cell is conditional.

Embodiment 3. An engineered B cell comprising one or more nucleic acid molecules comprising one or more coding sequences encoding an exogenous protein, wherein the engineered B cell expresses an endogenous antibody and comprises a modification that prevents class-switching of the endogenous antibody and/or prevents switching of the endogenous antibody from a membrane-associated form to a secreted form.

Embodiment 4. An engineered B cell comprising one or more nucleic acid molecules comprising one or more coding sequences encoding an exogenous protein, wherein at least one of the one or more nucleic acid molecules is integrated into or replaces all or a portion of a heavy chain immunoglobulin locus or a light chain immunoglobulin locus of the B cell.

Embodiment 5. An engineered B cell comprising one or more nucleic acid molecules comprising one or more coding sequences encoding an exogenous protein, wherein the engineered B cell comprises one or more modifications resulting in a greater capacity for the engineered B cell to produce and/or secrete the exogenous protein.

Embodiment 6. An engineered B cell comprising:
one or more nucleic acid molecules comprising one or more coding sequences encoding an exogenous protein; and
a chimeric receptor comprising a ligand binding domain, wherein, upon ligand binding, the receptor is capable of inducing (i) a mitogenic or proliferative signal; and/or (ii) a signal that is capable of modulating the differentiation of the engineered B cell.

Embodiment 7. An engineered B cell comprising:
one or more nucleic acid molecules comprising one or more coding sequences encoding an exogenous protein; and
a recombinant receptor comprising a ligand binding domain, wherein, upon ligand binding, the receptor is capable of inducing (i) a mitogenic or proliferative signal; and/or (ii) a signal that is capable of modulating the differentiation of the engineered B cell,
wherein the exogenous protein does not bind to the target of the ligand binding domain of the receptor and/or the exogenous protein does not contain a ligand binding site contained in the ligand binding domain of the receptor.

Embodiment 8. The engineered B cell of any one of embodiments 1-7, wherein the exogenous protein is secreted by the B cell or is capable of being secreted by the B cell.

Embodiment 9. The engineered B cell of embodiment 8, wherein the one or more coding sequences comprises a nucleotide sequence encoding a secretory signal peptide.

Embodiment 10. The engineered B cell of embodiment 9, wherein the secretory signal peptide comprises an amino acid sequence selected from among SEQ ID NOs: 76-202.

Embodiment 11. The engineered B cell of any one of embodiments 1-10, wherein the exogenous protein is a dimer.

Embodiment 12. The engineered B cell of embodiment 11, wherein the one or more nucleic acid molecules comprises a single nucleic acid molecule comprising a first coding sequence encoding a first domain or subunit of the dimer and a second coding sequence encoding a second domain or subunit of the dimer.

Embodiment 13. The engineered B cell of any one of embodiments 1-12, wherein the exogenous protein is a therapeutic protein.

Embodiment 14. The engineered B cell of any one of embodiments 1-13, wherein the exogenous protein binds to a target molecule associated with a disease or condition, wherein the molecule is optionally a protein, wherein the molecule or protein is expressed on the surface of a cell.

Embodiment 15. The engineered B cell of embodiment 14, wherein the disease or condition is selected from among a tumor or cancer, an autoimmune disease, an infectious disease or condition, and an inflammatory disease.

Embodiment 16. The engineered B cell of embodiment 15, wherein the disease or condition is a tumor or cancer.

Embodiment 17. The engineered B cell of any one of embodiments 1-16, wherein the exogenous protein binds to a molecule selected from ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1) or cyclin A1 (CCNA1)XX.

Embodiment 18. The engineered B cell of any one of embodiments 1-17, wherein the exogenous protein is selected from blood factors, thrombolytic agents, hormones, growth factors, cytokines, and antibodies or antigen-binding fragments thereof.

Embodiment 19. The engineered B cell of embodiment 18, wherein the cytokines are selected from among chemokines, interferons, interleukins, lymphokines, and tumor necrosis factors.

Embodiment 20. The engineered B cell of any one of embodiments 2-18, wherein the exogenous protein is an antibody or antigen-binding fragment thereof.

Embodiment 21. The engineered B cell of embodiment 20, wherein the antibody or antigen-binding fragment thereof binds to a cancer-associated antigen.

Embodiment 22. The engineered B cell of embodiment 20, wherein the antibody or antigen-binding fragment thereof binds to a pathogen-associated antigen.

Embodiment 23. The engineered B cell of embodiment 22, wherein the antibody or antigen-binding fragment thereof binds to a viral antigen.

Embodiment 24. The engineered B cell of embodiment 23, wherein the antibody or antigen-binding fragment thereof is a broadly neutralizing antiviral antibody or antigen-binding fragment thereof.

Embodiment 25. The engineered B cell of embodiment 24, wherein the antibody or antigen-binding fragment thereof is a broadly neutralizing anti-HIV antibody or antigen-binding fragment thereof.

Embodiment 26. The engineered B cell of embodiment 19, wherein the antibody is derived from alemtuzumab, atezolizumab, basiliximab, bevacizumab (Avastin®), blinatumomab, brentuximab vedotin, catumaxomab, cetuximab, daclizumab (Zenapax), daratumumab, denosumab, dinutuximab, elotuzumab, gemtuzumab (Mylotarg), ibritumomab tiuxetan (Zevalin), ipilimumab, necitumumab, nimotuzumab, nivolumab, obinutuzumab, ofatumumab, panitumumab, pembrolizumab, pertuzumab, pidilizumab (CT-011), ramucirumab, rituximab (Rituxan, Mabthera), siltuximab, tositumomab (Bexxar®), trastuzumab, ado-trastuzumab emtansine, zalutumumab, CEA-scan Fab fragment, OC125 monoclonal antibody, ab75705, B72.3, MPDL3280A, MSB001078C, or MEDI4736, or is an antigen-binding fragment thereof.

Embodiment 27. The engineered B cell of any one of embodiments 20-26, wherein the one or more nucleic acid molecules encodes the heavy and/or light chain of the antibody or antigen-binding fragment thereof.

Embodiment 28. The engineered B cell of embodiment 27, wherein the one or more nucleic acid molecules comprises a single nucleic acid molecule comprising a first coding sequence encoding the heavy chain and a second coding sequence encoding the light chain of the antibody or antigen-binding fragment thereof.

Embodiment 29. The engineered B cell of embodiment 12 or 28, wherein the first and second coding sequence are separated by an internal ribosome entry site (IRES), or a nucleotide sequence encoding a self-cleaving peptide or a peptide that causes ribosome skipping, which optionally is T2A, P2A, E2A, or F2A.

Embodiment 30. The engineered B cell of any one of embodiments 20-29, wherein the antibody or antigen-binding fragment thereof comprises one or more modifications in the heavy chain and/or light chain such that when the exogenous antibody or antigen-binding fragment is expressed in a cell, the frequency of mispairing with a heavy chain and/or light chain of an endogenous antibody is reduced.

Embodiment 31. The engineered B cell of embodiment 30, wherein the one or more modifications are in the CH2 and/or CH3 region of the constant chain.

Embodiment 32. The engineered B cell of embodiment 31, wherein the one or more modifications comprise a knob-into-hole (KiH) modification or a dock and lock (DNL) modification.

Embodiment 33. The engineered B cell of any one of embodiments 20-32, wherein the antibody or antigen-binding fragment thereof is a full-length antibody.

Embodiment 34. The engineered B cell of any one of embodiments 20-28, wherein the antibody or antigen-binding fragment thereof is a single chain antibody fragment.

Embodiment 35. The engineered B cell of embodiment 34, wherein the antibody or antigen-binding fragment thereof is an scFv.

Embodiment 36. The engineered B cell of any one of embodiments 1-35, wherein the one or more coding sequences encoding the exogenous protein do not comprise intronic sequences.

Embodiment 37. The engineered B cell of any one of embodiments 1-36, wherein the engineered B cell is a primary B cell.

Embodiment 38. The engineered B cell of any one of embodiments 1-37, wherein the engineered B cell is a B cell capable of differentiating into one or more of a plasmablast, a plasma cell, and a memory B cell.

Embodiment 39. The engineered B cell of any one of embodiments 1-38, wherein the engineered B cell is a naïve mature B cell.

Embodiment 40. The engineered B cell of any one of embodiments 1-39, wherein the engineered B cell comprises: one or more (such as all) phenotypic markers selected from $PAX5^+$, $BACH2^+$, $BCL-2^+$, $OBF1^+$, $OCT2^+$, $PU.1^+$, $SPIB^+$, $ETS1^+$, $IRF8^+$, $IRF4^{low}$, $BUMP1^-$, or $XBP1^-$; and/or one or more (such as all) cell surface markers selected from $CD19^+$, $CD20^+$, $CD21^+$, $CD22^+$, $CD23^+$, $CD24^+$, $CD10^-$, $CD27^-$, or $CD38^{low}$.

Embodiment 41. The engineered B cell of any one of embodiments 1-37, wherein the engineered B cell is a plasmablast, a plasma cell, or a memory B cell.

Embodiment 42. The engineered B cell of any one of embodiments 1-37, wherein the engineered B cell comprises one or more (such as all) phenotypic markers selected from $PAX5^-$, $BACH2^-$, $BCL-2^-$, $OBF1^-$, $OCT2^-$, $PU.1^-$, $SPIB^-$, $ETS1^-$, $IRF8^-$, $IRF4^{hi}$, $BLIMP1^{mid}$, or $XBP1^+$; and/or one or more (such as all) cell surface markers selected from $CD19^+$, $CD38^{high}$, $CD27^{high}$, $CD269^+$, $CD20^-$, or $CD138^-$.

Embodiment 43. The engineered B cell of any one of embodiments 1-37, wherein the engineered B cell comprises one or more (such as all) phenotypic markers selected from $PAX5^-$, $BACH2^-$, $BCL-2^-$, $OBF1^-$, $OCT2^-$, $PU.1^-$, $SPIB^-$, $ETS1^-$, $IRF8^-$, $IRF4^{hi}$, $BLIMP1^{hi}$, or $XBP1^+$; and/or one or more (such as all) cell surface markers selected from $CXCR4^+$, $CD27^+$, $CD38^{high}$, $CD138^+$, $CD269^+$, $CD19^{low}$, $CD20^-$, or $MHCII^{-/low}$.

Embodiment 44. The engineered B cell of any one of embodiments 1-37, wherein the engineered B cell comprises one or more (such as all) phenotypic markers selected from $PAX5^+$, $BACH2^+$, $BCL-2^+$, $OBF1^+$, $OCT2^+$, $PU.1^+$, $SPIB^+$, $ETS1^+$, $IRF8^+$, $IRF4^{low}$, $BLIMP1^-$, or $XBP1^-$; and/or one or more (such as all) cell surface markers selected from CD19$^+$, CD20$^+$, CD40$^+$, CD27$^{var}$, CXCR4,5,7$^+$, CD23$^{low}$, or CD38$^-$.

Embodiment 45. The engineered B cell of any one of embodiments 1-4 and 6-44, wherein the engineered B cell comprises one or more modifications resulting in a greater capacity for the engineered B cell to produce and/or secrete the exogenous protein.

Embodiment 46. The engineered B cell of embodiment 5 or 45, wherein the one or more modifications comprise altered expression of a protein involved in B cell lineage determination.

Embodiment 47. The engineered B cell of embodiment 46, wherein the one or more modifications comprise: reduced or eliminated expression of one or more proteins selected from PAX5, BACH2, BCL-6, OBF1, OCT2, PU.1, SPIB, ETS1, or IRF8, and/or increased expression of one or more proteins selected from IRF4, BLIMP1, or XBP1.

Embodiment 48. The engineered B cell of embodiment 46 or 47, wherein the altered expression is conditional.

Embodiment 49. The engineered B cell of embodiment 46 or 47, wherein the altered expression is inducible.

Embodiment 50. The engineered B cell of any one of embodiments 1 and 3-49, wherein the one or more nucleic acid molecules further comprises at least one promoter operably linked to one of the one or more coding sequences.

Embodiment 51. The engineered B cell of embodiment 50, wherein the promoter is a B cell promoter.

Embodiment 52. The engineered B cell of embodiment 51, wherein the promoter is a plasma cell promoter.

Embodiment 53. The engineered B cell of embodiment 51, wherein the promoter is an immunoglobulin (Ig) promoter.

Embodiment 54. The engineered B cell of embodiment 53, wherein the promoter is an immunoglobulin heavy chain promoter, a kappa light chain promoter, or a lambda light chain promoter.

Embodiment 55. The engineered B cell of embodiment 50, wherein the promoter is a constitutively active promoter.

Embodiment 56. The engineered B cell of embodiment 55, wherein the promoter is selected from SV40, CMV, UBC, EF1A, PGK or CAGG.

Embodiment 57. The engineered B cell of embodiment 50, wherein expression of the exogenous protein is conditional.

Embodiment 58. The engineered B cell of embodiment 2 or 50, wherein at least one of the one or more coding sequences is operably linked to a conditional promoter, enhancer, or transactivator.

Embodiment 59. The engineered B cell of embodiment 58, wherein the conditional promoter, enhancer, or transactivator is an inducible promoter, enhancer, or transactivator or a repressible promoter, enhancer, or transactivator.

Embodiment 60. The engineered B cell of embodiment 59, wherein the at least one of the one or more coding sequences is operably linked to a conditional promoter that is an inducible promoter.

Embodiment 61. The engineered B cell of embodiment 60, wherein the conditional promoter is not an immunoglobulin promoter.

Embodiment 62. The engineered B cell of embodiment 61, wherein the promoter comprises a Lac operator sequence, a tetracycline operator sequence, a galactose operator sequence or a doxycycline operator sequence, or is an analog thereof.

Embodiment 63. The engineered B cell of any one of embodiments 1-3, and 5-62, wherein at least one of the one or more nucleic acid molecules is integrated into or replaces all or a portion of a heavy chain immunoglobulin locus or a light chain immunoglobulin locus of the B cell.

Embodiment 64. The engineered B cell of embodiment 4 or 63, wherein the at least one of the one or more nucleic acid molecules comprises one or more coding sequences operably linked to an endogenous immunoglobulin promoter selected from an immunoglobulin heavy chain promoter, a kappa light chain promoter, or a lambda light chain promoter.

Embodiment 65. The engineered B cell of embodiment 64, wherein the one or more coding sequences are operably linked to an endogenous Ig enhancer.

Embodiment 66. The engineered B cell of any one of embodiments 4 and 63-65, wherein the one or more nucleic acid molecules comprises one or more coding sequences in-frame with an adjacent remaining coding sequence of the immunoglobulin locus.

Embodiment 67. The engineered B cell of any one of embodiments 4 and 63-66, wherein the exogenous protein is an antibody comprising a first polypeptide comprising a heavy chain sequence and a second polypeptide comprising a light chain sequence, and wherein the one or more coding sequences comprises a first coding sequence encoding the first polypeptide and a second coding sequence encoding the second polypeptide.

Embodiment 68. The engineered B cell of embodiment 67, wherein the first coding sequence is integrated into or replaces all or a portion of an endogenous immunoglobulin heavy chain locus and/or the second coding sequence is integrated into or replaces all or a portion of an endogenous immunoglobulin light chain locus, such that the engineered B cell is capable of expressing the first and second polypeptides.

Embodiment 69. The engineered B cell of embodiment 68, wherein the first coding sequence is operably linked to a promoter and/or enhancer associated with the endogenous immunoglobulin heavy chain locus and/or the second coding sequence is operably linked to a promoter and/or enhancer associated with the endogenous immunoglobulin light chain locus.

Embodiment 70. The engineered B cell of embodiment 67, wherein the first and second coding sequences are linked by a linker sequence, such that the engineered B cell is capable of expressing the first and second polypeptides.

Embodiment 71. The engineered B cell of embodiment 70, wherein the first and second coding sequences are integrated into or replace all or a portion of an endogenous immunoglobulin heavy chain or light chain locus.

Embodiment 72. The engineered B cell of embodiment 70 or 71, wherein the linker sequence is or comprises an internal ribosome entry site (IRES), or encodes a self-cleaving peptide or a peptide that causes ribosome skipping, which optionally is T2A, P2A, E2A, or F2A.

Embodiment 73. The engineered B cell of any one of embodiments 4 and 63-66, wherein the exogenous protein is a single chain antibody fragment comprising a heavy chain sequence and a light chain sequence, and wherein the one or more coding sequences comprises a coding sequence encoding the single chain antibody fragment.

Embodiment 74. The engineered B cell of embodiment 73, wherein the coding sequence is integrated into or replace all or a portion of an endogenous immunoglobulin heavy chain or light chain locus, such that the engineered B cell is capable of expressing the single chain antibody fragment.

Embodiment 75. The engineered B cell of embodiment 73 or 74, wherein the single chain antibody fragment is an scFv.

Embodiment 76. The engineered B cell of any one of embodiments 1-75, wherein the engineered B cell expresses an endogenous B cell receptor.

Embodiment 77. The engineered B cell of embodiment 76, wherein the endogenous B cell receptor is specific for a ligand present in a vaccine.

Embodiment 78. The engineered B cell of embodiment 77, wherein the vaccine is selected from among a diphtheria, tetanus, and/or pertussis vaccine, an influenza vaccine, a measles, mumps, rubella, and/or varicella vaccine, a hepatitis vaccine, a polio vaccine, a rabies vaccine, a shingles vaccine, a smallpox vaccine, a typhoid vaccine, and a yellow fever vaccine.

Embodiment 79. The engineered B cell of any one of embodiments 1-77, wherein the B cell comprises an agent or genetic disruption that reduces or eliminates expression of an endogenous immunoglobulin heavy and/or light chain product.

Embodiment 80. The engineered B cell of embodiment 79, wherein the genetic disruption comprises a disruption in the gene encoding the endogenous immunoglobulin heavy and/or light chain product.

Embodiment 81. The engineered B cell of embodiment 80, wherein the genetic disruption is biallelic.

Embodiment 82. The engineered B cell of any one of embodiments79-81, wherein the expression of the endogenous immunoglobulin heavy and/or light chain product is reduced by at least 50, 60, 70, 80, 90, or 95% as compared to the expression in the B cell in the absence of the agent or genetic disruption.

Embodiment 83. The engineered B cell of any one of embodiments 79-82, wherein the endogenous immunoglobulin heavy and/or light chain product is not expressed.

Embodiment 84. The engineered B cell of any one of embodiments 1-83, wherein the one or more nucleic acid molecules is codon-optimized.

Embodiment 85. The engineered B cell of any one of embodiments 1-5 and 8-84, wherein the engineered B cell expresses a recombinant receptor comprising a ligand binding domain, which, upon ligand binding, is capable of inducing (i) a mitogenic or proliferative signal; and/or (ii) a signal that is capable of modulating the differentiation of the engineered B cell.

Embodiment 86. The engineered B cell of embodiment 6, 7 or 85, wherein the receptor is a chimeric receptor comprising an ITAM-containing intracellular signaling domain.

Embodiment 87. The engineered B cell of embodiment 86, wherein the signaling domain is separated from the ligand-binding domain by a transmembrane domain, and optionally one or more spacers or linkers.

Embodiment 88. The engineered B cell of embodiment 7 or 85, wherein the receptor is contained in a complex comprising an endogenous protein comprising an ITAM-containing intracellular signaling domain.

Embodiment 89. The engineered B cell of any one of embodiments 86-88, wherein the ITAM-containing intracellular signaling domain comprises an intracellular signaling domain derived from CD79A, CD79B, CD3ζFcRγ, FcRβ, CD3γ, CD3δ, CD3ε, CD5, CD22, CD79a, CD79b, or CD66d.

Embodiment 90. The engineered B cell of any one of embodiments 86-89, wherein, upon ligand binding, the receptor signals via the ITAM-containing intracellular signaling domain.

Embodiment 91. The engineered B cell of any one of embodiments 6, 7, and 85-90, wherein the ligand-binding domain comprises an antibody moiety.

Embodiment 92. The engineered B cell of embodiment 91, wherein the antibody moiety is or comprises a full length antibody or an antigen-binding fragment thereof.

Embodiment 93. The engineered B cell of any one of embodiments 6, 7, and 85-92, wherein the receptor comprises a transmembrane domain derived from a B cell receptor, the α, β, δ, or γ chain of the T-cell receptor, CD28, CD3ε, CD3ζ, CD45, CD4, CD5, CD8, CD9, CD16, CD22, CD33, CD37, CD64, CD80, CD86, CD134, CD137, or CD154.

Embodiment 94. The engineered B cell of any one of embodiments 6 and 85-87, wherein the exogenous protein is an antibody or antigen-binding fragment and the ligand-binding domain of the receptor comprises the same heavy and/or light chain as the exogenous protein.

Embodiment 95. The engineered B cell of any of embodiments 85 and 88, wherein the receptor is a membrane-anchored form of the exogenous protein.

Embodiment 96. The engineered B cell of any of one of embodiments 6, 7 and 85-95, wherein the receptor is encoded by a nucleic acid sequence that does not comprise intronic sequences.

Embodiment 97. The engineered B cell of any one of embodiments 6 and 85-93, wherein the exogenous protein and the receptor recognize the same target antigen and/or the ligand binding domain and the exogenous protein contain the same ligand binding sites.

Embodiment 98. The engineered B cell of any one of embodiments 6 and 85-93, wherein the exogenous protein and the receptor bind to different ligands and/or have different ligand binding sites.

Embodiment 99. The engineered B cell of any one of embodiments 6, 7, and 85-98, wherein the ligand-binding domain of the receptor binds a ligand associated with a disease or condition.

Embodiment 100. The engineered B cell of embodiment 99, wherein the ligand-binding domain of the receptor binds a ligand present in a tumor environment in the subject.

Embodiment 101. The engineered B cell of embodiment 99, wherein the ligand-binding domain of the receptor binds a virally associated ligand.

Embodiment 102. The engineered B cell of any one of embodiments 6, 7 and 85-93, wherein the ligand-binding domain of the receptor binds an environmental ligand in a subject selected from among ligands that are not overexpressed on a disease cell in the subject, ligands that exhibit widespread tissue or cell expression in the subject, ligands that are ubiquitously expressed in the subject, ligands that are systemically expressed in the subject, ligands that are not tissue specific in the subject, and ligands exogenous to the subject.

Embodiment 103. The engineered B cell of any one of embodiments 6, 7, and 85-102, wherein the one or more nucleic acid molecules further encodes the receptor.

Embodiment 104. The engineered B cell of embodiment 103, wherein the one or more nucleic acid molecules comprises a linker sequence separating the sequence of nucleotides encoding the exogenous protein and the sequence of nucleotides encoding the receptor.

Embodiment 105. The engineered B cell of embodiment 104, wherein the linker sequence is or comprises an internal ribosome entry site (IRES), or encodes a self-cleaving peptide or a peptide that causes ribosome skipping, which optionally is T2A, P2A, E2A, or F2A.

Embodiment 106. The engineered B cell of any one of embodiments 1-2 and 4-105, wherein the engineered B cell expresses an endogenous antibody and comprises a modification that prevents class-switching of the endogenous antibody and/or prevents switching of the endogenous antibody from a membrane-associated form to a secreted form.

Embodiment 107. The engineered B cell of embodiment 3 or 106, wherein the modification that prevents class-switching comprises: reduced or eliminated expression of activation-induced deaminase (AID), uracil DNA glycosylase, and/or apyrimidic/apurinic (AP)-endonucleases; and/or mutation of one or more switch regions in the endogenous antibody locus.

Embodiment 108. The engineered B cell of any one of embodiments 3, 106, and 107, wherein the modification that prevents switching of an endogenous antibody expressed in the engineered B cell from a membrane-associated form to a secreted form comprises mutation of the polyadenylation signal upstream of the M1 exon at the endogenous antibody locus.

Embodiment 109. The engineered B cell of any one of embodiments 3 and 106-108, wherein the endogenous antibody is an IgM or IgD.

Embodiment 110. The engineered B cell of any one of embodiments 1-109, wherein the one or more coding sequences does not contain a nucleotide sequence encoding a transmembrane domain or the exogenous protein is not expressed on the cell surface or is not capable of being expressed on the cell surface.

Embodiment 111. The engineered B cell of any one of embodiments 6, 7, and 85-105, wherein the exogenous protein is secreted from the cell or is capable of being secreted from the cell upon ligand binding.

Embodiment 112. The engineered B cell of any one of embodiments 1-111, wherein the B cell is a human B cell.

Embodiment 113. The engineered B cell of any one of embodiments 1-112 that is a primary cell obtained from a patient.

Embodiment 114. The engineered B cell of any one of embodiments 1-113, wherein the cells are in a container or are in a formulation.

Embodiment 115. A nucleic acid molecule, comprising one or more coding sequences encoding a therapeutic protein and a receptor, wherein the receptor comprises a ligand binding domain, and wherein upon ligand binding, the receptor is capable of inducing (i) a mitogenic or proliferative signal; and/or (ii) a signal that is capable of modulating the differentiation of a B cell.

Embodiment 116. The nucleic acid molecule of embodiment 115, further comprising at least one promoter that is operatively linked to control expression of the therapeutic protein and/or the receptor.

Embodiment 117. The nucleic acid molecule of embodiment 115 or embodiment 116, wherein the sequence of nucleotides encoding the therapeutic protein is operatively linked to a first promoter and the sequence of nucleotides encoding the receptor is operatively linked to a second promoter, which first and second promoter can be the same or different.

Embodiment 118. The nucleic acid molecule of any of embodiments 115-117, wherein the nucleic acid molecule comprises a linker sequence separating the sequence of nucleotides encoding the therapeutic protein and the sequence of nucleotides encoding the receptor.

Embodiment 119. The nucleic acid molecule of embodiment 118, wherein the linker sequence is or comprises an internal ribosome entry site (IRES), or encodes a self-cleaving peptide or a peptide that causes ribosome skipping, optionally a T2A, P2A, E2A, or F2A.

Embodiment 120. A vector, comprising the nucleic acid molecule of any one of embodiments 115-119.

Embodiment 121. The vector of embodiment 120 that is a viral vector.

Embodiment 122. The vector of embodiment 120 or embodiment 121 that is a retroviral vector.

Embodiment 123. The vector of any one of embodiments 120-122 that is a lentiviral vector or a gammaretroviral vector.

Embodiment 124. An engineered B cell, comprising the nucleic acid molecule of any one of embodiments 92-96 or the vector of any one of embodiments 120-123.

Embodiment 125. A method of producing an engineered B cell, comprising introducing into a B cell or a B cell precursor the nucleic acid molecule of any of embodiments 115-119 or the vector of any one of embodiments 120-123.

Embodiment 126. A method of producing an engineered B cell, the method comprising introducing one or more nucleic acid molecules comprising one or more coding sequences encoding an exogenous protein under the control of one or more elements to effect secretion of the exogenous protein into a B cell or B cell precursor, wherein the exogenous protein is not an antibody.

Embodiment 127. A method of producing an engineered B cell, the method comprising introducing one or more nucleic acid molecules comprising one or more coding sequences encoding an exogenous protein into a B cell or B cell precursor, wherein expression of the exogenous protein in the engineered B cell is conditional.

Embodiment 128. A method of producing an engineered B cell, the method comprising introducing one or more nucleic acid molecules comprising one or more coding sequences encoding an exogenous protein into a B cell or B cell precursor, wherein the engineered B cell (1) expresses an endogenous antibody and (2) comprises a modification that prevents class-switching of the endogenous antibody and/or prevents switching of the endogenous antibody from a membrane-associated form to a secreted form.

Embodiment 129. A method of producing an engineered B cell, the method comprising introducing one or more nucleic acid molecules comprising one or more coding sequences encoding an exogenous protein into a B cell or B cell precursor, wherein at least one of the one or more nucleic acid molecules is integrated into a target locus selected from a heavy chain immunoglobulin locus or a light chain immunoglobulin locus by insertion into the target locus or replacement of all or a portion of the target locus.

Embodiment 130. A method of producing an engineered B cell, the method comprising introducing one or more nucleic acid molecules comprising one or more coding sequences encoding an exogenous protein into a B cell or B cell precursor, wherein the engineered B cell comprises one or more modifications resulting in a greater capacity for the engineered B cell to produce and/or secrete the exogenous protein.

Embodiment 131. A method of producing an engineered B cell, the method comprising introducing one or more nucleic acid molecules comprising one or more coding sequences encoding an exogenous protein into a B cell or B cell precursor, wherein the B cell comprises a chimeric receptor comprising a ligand binding domain, wherein, upon ligand binding, the receptor is capable of inducing (i) a mitogenic or proliferative signal; and/or (ii) a signal that is capable of modulating the differentiation of the engineered B cell.

Embodiment 132. A method of producing an engineered B cell, the method comprising introducing one or more nucleic acid molecules comprising one or more coding sequences encoding an exogenous protein into a B cell or B cell precursor, wherein the B cell comprises a recombinant receptor comprising a ligand binding domain, wherein, upon ligand binding, the receptor is capable of inducing (i) a mitogenic or proliferative signal; and/or (ii) a signal that is capable of modulating the differentiation of the engineered B cell, and wherein the exogenous protein does not bind to the target of the ligand binding domain of the receptor and/or the exogenous protein does not contain a ligand binding site contained in the ligand binding domain of the receptor.

Embodiment 133. The method of any one of embodiments 125-132, wherein the exogenous protein is secreted by the engineered B cell or is capable of being secreted by the engineered B cell.

Embodiment 134. The method of embodiment 133, wherein the one or more coding sequences comprises a nucleotide sequence encoding a secretory signal peptide.

Embodiment 135. The method of embodiment 134, wherein the secretory signal peptide comprises and amino acid selected from among SEQ ID NOs: 76-202.

Embodiment 136. The method of any one of embodiments 125-135, wherein the exogenous protein is a dimer.

Embodiment 137. The method of embodiment 136, wherein the one or more nucleic acid molecules comprises a single nucleic acid molecule comprising a first coding sequence encoding a first domain or subunit and a second coding sequence encoding a second domain or subunit of the dimer.

Embodiment 138. The method of any one of embodiments 125-137, wherein the exogenous protein is a therapeutic protein.

Embodiment 139. The method of any one of embodiments 125-138, wherein the exogenous protein binds to a target molecule associated with a disease or condition, wherein the molecule is optionally a protein, wherein the molecule or protein is expressed on the surface of a cell.

Embodiment 140. The method of embodiment 139, wherein the disease or condition is selected from among a tumor or cancer, an autoimmune disease, an infectious disease or condition, an inflammatory disease.

Embodiment 141. The method of embodiment 140, wherein the disease or condition is a tumor or cancer.

Embodiment 142. The method of any one of embodiments 125-141, wherein the exogenous protein binds to a molecule selected from ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1) or cyclin A1 (CCNA1)XX.

Embodiment 143. The method of any one of embodiments 125-142, wherein the exogenous protein is selected from blood factors, thrombolytic agents, hormones, growth factors, cytokines (including chemokines, interferons, interleukins, lymphokines, and tumor necrosis factors), and antibodies or antigen-binding fragments thereof.

Embodiment 144. The method of any one of embodiments 127-143, wherein the exogenous protein is an antibody or antigen-binding fragment thereof.

Embodiment 145. The method of embodiment 144, wherein the antibody or antigen-binding fragment thereof binds to a cancer-associated antigen.

Embodiment 146. The method of embodiment 144, wherein the antibody or antigen-binding fragment thereof binds to a pathogen-associated antigen.

Embodiment 147. The method of embodiment 146, wherein the antibody or antigen-binding fragment thereof binds to a viral antigen.

Embodiment 148. The method of embodiment 147, wherein the antibody or antigen-binding fragment thereof is a broadly neutralizing antiviral antibody or antigen-binding fragment thereof.

Embodiment 149. The method of embodiment 148, wherein the antibody or antigen-binding fragment thereof is a broadly neutralizing anti-HIV antibody or antigen-binding fragment thereof.

Embodiment 150. The method of embodiment 144, wherein the antibody is derived from alemtuzumab, atezolizumab, basiliximab, bevacizumab (Avastin®), blinatumomab, brentuximab vedotin, catumaxomab, cetuximab, daclizumab (Zenapax), daratumumab, denosumab, dinutuximab, elotuzumab, gemtuzumab (Mylotarg), ibritumomab tiuxetan (Zevalin), ipilimumab, necitumumab, nimotuzumab, nivolumab, obinutuzumab, ofatumumab, panitumumab, pembrolizumab, pertuzumab, pidilizumab (CT-011), ramucirumab, rituximab (Rituxan, Mabthera), siltuximab, tositumomab (Bexxar®), trastuzumab, ado-trastuzumab emtansine, zalutumumab, CEA-scan Fab fragment, OC125 monoclonal antibody, ab75705, B72.3, MPDL3280A, MSB001078C, or MEDI4736, or is an antigen-binding fragment thereof.

Embodiment 151. The method of any one of embodiments 144-150, wherein the one or more nucleic acid molecules encodes the heavy and/or light chain of the antibody or antigen-binding fragment thereof.

Embodiment 152. The method of embodiment 151, wherein the one or more nucleic acid molecules comprises a single nucleic acid molecule comprising a first coding sequence encoding the heavy chain and a second coding sequence encoding the light chain of the antibody or antigen-binding fragment thereof.

Embodiment 153. The method of embodiment 137 or 152, wherein the first and second coding sequence are separated by an internal ribosome entry site (IRES), or a sequence encoding a self-cleaving peptide or a peptide that causes ribosome skipping, which optionally is T2A, P2A, E2A, or F2A.

Embodiment 154. The method of any one of embodiments 144-153, wherein the antibody or antigen-binding fragment thereof comprises one or more modifications in the heavy chain and/or light chain such that when the exogenous antibody or antigen-binding fragment is expressed in the cell, the frequency of mispairing with a heavy chain and/or light chain of an endogenous antibody is reduced.

Embodiment 155. The method of embodiment 154, wherein the one or more modifications are in the CH2 and/or CH3 region of the constant chain.

Embodiment 156. The method of embodiment 155, wherein the one or more modifications comprise a knob-into-hole (KiH) modification or a dock and lock (DNL) modification.

Embodiment 157. The method of any one of embodiments 144-156, wherein the antibody or antigen-binding fragment thereof is a full-length antibody.

Embodiment 158. The method of any one of embodiments 144-152, wherein the antibody or antigen-binding fragment thereof is a single chain antibody fragment.

Embodiment 159. The method of embodiment 158, wherein the antibody or antigen-binding fragment thereof is an scFv.

Embodiment 160. The method of any one of embodiments 125-159, wherein the one or more coding sequences encoding the exogenous protein do not comprise intronic sequences.

Embodiment 161. The method of any one of embodiments 125-160, wherein the B cell or B cell precursor is a hematopoietic stem cell (HSC) or a primary B cell selected from a naïve mature B cell, a plasmablast, a plasma cell, or a memory B cell.

Embodiment 162. The method of any one of embodiments 125-161, wherein the engineered B cell is a B cell capable of differentiating into one or more cells selected from a plasmablast, a plasma cell, or a memory B cell.

Embodiment 163. The method of any one of embodiments 125-162, wherein the engineered B cell is a naïve mature B cell.

Embodiment 164. The method of any one of embodiments 125-163, wherein the engineered B cell comprises: one or more (such as all) phenotypic markers selected from $PAX5^+$, $BACH2^+$, $BCL-2^+$, $OBF1^+$, $OCT2^+$, $PU.1^+$, $SPIB^+$, $ETS1^+$, $IRF8^+$, $IRF4^{low}$, $BUMP1^-$, or $XBP1^-$; and/or
one or more (such as all) cell surface markers selected from $CD19^+$, $CD20^+$, $CD21^+$, $CD22^+$, $CD23^+$, $CD24^+$, $CD10^-$, $CD27^-$, or $CD38^{low}$.

Embodiment 165. The method of any one of embodiments 125-161, wherein the engineered B cell is a plasmablast, a plasma cell, or a memory B cell.

Embodiment 166. The method of any one of embodiments 125-161, wherein the engineered B cell comprises one or more (such as all) phenotypic markers selected from $PAX5^-$, $BACH2^-$, $BCL-2^-$, $OBF1^-$, $OCT2^-$, $PU.1^-$, $SPIB^-$, $ETS1^-$, $IRF8^-$, $IRF4^{hi}$, $BLIMP1^{mid}$, or $XBP1^+$; and/or one or more (such as all) cell surface markers selected from $CD19^+$, $CD38^{high}$, $CD27^{high}$, $CD269^+$, $MHCII^+$, $CD20^-$, or $CD138^-$.

Embodiment 167. The method of any one of embodiments 125-161, wherein the engineered B cell comprises one or more (such as all) phenotypic markers selected from $PAX5^-$, $BACH2^-$, $BCL-2^-$, $OBF1^-$, $OCT2^-$, $PU.1^-$, $SPIB^-$, $ETS1^-$, $IRF8^-$, $IRF4^{hi}$, $BLIMP1^{hi}$, or $XBP1^+$; and/or one or more (such as all) cell surface markers selected from $CXCR4^+$, $CD27^+$, $CD38^{high}$, $CD138^+$, $CD269^+$, $CD19^{low}$, $CD20^-$, or $MHCII^{-/low}$.

Embodiment 168. The method of any one of embodiments 125-161, wherein the engineered B cell comprises one or more (such as all) phenotypic markers selected from $PAX5^+$, $BACH2^+$, $BCL-2^+$, $OBF1^+$, $OCT2^+$, $PU.1^+$, $SPIB^+$, $ETS1^+$, $IRF8^+$, $IRF4^{low}$, $BLIMP1^-$, or $XBP1^-$; and/or one or more (such as all) cell surface markers selected from $CD19^+$, $CD20^+$, $CD40^+$, $CD27^{var}$, $CXCR4,5,7^+$, $CD23^{low}$, or $CD38^-$.

Embodiment 169. The method of any one of embodiments 125-168, further comprising contacting the B cell or B cell precursor with one or more agents that modulate B cell differentiation.

Embodiment 170. The method of embodiment 169, wherein the one or more agents are selected from IL-2, IL-3, IL-6, IL-10, SCF, G-CSF, CpG, CD40 ligand, Flt3 ligand, or thrombopoietin.

Embodiment 171. The method of embodiment 169 or 170, further comprising co-culturing the B cell or B cell precursor with cells that express one or more B cell lineage growth factors, optionally including IL-7 and CD40 ligand.

Embodiment 172. The method of any one of embodiments 125-129 and 131-171, wherein the engineered B cell comprises one or more modifications resulting in a greater capacity for the engineered B cell to produce and/or secrete the exogenous protein.

Embodiment 173. The method of embodiment 130 or 172, wherein the one or more modifications comprise altered expression of a protein involved in B cell lineage determination.

Embodiment 174. The method of embodiment 173, wherein the one or more modifications comprise: reduced or eliminated expression of one or more proteins selected from PAX5, BACH2, BCL-6, OBF1, OCT2, PU.1, SPIB, ETS1, or IRF8, and/or increased expression of one or more proteins selected from IRF4, BLIMP1, or XBP1.

Embodiment 175. The method of embodiment 173 or 174, wherein the altered expression is conditional.

Embodiment 176. The method of embodiment 173 or 174, wherein the altered expression is inducible.

Embodiment 177. The method of any one of embodiments 125, 126, and 128-176, wherein the one or more nucleic acid molecules further comprises at least one promoter operably linked to one of the one or more coding sequences.

Embodiment 178. The method of embodiment 177, wherein the promoter is a B cell promoter.

Embodiment 179. The method of embodiment 178, wherein the promoter is a plasma cell promoter.

Embodiment 180. The method of embodiment 178, wherein the promoter is an immunoglobulin (Ig) promoter.

Embodiment 181. The method of embodiment 180, wherein the promoter is an immunoglobulin heavy chain promoter, a kappa light chain promoter, or a lambda light chain promoter.

Embodiment 182. The method of embodiment 177, wherein the promoter is a constitutively active promoter.

Embodiment 183. The method of embodiment 182, wherein the promoter is selected from SV40, CMV, UBC, EF1A, PGK or CAGG.

Embodiment 184. The method of embodiment 177, wherein expression of the exogenous protein is conditional.

Embodiment 185. The method of embodiment 127 or 177, wherein at least one of the one or more coding sequences is operably linked to a conditional promoter, enhancer, or transactivator.

Embodiment 186. The method of embodiment 185, wherein the conditional promoter, enhancer, or transactivator is an inducible promoter, enhancer, or transactivator or a repressible promoter, enhancer, or transactivator.

Embodiment 187. The method of embodiment 186, wherein the at least one of the one or more coding sequences is operably linked to a conditional promoter that is an inducible promoter.

Embodiment 188. The method of embodiment 187, wherein the conditional promoter is not an immunoglobulin promoter.

Embodiment 189. The method of embodiment 188, wherein the promoter comprises a Lac operator sequence, a tetracycline operator sequence, a galactose operator sequence or a doxycycline operator sequence, or is an analog thereof.

Embodiment 190. The method of any one of embodiments 125-128, and 130-189, wherein at least one of the one or more nucleic acid molecules is integrated into a target locus by insertion into the target locus or replacement of all or a portion of the target locus.

Embodiment 191. The method of embodiment 190, wherein the target locus is a heavy chain immunoglobulin locus or a light chain immunoglobulin locus.

Embodiment 192. The method of embodiment 129 or 191, wherein one or more coding sequences contained in the at least one of the one or more nucleic acid molecules are operably linked to an endogenous immunoglobulin promoter selected from an immunoglobulin heavy chain promoter, a kappa light chain promoter, or a lambda light chain promoter.

Embodiment 193. The method of any one of embodiments 129, 191, and 192, wherein one or more coding sequences contained in the at least one of the one or more nucleic acid molecules are operably linked to an endogenous Ig enhancer.

Embodiment 194. The method of any one of embodiments 129 and 191-193, wherein one or more coding sequences contained in the at least one of the one or more nucleic acid molecules are in-frame with an adjacent remaining coding sequence of the immunoglobulin locus.

Embodiment 195. The method of any one of embodiments 129 and 191-194, wherein the exogenous protein is an antibody comprising a first polypeptide comprising a heavy chain sequence and a second polypeptide comprising a light chain sequence, and wherein the one or more coding sequences comprises a first coding sequence encoding the first polypeptide and a second coding sequence encoding the second polypeptide.

Embodiment 196. The method of embodiment 195, wherein the first coding sequence is integrated into or replaces all or a portion of an endogenous immunoglobulin heavy chain locus and/or the second coding sequence is integrated into or replaces all or a portion of an endogenous immunoglobulin light chain locus, such that the engineered B cell is capable of expressing the first and second polypeptides.

Embodiment 197. The method of embodiment 196, wherein the first coding sequence is operably linked to a promoter and/or enhancer associated with the endogenous immunoglobulin heavy chain locus and/or the second coding sequence is operably linked to a promoter and/or enhancer associated with the endogenous immunoglobulin light chain locus.

Embodiment 198. The method of embodiment 195, wherein the first and second coding sequences are linked by a linker sequence, such that the engineered B cell is capable of expressing the first and second polypeptides.

Embodiment 199. The method of embodiment 198, wherein the first and second coding sequences are integrated into or replace all or a portion of an endogenous immunoglobulin heavy chain or light chain locus.

Embodiment 200. The method of embodiment 198 or 199, wherein the linker sequence is or comprises an internal ribosome entry site (IRES), or encodes a self-cleaving peptide or a peptide that causes ribosome skipping, which optionally is T2A, P2A, E2A, or F2A.

Embodiment 201. The method of any one of embodiments 129 and 191-194, wherein the exogenous protein is a single chain antibody fragment comprising a heavy chain sequence and a light chain sequence, and wherein the one or more coding sequences comprises a coding sequence encoding the single chain antibody fragment.

Embodiment 202. The method of embodiment 201, wherein the coding sequence is integrated into or replace all or a portion of an endogenous immunoglobulin heavy chain or light chain locus, such that the engineered B cell is capable of expressing the single chain antibody fragment.

Embodiment 203. The method of embodiment 201 or 202, wherein the single chain antibody fragment is an scFv.

Embodiment 204. The method of any one of embodiments 125-203, wherein the engineered B cell receptor expresses an endogenous B cell receptor.

Embodiment 205. The method of embodiment 204, wherein the endogenous B cell receptor is specific for a ligand present in a vaccine.

Embodiment 206. The method of embodiment 205, wherein the vaccine is selected from among a diphtheria, tetanus, and/or pertussis vaccine, an influenza vaccine, a measles, mumps, rubella, and/or varicella vaccine, a hepatitis vaccine, a polio vaccine, a rabies vaccine, a shingles vaccine, a smallpox vaccine, a typhoid vaccine, and a yellow fever vaccine.

Embodiment 207. The method of any one of embodiments 129 and 190-206, wherein the at least one of the one or more nucleic acid molecules comprises sequences that allow for integration of the at least one of the one or more nucleic acid molecules into the B cell at the target locus by homologous recombination.

Embodiment 208. The method of embodiment 207, wherein the at least one of the one or more nucleic acid molecules comprises flanking sequences that are homologous to sequences at the target locus.

Embodiment 209. The method of any one of embodiments 129 and 190-208, wherein integration into the target locus of the at least one of the one or more nucleic acid molecules is mediated by a designer nuclease selected from zinc-finger nucleases (ZFNs), transcription activator-like effector nucleases (TALENs), or RNA-guided nucleases (RGNs).

Embodiment 210. The method of embodiment 209, wherein the RGN is a clustered, regularly interspaced, short palindromic repeats (CRISPR)-associated Cas9 (CRISPR-Cas9) nuclease.

Embodiment 211. The method of any one of embodiments 125-128, and 130-189, wherein at least one of the one or more nucleic acid molecules is inserted into a random locus.

Embodiment 212. The method of any one of embodiments 125-211, wherein the one or more nucleic acid molecules is introduced into the B cell by viral transduction, transposition, electroporation, or chemical transfection.

Embodiment 213. The method of embodiment 212, wherein the one or more nucleic acid molecules is introduced into the B cell by transduction with a retroviral vector comprising the one or more nucleic acid molecules.

Embodiment 214. The method of embodiment 212, wherein the one or more nucleic acid molecules is introduced into the B cell by transduction with a lentiviral vector comprising the one or more nucleic acid molecules.

Embodiment 215. The method of embodiment 212, wherein the one or more nucleic acid molecules is introduced into the B cell by transposition with a transposon comprising the one or more nucleic acid molecules.

Embodiment 216. The method of embodiment 212, wherein the one or more nucleic acid molecules is introduced into the B cell by electroporation or transfection of a vector comprising the one or more nucleic acid molecules.

Embodiment 217. The method of any one of embodiments 125-216, wherein the B cell comprises an agent or genetic disruption that reduces or eliminates expression of an endogenous immunoglobulin heavy and/or light chain product.

Embodiment 218. The method of embodiment 217, wherein the genetic disruption comprises a disruption in the gene encoding the endogenous immunoglobulin heavy and/or light chain product.

Embodiment 219. The method of embodiment 218, wherein the genetic disruption is biallelic.

Embodiment 220. The method of any one of embodiments 217-219, wherein the expression of the endogenous immunoglobulin heavy and/or light chain product is reduced by at least 50, 60, 70, 80, 90, or 95% as compared to the expression in the B cell in the absence of the agent or genetic disruption.

Embodiment 221. The method of any one of embodiments 217-220, wherein the endogenous immunoglobulin heavy and/or light chain product is not expressed.

Embodiment 222. The method of any one of embodiments 125-221, wherein the one or more nucleic acid molecules is codon-optimized.

Embodiment 223. The method of any one of embodiments 125-130 and 133-222, wherein the engineered B cell expresses a receptor comprising a ligand binding domain, which, upon ligand binding, is capable of inducing (i) a mitogenic or proliferative signal; and/or (ii) a signal that is capable of modulating the differentiation of the engineered B cell.

Embodiment 224. The method of embodiment 131, embodiment 132 or embodiment 223, wherein the one or more nucleic acid molecules is a first nucleic acid molecule and the method comprises administering a second nucleic acid molecule encoding the receptor into the B cell or B cell precursor.

Embodiment 225. The method of embodiment 131, embodiment 132 or embodiment 223, wherein the one or more nucleic acid molecules further comprises a sequence of nucleotides encoding the receptor.

Embodiment 226. The method of embodiment 225, wherein the one or more nucleic acid molecules comprises a linker sequence separating the sequence of nucleotides encoding the exogenous protein and the sequence of nucleotides encoding the receptor.

Embodiment 227. The method of embodiment 226, wherein the linker sequence is or comprises an internal ribosome entry site (IRES), or encodes a self-cleaving peptide or a peptide that causes ribosome skipping, which optionally is T2A, P2A, E2A, or F2A.

Embodiment 228. The method of embodiment 131, embodiment 132 or any of embodiments 223-227, wherein the receptor is a chimeric receptor comprising an ITAM-containing intracellular signaling domain.

Embodiment 229. The method of embodiment 228, wherein the signaling domain is separated from the ligand-binding domain by a transmembrane domain, and optionally one or more spacers or linkers.

Embodiment 230. The method of any of embodiments 132 or 223-227, wherein the receptor is contained in a complex comprising an endogenous protein comprising an ITAM-containing intracellular signaling domain.

Embodiment 231. The method of any one of embodiments 228-230, wherein the ITAM-containing intracellular signaling domain comprises an intracellular signaling domain derived from CD79A, CD79B, CD3ζ, FcRγ, FcRβ, CD3γ, CD3δ, CD3ε, CD5, CD22, CD79a, CD79b, or CD66d.

Embodiment 232. The method of any one of embodiments 228-231, wherein, upon ligand binding, the receptor signals via the ITAM-containing intracellular signaling domain.

Embodiment 233. The method of any one of embodiments 131, 132, and 223-232, wherein the ligand-binding domain comprises an antibody moiety.

Embodiment 234. The method of embodiment 233, wherein the antibody moiety is or comprises a full length antibody or an antigen-binding fragment thereof.

Embodiment 235. The method of any one of embodiments 131, 132, and 223-234, wherein the receptor comprises a transmembrane domain derived from a B cell receptor, the α, β, δ, or γ chain of the T-cell receptor, CD28, CD3ε, CD3ζ, CD45, CD4, CD5, CD8, CD9, CD16, CD22, CD33, CD37, CD64, CD80, CD86, CD134, CD137, or CD154.

Embodiment 236. The method of any one of embodiments 131 and 223-229, wherein the exogenous protein is an antibody or antigen-binding fragment and the ligand-binding domain of the receptor comprises the same heavy and/or light chain as the exogenous protein.

Embodiment 237. The method of embodiment 223, wherein the receptor is a membrane-anchored form of the exogenous protein.

Embodiment 238. The method of any of one of embodiments 131, 132 and 223-237, wherein the receptor is encoded by a nucleic acid sequence that does not comprise intronic sequences.

Embodiment 239. The method of any one of embodiments 131 and 223-235, wherein the exogenous protein and the receptor recognize the same target antigen and/or the ligand binding domain and the exogenous protein contain the same ligand binding sites.

Embodiment 240. The method of any one of embodiments 131 and 223-235, wherein the exogenous protein and the receptor bind to different ligands and/or having different ligand binding sites.

Embodiment 241. The method of any one of embodiments 131, 132, and 223-240, wherein the ligand-binding domain of the receptor binds a ligand associated with a disease or condition.

Embodiment 242. The method of embodiment 241, wherein the ligand-binding domain of the receptor binds a ligand present in a tumor environment in the subject.

Embodiment 243. The method of embodiment 241, wherein the ligand-binding domain of the receptor binds a virally associated ligand.

Embodiment 244. The method of embodiment 132 or 240, wherein the ligand-binding domain of the receptor binds an environmental ligand in a subject selected from among ligands that are not overexpressed on a disease cell in the subject, ligands that exhibit widespread tissue or cell expression in the subject, ligands that are ubiquitously expressed in the subject, ligands that are systemically expressed in the subject, ligands that are not tissue specific in the subject, and ligands exogenous to the subject.

Embodiment 245. The method of any one of embodiments 125-127 and 129-244, wherein the engineered B cell expresses an endogenous antibody and comprises a modification that prevents class-switching of the endogenous antibody and/or prevents switching of the endogenous antibody from a membrane-associated form to a secreted form.

Embodiment 246. The method of embodiment 128 or 245, wherein the modification that prevents class-switching comprises: reduced or eliminated expression of activation-induced deaminase (AID), uracil DNA glycosylase, and/or apyrimidic/apurinic (AP)-endonucleases; and/or mutation of one or more switch regions in the endogenous antibody locus.

Embodiment 247. The method of any one of embodiments 128, 245, and 246, wherein the modification that prevents switching of an endogenous antibody expressed in the engineered B cell from a membrane-associated form to a secreted form comprises mutation of the polyadenylation signal upstream of the M1 exon at the endogenous antibody locus.

Embodiment 248. The method of any one of embodiments 128 and 245-247, wherein the endogenous antibody is an IgM or IgD.

Embodiment 249. The method of any one of embodiments 125-248, wherein the one or more coding sequences does not contain a nucleotide sequence encoding a transmembrane domain or the exogenous protein is not expressed on the cell surface or is not capable of being expressed on the cell surface.

Embodiment 250. The method of any one of embodiments 131, 132, and 223-244, wherein the exogenous protein is secreted from the cell or is capable of being secreted from the cell upon ligand binding.

Embodiment 251. The method of any one of embodiments 125-250, wherein the B cell is a human B cell.

Embodiment 252. The method of any one of embodiments 125-251, wherein the B cell is a primary B cell obtained from a patient.

Embodiment 253. An engineered B cell prepared by the method of any of embodiments 125-252.

Embodiment 254. A pharmaceutical composition comprising the engineered B cell of any one of embodiments 1-114 and 124 or the engineered B cell of embodiment 253 and a pharmaceutically acceptable carrier.

Embodiment 255. An article of manufacture, comprising the cells of any one of embodiments 1-114, 124 and 253 or the pharmaceutical composition of embodiment 254.

Embodiment 256. The article of manufacture of embodiment 255 that is a container.

Embodiment 257. The article of manufacture of embodiment 256, wherein the container is a bag.

Embodiment 258. A method of treatment, comprising administering the engineered B cell of any one of embodiments 1-114 and 124, the engineered B cell of embodiment 253, or the pharmaceutical composition of embodiment 254 to a subject having a disease or condition.

Embodiment 259. The method of embodiment 258, wherein the exogenous protein is a therapeutic protein useful for treating the disease or condition.

Embodiment 260. The method of embodiment 259, wherein the therapeutic protein is selected from blood factors, thrombolytic agents, hormones, growth factors, cytokines (including chemokines, interferons, interleukins, lymphokines, and tumor necrosis factors), and antibodies or antigen-binding fragments thereof.

Embodiment 261. The method of embodiment 211, wherein the exogenous protein is an antibody or antigen-binding fragment thereof that specifically binds to a ligand or antigen associated with the disease or condition.

Embodiment 262. The method of embodiment 261, wherein the antibody or antigen-binding fragment thereof binds to a cancer-associated antigen.

Embodiment 263. The method of embodiment 261, wherein the antibody or antigen-binding fragment thereof binds to a pathogen-associated antigen.

Embodiment 264. The method of embodiment 263, wherein the antibody or antigen-binding fragment thereof binds to a viral antigen.

Embodiment 265. The method of embodiment 264, wherein the antibody or antigen-binding fragment thereof is a broadly neutralizing antiviral antibody or antigen-binding fragment thereof.

Embodiment 266. The method of embodiment 265, wherein the antibody or antigen-binding fragment thereof is a broadly neutralizing anti-HIV antibody or antigen-binding fragment thereof.

Embodiment 267. The method of any one of embodiments 258-266, wherein the engineered B cell is a naïve mature B cell or a memory B cell.

Embodiment 268. The method of embodiment 267, further comprising inducing the engineered B cell to increase production and/or secretion of the exogenous protein.

Embodiment 269. The method of embodiment 268, wherein the inducing comprises administering to the subject an agent that binds to the ligand binding domain of an endogenous B cell receptor expressed in the engineered B cell.

Embodiment 270. The method of embodiment 268, wherein the inducing comprises administering to the subject an agent that binds to the ligand binding domain of a recombinant or chimeric receptor expressed in the engineered B cell.

Embodiment 271. The method of any one of embodiments 268-270, wherein the engineered B cell is induced to differentiate into a plasmablast or a plasma cell.

Embodiment 272. The method of any one of embodiments 258-266, wherein the engineered B cell is a plasmablast or plasma cell.

Embodiment 273. The method of any one of embodiments 258-272, wherein the exogenous protein is under the control of an endogenous immunoglobulin promoter or a constitutively active promoter.

Embodiment 274. The method of any one of embodiments 258-272, wherein the exogenous protein is under the control of an inducible promoter, and the method further comprises administering to the subject an agent that activates the inducible promoter.

Embodiment 275. The method of any one of embodiments 258-274, wherein a therapeutic amount of the engineered B cell persists in the subject for at least about 1 month, at least 2 months, at least 6 months or at least a year following administration.

Embodiment 276. The method of any one of embodiments 258-275, wherein the treatment results in a duration of action of at least about 1 month, at least 2 months, at least 6 months or at least a year.

Embodiment 277. The method of any one of embodiments 258-276, wherein a single administration of the engineered B cell or composition results in an increased duration of action compared to the maximum tolerable duration of action resulting from a single direct administration of the exogenous protein.

Embodiment 278. The method of embodiment 277, wherein the increase is at least 1.2-fold, 1.5-fold, 2-fold, 3-fold, 4-fold, or 5-fold.

Embodiment 279. The method of any one of embodiments 258-278, wherein the disease or conditions is a cancer, a tumor, an autoimmune disease or disorder, or an infectious disease.

Embodiment 280. The method of any one of embodiments 258-279, wherein the engineered B cell is autologous to the subject.

Embodiment 281. The method of any one of embodiments 258-279, wherein the engineered B cell is allogeneic to the subject.

Embodiment 282. The method of any one of embodiments 258-281, wherein the subject is human.

Embodiment 283. The method of any one of embodiments 258-282, wherein the dose of cells administered is at least or at least about or is or is about $1\times10^5$ cells per kilogram body weight of the subject, is at least or at least about or is or is about $1\times10^7$ cells, and/or is at least or at least about or is or is about $1\times10^7$ cells/m² of the subject.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| # | SEQUENCE | ANNOTATION |
|---|----------|------------|
| 1 | EGRGSLLTCGDVEENPGP | T2A artificial |
| 2 | ATNFSLLKQAGDVEENPGP | P2A artificial |
| 3 | QCTNYALLKLAGDVESNPGP | E2A artificial |
| 4 | VKQTLNFDLLKLAGDVESNPGP | F2A artificial |
| 5 | RKVCNGIGIGEFKDSLSINATNIKHFKNCTSISGDLHILPVAFRGDSFTHTPPLDPQEL DILKTVKEITGFLLIQAWPENRTDLHAFENLEIIRGRTKQHGQFSLAVVSLNITSLGLRS LKEISDGDVIISGNKNLCYANTINWKKLFGTSGQKTKIISNRGENSCKATGQVCHALC SPEGCWGPEPRDCVSCRNVSRGRECVDKCNLLEGEPREFVENSECIQCHPECLPQA MNITCTGRGPDNCIQCAHYIDGPHCVKTCPAGVMGENNTLVWKYADAGHVCHLC HPNCTYGCTGPGLEGCPTNGPKIPSIATGMVGALLLLLVVALGIGLFM | tEGFR artificial |
| 6 | ESKYGPPCPPCP | spacer (IgG4hinge) (aa) *Homo sapiens* |
| 7 | ESKYGPPCPPCPGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQK SLSLSLGK | Hinge-CH3 spacer *Homo sapiens* |
| 8 | ESKYGPPCPPCPAPEFLGGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSL SLGK | Hinge-CH2-CH3 spacer *Homo sapiens* |
| 9 | RWPESPKAQASSVPTAQPQAEGSLAKATTAPATTRNTGRGGEEKKKEKEKEEQEER ETKTPECPSHTQPLGVYLLTPAVQDLWLRDKATFTCFVVGSDLKDAHLTWEVAGKV PTGGVEEGLLERHSNGSQSQHSRLTLPRSLWNAGTSVTCTLNHPSLPPQRLMALRE PAAQAPVKLSLNLLASSDPPEAASWLLCEVSGFSPPNILLMWLEDQREVNTSGFAP ARPPPQPGSTTFWAWSVLRVPAPPSPQPATYTCVVSHEDSRTLLNASRSLEVSYVT DH | IgD-hinge-Fc *Homo sapiens* |
| 10 | GCTGATGGAGTACGACGAGC | PAX5 gRNA target 1 |
| 11 | TGTGAATGGACGGCCACTCC | PAX5 gRNA target 2 |
| 12 | GGCTCGTCGTACTCCATCAG | PAX5 gRNA target 3 |
| 13 | TTGGATCCTCCAATTACCCC | PAX5 gRNA target 4 |
| 14 | GGTCCTAGGTATTATGAGAC | PAX5 gRNA target 5 |
| 15 | TGTAGTCCGCCAGAGGATAG | PAX5 gRNA target 6 |
| 16 | CAGTATTAACCCTGCGCCCT | BACH2 gRNA target 1 |
| 17 | CGGCCCAGCGCTGCCGCAAA | BACH2 gRNA target 2 |
| 18 | GTCTGCTTCCGAGAACGATC | BACH2 gRNA target 3 |
| 19 | GTTCCTGCGCATGCACAACC | BACH2 gRNA target 4 |
| 20 | AGTTTATTCATGATGTCCGA | BACH2 gRNA target 5 |
| 21 | CTGTGACGTGACTTTGATCG | BACH2 gRNA target 6 |
| 22 | CTACAAGTGTGACCGCTGCC | BCL6 gRNA target 1 |
| 23 | CAGGGCCATACCGGTATGGA | BCL6 gRNA target 2 |
| 24 | GAGCCGCAGGACGTGCACTT | BCL6 gRNA target 3 |

-continued

| # | SEQUENCE | ANNOTATION |
|---|---|---|
| 25 | TAACCAGACCCTTCCGGTTC | BCL6 gRNA target 4 |
| 26 | TGTTAACGATGTTATTGAGC | BCL6 gRNA target 5 |
| 27 | AGCATGTTGTGGACACTTGC | BCL6 gRNA target 6 |
| 28 | TTCACACGGACGCCCTGGTA | OBF1 gRNA target 1 |
| 29 | ACTCTCACCGCCGTAGGTGC | OBF1 gRNA target 2 |
| 30 | CTCCAAAAGCAGCTTGTCGA | OBF1 gRNA target 3 |
| 31 | AAGCTCCGCCACGCCCGCAG | OBF1 gRNA target 4 |
| 32 | AGAGGCATAGGTCAACACTG | OBF1 gRNA target 5 |
| 33 | AGCTTCATGGGGCACATACT | OBF1 gRNA target 6 |
| 34 | GACTCCCCATCAGAGCACAC | OCT2 gRNA target 1 |
| 35 | TGCTCAGTTCCTGCTACCGC | OCT2 gRNA target 2 |
| 36 | CCAGTTGGGGACACGGAGAA | OCT2 gRNA target 3 |
| 37 | TGCGGTAGCAGGAACTGAGC | OCT2 gRNA target 4 |
| 38 | CAGGTGCTTACCTTTGTACT | OCT2 gRNA target 5 |
| 39 | GGAGTCCAGACCTTGCTTCT | OCT2 gRNA target 6 |
| 40 | AATACTCGTGCGTTTGGCGT | PU.1 gRNA target 1 |
| 41 | GCTCCGCAGCGGCGACATGA | PU.1 gRNA target 2 |
| 42 | GTGTCTGACGGCGAGGCGGA | PU.1 gRNA target 3 |
| 43 | TCTCGAACTCGCTGTGCACG | PU.1 gRNA target 4 |
| 44 | CCAGCACTTCGCCGCTGAAC | PU.1 gRNA target 5 |
| 45 | GATCCGTGTCATAGGGCACC | PU.1 gRNA target 6 |
| 46 | CGGCACCACCATGCTCGCCC | SPIB gRNA target 1 |
| 47 | CGGGCCACACTTCAGCTGTC | SPIB gRNA target 2 |
| 48 | AGATGGCGTCTTCTATGACC | SPIB gRNA target 3 |
| 49 | CTCACCAGACAGCTGAAGTG | SPIB gRNA target 4 |
| 50 | TCACTTACTGTGCAGCCTCC | SPIB gRNA target 5 |
| 51 | CCAGGAGCCCCCTCTGAATC | SPIB gRNA target 6 |
| 52 | GAGAGTCGGCTTGAGATCGA | ETS1 gRNA target 1 |
| 53 | TGGAAACCACAGTTCATTCG | ETS1 gRNA target 2 |
| 54 | GAAGATCCTCGAATGAACTG | ETS1 gRNA target 3 |
| 55 | GACTCTCACCATCATCAAGA | ETS1 gRNA target 4 |
| 56 | CACTAAAGAACAGCAACGAC | ETS1 gRNA target 5 |
| 57 | ACGAGGCGCTGAGTAAGGGA | ETS1 gRNA target 6 |
| 58 | ACCTGAATGGTGCGCGTCGT | IRF8 gRNA target 1 |
| 59 | ACCTACGACGCGCACCATTC | IRF8 gRNA target 2 |
| 60 | GTGGTCGGCGGCTTCGACAG | IRF8 gRNA target 3 |
| 61 | GCGTAACCTCGTCTTCCAAG | IRF8 gRNA target 4 |

-continued

| # | SEQUENCE | ANNOTATION |
|---|----------|------------|
| 62 | CGGAAATGTCCAGTTGGGAC | IRF8 gRNA target 5 |
| 63 | ATTGACAGTAGCATGTATCC | IRF8 gRNA target 6 |
| 64 | ACTTTGCAAGCCGAGAGCCG | IRF4 SAM gRNA 1 |
| 65 | CGGGAACCCCACCCCGGCCG | IRF4 SAM gRNA 2 |
| 66 | GCAGCCCCAGCCTTCACGC | IRF4 SAM gRNA 3 |
| 67 | ATCTTCTTACTTCCCTTTGA | BLIMP1 SAM gRNA 1 |
| 68 | ATGCGAAGAGAGGAAGCTCT | BLIMP1 SAM gRNA 2 |
| 69 | CGGCTGTGCTAGCAATCTGG | BLIMP1 SAM gRNA 3 |
| 70 | ACAAGTGTTACTTTAGGACT | BLIMP1 SAM gRNA 4 |
| 71 | CTTGGAACCTTGCCTTTTTG | BLIMP1 SAM gRNA 5 |
| 72 | GGAAACACTGGGTGGGGCAA | BLIMP1 SAM gRNA 6 |
| 73 | AGGACCGTGGCTATGGAGTC | XBP1 SAM gRNA 1 |
| 74 | GACCCCAAGTACCTTTGGCC | XBP1 SAM gRNA 2 |
| 75 | GGCGTGGCAGCGGCAATCCC | XBP1 SAM gRNA 3 |
| 76 | MEFGLRWVFLVAILKDVQC | Ig HC signal peptide 1 |
| 77 | MEFGLSWVFLVAILKGVQC | Ig HC signal peptide 2 |
| 78 | MELGLSWVFLVAILKGVQC | Ig HC signal peptide 3 |
| 79 | MELGLRWVFLVAFLEGVQC | Ig HC signal peptide 4 |
| 80 | MELGLRWVFLVTFFWGVQC | Ig HC signal peptide 5 |
| 81 | MELGLRWVLLVAILEGVHC | Ig HC signal peptide 6 |
| 82 | MELGLRWVFLVALLEGVHC | Ig HC signal peptide 7 |
| 83 | MELGLRWVFLIATLAGARC | Ig HC signal peptide 8 |
| 84 | MELGLRWVFLVAILEGVQC | Ig HC signal peptide 9 |
| 85 | MELGLYWVFLVAILEGVQC | Ig HC signal peptide 10 |
| 86 | MDLGLYWVFLVAILEGVEC | Ig HC signal peptide 11 |
| 87 | MELGLCWVFLVAILEGVPC | Ig HC signal peptide 12 |
| 88 | MELGLCWVFLVAILEGVQC | Ig HC signal peptide 13 |
| 89 | MELGLNWVLLVAILEGVQC | Ig HC signal peptide 14 |
| 90 | MELGLSWVFLVAILEGVHC | Ig HC signal peptide 15 |
| 91 | MELGLSWVFLVAILEGVQC | Ig HC signal peptide 16 |
| 92 | MELGLSWVFLVVILEGVQC | Ig HC signal peptide 17 |
| 93 | MESGLTWLFLVAILKGVHC | Ig HC signal peptide 18 |
| 94 | MKHLWFFLLLVAAPRWVLS | Ig HC signal peptide 19 |
| 95 | MKHLWFFLLLVAPPRWVLS | Ig HC signal peptide 20 |
| 96 | MKHLWFFLLLVATPRWVLS | Ig HC signal peptide 21 |
| 97 | MRHLWFFLLLVAAPRWVLS | Ig HC signal peptide 22 |
| 98 | MKHLWFFFLLVAAPRSVLS | Ig HC signal peptide 23 |
| 99 | MSVSFLIFLPVLGLPWGVLS | Ig HC signal peptide 24 |

| # | SEQUENCE | ANNOTATION |
|---|---|---|
| 100 | MGHPWFFLLLVTAPRWVLS | Ig HC signal peptide 25 |
| 101 | MDWTWRILFLVAAATGAHS | Ig HC signal peptide 26 |
| 102 | MDWTWRILFLVAAATDAYS | Ig HC signal peptide 27 |
| 103 | MDWTWRILFLVAAATSAHS | Ig HC signal peptide 28 |
| 104 | MDWTWRILFLVAAATEAHS | Ig HC signal peptide 29 |
| 105 | MDWTWRILFLVTAATGAHS | Ig HC signal peptide 30 |
| 106 | MDWTWRLLFLVAAVTSAHS | Ig HC signal peptide 31 |
| 107 | MDWTWSILFLVAAATGAHS | Ig HC signal peptide 32 |
| 108 | MDWTWSILFLVTAATGAHS | Ig HC signal peptide 33 |
| 109 | MDWTWSILFLVAGASGAHS | Ig HC signal peptide 34 |
| 110 | MDWTWSILFLVAAATGARP | Ig HC signal peptide 35 |
| 111 | MGWTWSILFLVAATTGAPS | Ig HC signal peptide 36 |
| 112 | MDWTWSILFLVAAATGAQS | Ig HC signal peptide 37 |
| 113 | MDWAWRILFLVAAATGVHS | Ig HC signal peptide 38 |
| 114 | MDCTWRILLLVAVATGTHA | Ig HC signal peptide 39 |
| 115 | MDCTWRILLLVAAATGTHA | Ig HC signal peptide 40 |
| 116 | MDWTWRILFLAAAATGVQS | Ig HC signal peptide 41 |
| 117 | MDWTWTILFLVAGATGVKS | Ig HC signal peptide 42 |
| 118 | MDWTWSILFLVAAATGVHS | Ig HC signal peptide 43 |
| 119 | MDWTWRFLFVVAAVTGVQS | Ig HC signal peptide 44 |
| 120 | MDWTWILFLVAAATRVHS | Ig HC signal peptide 45 |
| 121 | MDWTWRFLLVVAAATGVPS | Ig HC signal peptide 46 |
| 122 | MDWTWRFLIVVAAATGVQS | Ig HC signal peptide 47 |
| 123 | MDWTWRFLFVVAAATSVQS | Ig HC signal peptide 48 |
| 124 | MDWTWRFLFVVAAATGVQS | Ig HC signal peptide 49 |
| 125 | MDWTWRFLFVVAAGTGVQS | Ig HC signal peptide 50 |
| 126 | MDWTWRFLFVVAASTGVQS | Ig HC signal peptide 51 |
| 127 | MDWTWRVLFVVAASTGVQS | Ig HC signal peptide 52 |
| 128 | MDRTWRLLFVVAAATGVQS | Ig HC signal peptide 53 |
| 129 | MDWTWRFLFVVAAAGVQS | Ig HC signal peptide 54 |
| 130 | MGWTWRFLFVVAAAGVQS | Ig HC signal peptide 55 |
| 131 | MDWTWTFLFVVAAATGVQS | Ig HC signal peptide 56 |
| 132 | MDWTWRVFCLLAVAPGVQS | Ig HC signal peptide 57 |
| 133 | MDWTWRVFCLLAVAPGADS | Ig HC signal peptide 58 |
| 134 | MDWTWRVFCLLAVAPGANS | Ig HC signal peptide 59 |
| 135 | MDWTWRVFCLLAVAPGAHS | Ig HC signal peptide 60 |
| 136 | MDWTWRVFCLLAVISGGQS | Ig HC signal peptide 61 |

| # | SEQUENCE | ANNOTATION |
|---|---|---|
| 137 | MDWTWRFLFVVAVAIGVQS | Ig HC signal peptide 62 |
| 138 | MDLMCKKMKHLWFFLLLVAAPRWVLS | Ig HC signal peptide 63 |
| 139 | MDLLHKNMKHLWFFLLLVAAPRWVLS | Ig HC signal peptide 64 |
| 140 | MGLLHKNMKHLWFFLLLVAAPRWVLS | Ig HC signal peptide 65 |
| 141 | MDLLHKNMKHLWFFLLLVAAPRWGLS | Ig HC signal peptide 66 |
| 142 | MDVMCKKMKHLWFFLLLVAAPRWVLA | Ig HC signal peptide 67 |
| 143 | MDLKCKKMKRLWLFLLLVAAPRWVLS | Ig HC signal peptide 68 |
| 144 | MDLLCKNMKHLWFFLLLVAAPRWVLS | Ig HC signal peptide 69 |
| 145 | MDLLCKKMKHLWFFLLLVAAPRWVLS | Ig HC signal peptide 70 |
| 146 | MELMCKKMKHLWFFLLLVAAPRWVLS | Ig HC signal peptide 71 |
| 147 | MDLMCKKMKHLWFFLLLVAAPGWVLS | Ig HC signal peptide 72 |
| 148 | MCKTMKQLWFFLLLVAAPRWVLS | Ig HC signal peptide 73 |
| 149 | MAKTNLFLFLIFSLLLSLSSAAQPAMA | Ig HC signal peptide 74 |
| 150 | MDTLCSTLLLLTIPSWVLS | Ig HC signal peptide 75 |
| 151 | MGSTAILALLLAVLQGVCA | Ig HC signal peptide 76 |
| 152 | MELSLSWFFLLTIIQGVQC | Ig HC signal peptide 77 |
| 153 | MELGLSWIFLLAILKGVQC | Ig HC signal peptide 78 |
| 154 | MDLGLSWIFLLTILKGVQC | Ig HC signal peptide 79 |
| 155 | MELGLTWIFLLAILKGVQC | Ig HC signal peptide 80 |
| 156 | MELGLSWIFLVAILKGVQC | Ig HC signal peptide 81 |
| 157 | MDLGLSWLFLVALLKGVQC | Ig HC signal peptide 82 |
| 158 | MEFGLSCVFLVAIFKGVHC | Ig HC signal peptide 83 |
| 159 | MEFGLSCLFLVAILKGVRC | Ig HC signal peptide 84 |
| 160 | MEFGLSWIFLVVIIKGVQC | Ig HC signal peptide 85 |
| 161 | MEFGLSWIFLVVILKGVQC | Ig HC signal peptide 86 |
| 162 | MEFGLSWIFLATILKGVQC | Ig HC signal peptide 87 |
| 163 | MEFGLSWIFLAAILKGVQC | Ig HC signal peptide 88 |
| 164 | MEFGLSWIFLAAILKGVQG | Ig HC signal peptide 89 |
| 165 | MKFGLSWIFLPAILKGVQC | Ig HC signal peptide 90 |
| 166 | MEFGLSWLFLVAILKGVQC | Ig HC signal peptide 91 |
| 167 | MEFGLSWLLLVAILKGVQC | Ig HC signal peptide 92 |
| 168 | MEFGLSWLFLVTILKGVQC | Ig HC signal peptide 93 |
| 169 | MEFGLSWVFLVAIIKGVQCQV | Ig HC signal peptide 94 |
| 170 | MEFGLSWVFLVAIIKGVQC | Ig HC signal peptide 95 |
| 171 | MEFGLSWVFLVAVIKGVQC | Ig HC signal peptide 96 |
| 172 | MEFGLTWVFLVAVIKGVHC | Ig HC signal peptide 97 |
| 173 | MQFGLSWVFLVALLRGVQC | Ig HC signal peptide 98 |
| 174 | MDFGLAWVFLVALLRGVQC | Ig HC signal peptide 99 |

| # | SEQUENCE | ANNOTATION |
|---|---|---|
| 175 | MEFGLNWVLLVALLRGVQC | Ig HC signal peptide 100 |
| 176 | MEFGLSWVFLVALLRGVQC | Ig HC signal peptide 101 |
| 177 | MEFGLSWVFLVALLRGVEC | Ig HC signal peptide 102 |
| 178 | MEFGLSWVFLVALFRGVQC | Ig HC signal peptide 103 |
| 179 | MESGLSWVFLVALLRGVQC | Ig HC signal peptide 104 |
| 180 | MELGLSWVFLVSLLAGVQC | Ig HC signal peptide 105 |
| 181 | MELGLSWIFLVALLRGVQC | Ig HC signal peptide 106 |
| 182 | MEFGLSWVLLVVFLQGVQC | Ig HC signal peptide 107 |
| 183 | MEFGLSWVFLVGILKGVQC | Ig HC signal peptide 108 |
| 184 | MEFGLSWVYLVAILKGVQC | Ig HC signal peptide 109 |
| 185 | MEFWLSWVFLVAILKGVQC | Ig HC signal peptide 110 |
| 186 | MVLQTQVFISLLLWISGSYG | Ig LC signal peptide 1 |
| 187 | MRLPAQLLGLLMLWVSGSSG | Ig LC signal peptide 2 |
| 188 | METPAQLLFLLLLWLPVSDTTG | Ig LC signal peptide 3 |
| 189 | METPAQLLFLLLLWLPGTTG | Ig LC signal peptide 4 |
| 190 | METPAQLLFLLLLWLPDITG | Ig LC signal peptide 5 |
| 191 | MEAPAQLLFLLLLWLPDSTG | Ig LC signal peptide 6 |
| 192 | MEAPAQLLFLLLLWLPDTTG | Ig LC signal peptide 7 |
| 193 | MDMRVLAQLLGLLLLCFPGARC | Ig LC signal peptide 8 |
| 194 | MDMRVPAQLLGLLLLWLPDTRC | Ig LC signal peptide 9 |
| 195 | MDMRVPAQLLGLLLLWLRGARC | Ig LC signal peptide 10 |
| 196 | MDMRVPAQLLGLLLLWLSGARC | Ig LC signal peptide 11 |
| 197 | MKYLLPTAAAGLLLLAAQPAMA | Ig LC signal peptide 12 |
| 198 | MKYLLPTAAAGLLLHAAQPAMA | Ig LC signal peptide 13 |
| 199 | MKKNIAFLLASMFVSIATNAYA | Ig LC signal peptide 14 |
| 200 | MKQSTIALALLPLLFTPVTKA | Ig LC signal peptide 15 |
| 201 | MKKTAIAIAVALAGFATVAQAA | Ig LC signal peptide 16 |
| 202 | MLLLVTSLLLCELPHPAFLLIP | Signal peptide |
| 203 | ATGCAAAT | Variable region promoter octamer sequence |
| 204 | CGGCCCCGATGCGGGACTGCGTTTTGACCATCATAAATCAAGTTTATTTTTTAATTAATTGAGCGAAGCTGGAAGCAGATGATGAATTAGAGTCAAGATGGCTGCATGGGGGTCTCCGGCACCCACAGCAGGTGGCAGGAAGCAGGTCACCGCGAGAGTCTATTTTAGGAAGCAAAAAAACACAATTGGTAAATTTATCACTTCTGGTTGTGAAGAGGTGGTTTTGCCCAGGCCCAGATCTGAAAGTGCTCTACTGAGCAAAACAACACCTGGACAATTTGCGTTTCTAAAATAAGGCGAGGCTGACCGAAACTGAAAGGCTTTTTTTAACTATCTGAATTTCATTTCCAATCTTAGCTTATCAACTGCTAGTTTGTGCAAACAGCATATCAACTTCTAAACTGCATTCATTTTTAAAGTAAGATGTTTAAGAAATTAAACAGTCTTAGGGAGAGTTTATGACTGTATTCAAAAGTTTTTTAAATTAGCTTGTTATCCCTTCATGTGATAATTAATCTCAAATACTTTTTCGATACCTCAGAGCATTATTTTCATAATGACTGTGTTCACAATCTTTTT | Heavy chain intronic enhancer |

| # | SEQUENCE | ANNOTATION |
|---|---|---|
| 205 | LEGGGEGRGSLLTCGDVEENPGPR | T2A artificial |
| 206 | GSGATNFSLLKQAGDVEENPGP | P2A artificial |
| 207 | RKVCNGIGIGEFKDSLSINATNIKHFKNCTSISGDLHILPVAFRGDSFTHTPPLDPQELDI LKTVKEITGFLLIQAWPENRTDLHAFENLEIIRGRTKQHGQFSLAVVSLNITSLGLRSLKE ISDGDVIISGNKNLCYANTINWKKLFGTSGQKTKIISNRGENSCKATGQVCHALCSPEGCW GPEPRDCVSCRNVSRGRECVDKCNLLEGEPREFVENSECIQCHPECLPQAMNITCTGRGPD NCIQCAHYIDGPHCVKTCPAGVMGENNTLVWKYADAGHVCHLCHPNCTYGCTGPGLEGCPT NGPKIPSIATGMVGALLLLLVVALGIGLFM | tEGFR |
| 208 | MVSKGEELFTGVVPILVELDGDVNGHKFSVRGEGEGDATNGKLTLKFICTTGKLPVPWPTL VTTLTYGVQCFSRYPDHMKQHDFFKSAMPEGYVQERTITFKDDGTYKTRAEVKFEGDTLVN RIELKGIDFKEDGNILGHKLEYNFNSHNVYITADKQKNGIKANFKIRHNVEDGSVQLADHY QQNTPIGDGPVLLPDNHYLSTQSKLSKDPNEKRDHMVLLEFVTAAGITHGMDELYKMVSKG EELFTGVVPILVELDGDVNGHKFSVRGEGEGDATNGKLTLKFICTTGKLPVPWPTLVTTLT YGVQCFSRYPDHMKQHDFFKSAMPEGYVQERTITFKDDGTYKTRAEVKFEGDTLVNRIELK GIDFKEDGNILGHKLEYNFNSHNVYITADKQKNGIKANFKIRHNVEDGSVQLADHYQQNTP IGDGPVLLPDNHYLSTQSKLSKDPNEKRDHMVLLEFVTAAGITHGMDELYK | super-fold green fluorescent protein |

The invention claimed is:

1. An engineered B cell comprising one or more nucleic acid molecules comprising one or more coding sequences encoding an exogenous protein under the control of one or more elements to effect secretion of the exogenous protein from the cell, wherein the engineered B cell comprises a recombinant receptor capable of binding with specificity to a ligand, wherein binding of the recombinant receptor to the ligand leads to increased expression and/or secretion of the exogenous protein, and wherein the exogenous protein is a therapeutic protein comprising coagulation factor VIII or coagulation factor IX.

2. The engineered B cell of claim 1, wherein the engineered B cell expresses an endogenous antibody and comprises a modification that prevents class-switching of the endogenous antibody and/or prevents switching of the endogenous antibody from a membrane-associated form to a secreted form.

3. The engineered B cell of claim 2, wherein:
the modification that prevents class-switching comprises: reduced or eliminated expression of activation-induced deaminase (AID), uracil DNA glycosylase, and/or apyrimidic/apurinic (AP)-endonucleases.

4. The engineered B cell of claim 2, wherein the modification that prevents switching of an endogenous antibody expressed in the engineered B cell from a membrane-associated form to a secreted form comprises mutation of the polyadenylation signal upstream of the M1 exon at the endogenous antibody locus.

5. The engineered B cell of claim 2, wherein the modification that prevents class-switching comprises mutation of one or more switch regions in the endogenous antibody locus.

6. The engineered B cell of claim 1,
wherein, upon ligand binding, the receptor is capable of inducing (i) a mitogenic or proliferative signal, and/or (ii) a signal that is capable of modulating the differentiation of the engineered B cell.

7. The engineered B cell of claim 6, wherein the exogenous protein does not bind to the target of the ligand binding domain of the recombinant receptor and/or the exogenous protein does not contain a ligand binding site contained in the ligand binding domain of the recombinant receptor.

8. The engineered B cell of claim 1, wherein the engineered B cell is a human primary B cell.

9. The engineered B cell of claim 1, wherein the engineered B cell comprises: one or more phenotypic markers selected from:
PAX5$^+$, BACH2$^+$, BCL-2$^+$, OBF1$^+$, OCT2$^+$, PU.1$^+$, SPIB$^+$, ETS1$^+$, IRF8$^+$, IRF4$^{low}$, BLIMP1$^+$, and XBP1$^+$; and/or one or more cell surface markers selected from CD19$^+$, CD20$^+$, CD21$^+$, CD22$^+$, CD23$^+$, CD24$^+$, CD10$^-$, CD27$^-$, and CD38$^{low}$.

10. The engineered B cell of claim 1, wherein the engineered B cell comprises one or more modifications resulting in a greater capacity for the engineered B cell to produce and/or secrete the exogenous protein, wherein the one or more modifications comprise: reduced or eliminated expression of one or more proteins selected from PAX5, BACH2, BCL-6, OBF1, OCT2, PU.1, SPIB, ETS1, and IRF8.

11. The engineered B cell of claim 1, wherein the one or more nucleic acid molecules further comprises at least one promoter operably linked to one of the one or more coding sequences.

12. The engineered B cell of claim 11, wherein the promoter is a B cell promoter, a plasma cell promoter, or an immunoglobulin promoter.

13. The engineered B cell of claim 11, wherein the promoter is a constitutively active promoter comprising an SV40, CMV, UBC, EF1A, PGK or CAGG promoter.

14. The engineered B cell of claim 13, wherein the conditional promoter comprises a Lac operator sequence, a tetracycline operator sequence, a galactose operator sequence or a doxycycline operator sequence, or is an analog thereof.

15. The engineered B cell of claim 11, wherein expression of the exogenous protein is conditional or inducible, and at least one of the one or more coding sequences is operably linked to a conditional or inducible promoter, enhancer, or transactivator.

16. The engineered B cell of claim 1, wherein at least one of the one or more nucleic acid molecules is integrated into or replaces all or a portion of a heavy chain immunoglobulin locus or a light chain immunoglobulin locus of the B cell.

17. The engineered B cell of claim 1, wherein the B cell comprises an agent or genetic disruption that reduces or eliminates expression of an endogenous immunoglobulin heavy and/or light chain product.

18. The engineered B cell of claim 1, wherein the recombinant receptor is a chimeric receptor comprising an ITAM-containing intracellular signaling domain, wherein the signaling domain is separated from the ligand-binding domain by a transmembrane domain.

19. The engineered B cell of claim 1, wherein the recombinant receptor is contained in a complex comprising an endogenous protein comprising an ITAM-containing intracellular signaling domain.

20. The engineered B cell of claim 1, wherein the exogenous protein and the recombinant receptor bind to different ligands.

21. The engineered B cell of claim 1, wherein the exogenous protein is secreted from the cell or is capable of being secreted from the cell upon ligand binding.

22. A pharmaceutical composition comprising the engineered B cell of claim 1 and a pharmaceutically acceptable carrier.

23. An article of manufacture, comprising the engineered B cell of claim 1.

24. The engineered B cell of claim 1, wherein the recombinant receptor comprises a heterologous antibody.

25. The engineered B cell of claim 1, comprising a nucleic acid encoding the recombinant receptor, wherein the nucleic acid encoding the recombinant receptor is a separate nucleic acid molecule from the one or more nucleic acid molecules encoding the exogenous protein; or the nucleic acid encoding the recombinant receptor is comprised by the one or more nucleic acid molecules encoding the exogenous protein.

26. The engineered B cell of claim 25, wherein:
the nucleic acid encoding the recombinant receptor is integrated into a heavy chain immunoglobulin locus,
the nucleic acid molecule(s) encoding the exogenous protein is integrated into a heavy chain immunoglobulin locus or a light chain immunoglobulin locus; and
one or more light chain locus is deleted or disrupted.

27. The engineered B cell of claim 1, wherein the one or more coding sequences comprises a nucleotide sequence encoding a secretory signal peptide.

28. The engineered B cell of claim 1, wherein the engineered B cell comprises one or more phenotypic markers selected from PAX5$^-$, BACH2$^-$, BCL-2$^-$, OBF1$^-$, OCT2$^-$, PU.1$^-$, SPIB$^-$, ETS1$^-$, IRF8$^-$, IRF4$^{hi}$, BLIMP1$^{mid}$, and XBP1$^+$; and/or one or more surface markers selected from CD19$^+$, CD38$^{high}$, CD27$^{high}$, CD269$^+$, MHCII$^+$, CD20$^-$, and CD138$^-$.

29. The engineered B cell of claim 1, wherein the engineered B cell comprises one or more phenotypic markers selected from PAX5$^-$, BACH2$^-$, BCL-2$^-$, OBF1$^-$, OCT2$^-$, PU.1$^-$, SPIB$^-$, ETS1$^-$, IRF8$^-$, IRF4$^{hi}$, BLIMP1$^{hi}$, and XBP1$^+$; and/or one or more surface markers selected from CXCR4$^+$, CD27$^+$, CD38$^{high}$, CD138$^+$, CD269$^+$, CD19$^{low}$, CD20$^-$, and MHCII$^{-/low}$.

30. The engineered B cell of claim 1, wherein the engineered B cell is a human plasmablast, plasma cell, or memory B cell.

31. The engineered B cell of claim 1, wherein the engineered B cell is a human B cell capable of differentiating into one or more of a plasmablast, a plasma cell, and a memory B cell.

32. The engineered B cell of claim 1, wherein the engineered B cell is a human naïve mature B cell.

33. The engineered B cell of claim 1, wherein the exogenous protein and the recombinant receptor have different ligand binding sites.

34. The engineered B cell of claim 1, wherein at least one of the one or more nucleic acid molecules comprises one or more coding sequences operably linked to an endogenous immunoglobulin promoter selected from an immunoglobulin heavy chain promoter, a kappa light chain promoter, or a lambda light chain promoter.

35. The engineered B cell of claim 1, wherein the engineered B cell comprises one or more modifications resulting in a greater capacity for the engineered B cell to produce and/or secrete the exogenous protein, wherein the one or more modifications comprise: increased expression of one or more proteins selected from the group consisting of IRF4, BLIMP1, and XBP1.

36. The engineered B cell of claim 1, wherein the engineered B cell is a plasma cell.

37. The plasma cell of claim 36, wherein the plasma cell comprises the phenotypic marker PAX5–.

38. The plasma cell of claim 36, wherein the plasma cell comprises the phenotypic marker BACH2–.

39. The plasma cell of claim 38, wherein the plasma cell comprises the phenotypic marker PAX5–.

40. The engineered B cell of claim 1, wherein the engineered B cell comprises the phenotypic markers CD27$^+$, CD38$^{high}$, CD138$^+$, and CD19$^{low}$.

41. The engineered B cell of claim 1, wherein the engineered B cell comprises the phenotypic marker IRF4$^{high}$.

* * * * *